US009976131B2

(12) United States Patent
Gehlsen et al.

(10) Patent No.: US 9,976,131 B2
(45) Date of Patent: May 22, 2018

(54) RIBOTOXIN MOLECULES DERIVED FROM SARCIN AND OTHER RELATED FUNGAL RIBOTOXINS

(71) Applicant: Research Corporation Technologies, Inc., Tucson, AZ (US)

(72) Inventors: Kurt R. Gehlsen, Tucson, AZ (US); Timothy David Jones, Cambridgeshire (GB); Francis Joseph Carr, Aberdeenshire (GB); Arron Hearn, Cambridgeshire (GB)

(73) Assignee: RESEARCH CORPORATION TECHNOLOGIES, INC., Tucson, AZ (US)

( * ) Notice: Subject to any disclaimer, the term of this patent is extended or adjusted under 35 U.S.C. 154(b) by 0 days. days.

(21) Appl. No.: 15/430,906

(22) Filed: Feb. 13, 2017

(65) Prior Publication Data

US 2017/0204387 A1  Jul. 20, 2017

Related U.S. Application Data

(63) Continuation of application No. 14/774,445, filed as application No. PCT/US2014/020035 on Mar. 3, 2014, now Pat. No. 9,603,911.

(60) Provisional application No. 61/783,589, filed on Mar. 14, 2013, provisional application No. 61/902,972, filed on Nov. 12, 2013.

(51) Int. Cl.
  *C12N 15/62* (2006.01)
  *C12N 9/22* (2006.01)

(52) U.S. Cl.
  CPC ............. *C12N 9/22* (2013.01); *C12N 15/62* (2013.01); *C12Y 301/2701* (2013.01)

(58) Field of Classification Search
  None
  See application file for complete search history.

(56) References Cited

U.S. PATENT DOCUMENTS

| 9,603,911 B2 * | 3/2017 | Gehlsen ................. C07K 14/38 |
| 2006/0013809 A1 | 1/2006 | Vincent et al. |
| 2011/0212114 A1 | 9/2011 | Williams |

FOREIGN PATENT DOCUMENTS

| EP | 0524768 A2 | 1/1993 |
| JP | 05-292960 | 11/1993 |

OTHER PUBLICATIONS

European Office Action dated Nov. 22, 2017 for European Application No. 14775634.0, 6 pages.
Database UniProt [Online] Jul. 1, 1997 (Jul. 1, 1997), "SubName: Full=Gigantin {ECO:0000313|EMBL:CAA69713.1};", retreived from EMB accession No. UNIPROT:P87063, Database accession No. P87063.
Database UniProt [Online] Jan. 1, 1998 (Jan. 1, 1998), "SubName: Full=A-sarcin {ECO:0000313|EMBL:AAB66604.1};", retrieved from EMB accession No. UNIPROT:O13324, Database accession No. O13324.
Database UniProt [Online] Jan. 1, 1998 (Jan. 1, 1998), "SubName: Full=A-sarcin {ECO:0000313|EMBL:AAB66601.1};", retrieved from EMB accession No. UNIPROT:O13322, Database accession No. O13322.
Japanese Office Action dated Apr. 18, 2017 for Japanese Application No. 2016-500564, 20 pages (with English ranslation).
Endo et al., "Preparation of α-Sarcin Variant and Analysis of its RNase Activity", The Joint Annual Meeting Lecture of the 69th Annual Meeting of the Japanese Biochemical Society and the 19th Annual Meeting of the Molecular Biology Society of Japan, Abstracts, 1996, p. 399, 3-P-0100.
Tatsuzo Oka, "Development of a Novel Immunotoxin Using a Recombinant α-Sarcin and Use of the Immunotoxin in the Treatment of Hematopoietic Organ Tumors", Daiichi Sankyo Foundation of Life Science, Research Reports, 1998, vol. 12, pp. 46-56.
Garcia-Mayoral et al., "NMR structure of the noncytotoxic α-sarcin mutant (7-22): The importance of the native conformation of peripheral loops for activity", Protein Science, Apr. 2004, vol. 13, No. 4, pp. 1000-1011.
Sacco et al., "The primary structure of the cytotoxin α-sarcin", The Journal of Biological Chemistry, May 183, vol. 258, No. 9, pp. 5811-5818.
Lacadena et al., "Fungal ribotoxins: molecular dissection of a family of natural killers", Federation of European Microbiological Societies Review, Jan. 2007, vol. 31, pp. 212-237.
International Search Report dated Oct. 25, 2016 from International Application No. PCT/US2014/020035, 10 pages.
Alford et al., "alpha-Sarcin catalytic activity is not required for cytotoxicity", BMC Biochemistry, 2009, vol. 10, No. 9, 11 pages.
Garcia-Ortega et al., "Deletion of the NH2-terminal β-Hairpin of the Ribotoxin α-Sarcin Produces a Nontoxic but Active Ribonuclease", The Journal of Biological Chemistry, May 24, 2002, vol. 277, No. 21, pp. 18632-18639.
Carreras-Sangra et al., "The Therapeutic Potential of Fungal Ribotoxins", Current Pharmaceutical Biotechnology, 2008, vol. 9, No. 3, pp. 153-160.
Lacadena et al., "Fungal ribotoxins: molecular dissection of a family of natural killers", FEMS Microbiology Reviews, 2007, vol. 31, No. 2, pp. 212-237.
Jones et al., "The Development of a Modified Human IFN-α2b Linked to the Fc Portion of Human IgG1 as a Novel Potential Therapeutic for the Treatment of Hepatitis C Virus Infection", Journal of Interferon and Cytokine Research, vol. 24, No. 9, 2004, vol. 24, pp. 560-572.
Mazar et al., "Recombinant immunotoxin for cancer treatment with low immunogenicity by identification and silencing of human T-cell epitopes", Proceedings of the National Academy of Sciences, Jun. 10, 2014, vol. 111, No. 23, pp. 3571-8576.

(Continued)

*Primary Examiner* — Padmavathi Baskar
(74) *Attorney, Agent, or Firm* — MH2 Technology Law Group, LLP

(57) ABSTRACT

The present application relates to modified T cell epitopes derived from fungal ribotoxins, including α-sarcin, clavin, gigantin, mitogillin, and restrictocin, as well as modified ribotoxin molecules comprising one or more of the modified epitopes. The modified ribotoxin molecules inhibit protein synthesis, like the wild type ribotoxins, but exhibit reduced immunogenicity as compared to the corresponding wild type ribotoxin. Another aspect relates to a fusion protein which comprises a modified ribotoxin fused or conjugated or otherwise linked to a targeting molecule that is effective for binding a target of interest. Another aspect relates to the use of the modified ribotoxin or fusion protein for treating or managing a disease or condition.

15 Claims, 8 Drawing Sheets

(56) References Cited

OTHER PUBLICATIONS

Jones et al., "A deimmunised form of the ribotoxin, α-sarcin, lacking CD4+ T cell epitopes and its use as an immunotoxin warhead", Protein Engineering, Design and Selection Advance Access, 2016, pp. 1-10.

Gehlsen et al., "Abstract 655: The next generation of targeted toxins: A novel deimmunized sarcin ribotoxin fused with an EphA2 Abdurin binder", Cancer Research Proceedings: AACR 106th Annual Meeting 2015, Apr. 18-22, 2015, Philadelphia, PA, Aug. 2015, vol. 75, No. 15 (suppl), 2 pages.

* cited by examiner

SEQUENCE LISTING

<160> NUMBER OF SEQ ID NOS: 58

<210> SEQ ID NO 1
<211> LENGTH: 150
<212> TYPE: PRT
<213> ORGANISM: Aspergillus sp.

<400> SEQUENCE: 1

Ala Val Thr Trp Thr Cys Leu Asn Asp Gln Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Glu Asn Gln Gly Glu
    130                 135                 140

Leu Lys Leu Cys Ser His
145                 150

<210> SEQ ID NO 2
<211> LENGTH: 9
<212> TYPE: PRT
<213> ORGANISM: Aspergillus sp.

<400> SEQUENCE: 2

Leu Tyr Asn Gln Asn Lys Ala Glu Ser
1               5

<210> SEQ ID NO 3
<211> LENGTH: 9
<212> TYPE: PRT
<213> ORGANISM: Aspergillus sp.

<400> SEQUENCE: 3

Val Ile Tyr Thr Tyr Pro Asn Lys Val
1               5

<210> SEQ ID NO 4
<211> LENGTH: 9
<212> TYPE: PRT
<213> ORGANISM: Aspergillus sp.

<400> SEQUENCE: 4

Ile Ile Ala His Thr Lys Glu Asn Gln
1               5

<210> SEQ ID NO 5
<211> LENGTH: 9
<212> TYPE: PRT
<213> ORGANISM: Aspergillus sp.

```
<400> SEQUENCE: 5

Gln Lys Asn Pro Lys Thr Asn Lys Tyr
1               5

<210> SEQ ID NO 6
<211> LENGTH: 10
<212> TYPE: PRT
<213> ORGANISM: Aspergillus sp.

<400> SEQUENCE: 6

Asp Gln Lys Asn Pro Lys Thr Asn Lys Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Ala or Thr
<220> FEATURE:
<221> NAME/KEY: MOD_RES
<222> LOCATION: (2)..(2)
<223> OTHER INFORMATION: Gln, Lys, Arg or Ala
<220> FEATURE:
<221> NAME/KEY: MOD_RES
<222> LOCATION: (5)..(5)
<223> OTHER INFORMATION: Pro or Ile
<220> FEATURE:
<221> NAME/KEY: MOD_RES
<222> LOCATION: (7)..(7)
<223> OTHER INFORMATION: Thr, Gly, Gln or His
<220> FEATURE:
<221> NAME/KEY: MOD_RES
<222> LOCATION: (8)..(8)
<223> OTHER INFORMATION: Asn, Arg, Lys or Ala
<220> FEATURE:
<221> NAME/KEY: MOD_RES
<222> LOCATION: (10)..(10)
<223> OTHER INFORMATION: Tyr, His, Lys or Arg

<400> SEQUENCE: 7

Xaa Xaa Lys Asn Xaa Lys Xaa Xaa Lys Xaa
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Lys, Arg or Ala
<220> FEATURE:
<221> NAME/KEY: MOD_RES
<222> LOCATION: (2)..(2)
<223> OTHER INFORMATION: Lys or Leu
<220> FEATURE:
<221> NAME/KEY: MOD_RES
<222> LOCATION: (4)..(4)
<223> OTHER INFORMATION: Pro or Ile
<220> FEATURE:
<221> NAME/KEY: MOD_RES
<222> LOCATION: (6)..(6)
<223> OTHER INFORMATION: Thr, Gly, Gln or His
<220> FEATURE:
```

-continued

```
<221> NAME/KEY: MOD_RES
<222> LOCATION: (7)..(7)
<223> OTHER INFORMATION: Asn, Arg, Lys or Ala
<220> FEATURE:
<221> NAME/KEY: MOD_RES
<222> LOCATION: (9)..(9)
<223> OTHER INFORMATION: Tyr, His, Lys, Arg or Trp

<400> SEQUENCE: 8

Xaa Xaa Asn Xaa Lys Xaa Xaa Lys Xaa
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Ala or Thr
<220> FEATURE:
<221> NAME/KEY: MOD_RES
<222> LOCATION: (2)..(2)
<223> OTHER INFORMATION: Gln, Lys Arg or Ala
<220> FEATURE:
<221> NAME/KEY: MOD_RES
<222> LOCATION: (3)..(3)
<223> OTHER INFORMATION: Lys or Leu
<220> FEATURE:
<221> NAME/KEY: MOD_RES
<222> LOCATION: (5)..(5)
<223> OTHER INFORMATION: Pro or Ile
<220> FEATURE:
<221> NAME/KEY: MOD_RES
<222> LOCATION: (7)..(7)
<223> OTHER INFORMATION: Thr, Gly, Gln or His
<220> FEATURE:
<221> NAME/KEY: MOD_RES
<222> LOCATION: (8)..(8)
<223> OTHER INFORMATION: Asn, Arg, Lys or Ala
<220> FEATURE:
<221> NAME/KEY: MOD_RES
<222> LOCATION: (10)..(10)
<223> OTHER INFORMATION: Tyr, His, Lys, Arg or Trp

<400> SEQUENCE: 9

Xaa Xaa Xaa Asn Xaa Lys Xaa Xaa Lys Xaa
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Ala
<220> FEATURE:
<221> NAME/KEY: MOD_RES
<222> LOCATION: (6)..(6)
<223> OTHER INFORMATION: Lys, Asp, Glu, Gly, Gln, His or Asn
<220> FEATURE:
<221> NAME/KEY: MOD_RES
<222> LOCATION: (7)..(7)
<223> OTHER INFORMATION: Glu or Asp
<220> FEATURE:
<221> NAME/KEY: MOD_RES
<222> LOCATION: (9)..(9)
<223> OTHER INFORMATION: Gln, Asp, Asn, Thr, Glu, Arg or Gly
```

<400> SEQUENCE: 10

Xaa Ile Ala His Thr Xaa Xaa Asn Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Ala
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (5)..(5)
<223> OTHER INFORMATION: Thr or Gln
<220> FEATURE:
<221> NAME/KEY: MOD_RES
<222> LOCATION: (6)..(6)
<223> OTHER INFORMATION: Lys, Asp, Glu, Gly, Gln, His or Asn
<220> FEATURE:
<221> NAME/KEY: MOD_RES
<222> LOCATION: (7)..(7)
<223> OTHER INFORMATION: Glu or Asp
<220> FEATURE:
<221> NAME/KEY: MOD_RES
<222> LOCATION: (9)..(9)
<223> OTHER INFORMATION: Gln, Asp, Asn, Thr, Glu, Arg or Gly

<400> SEQUENCE: 11

Xaa Xaa Ala His Xaa Xaa Xaa Asn Xaa
1               5

<210> SEQ ID NO 12
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid except Asp
<220> FEATURE:
<221> NAME/KEY: MOD_RES
<222> LOCATION: (10)..(10)
<223> OTHER INFORMATION: Any amino acid except Gln
<220> FEATURE:
<221> NAME/KEY: MOD_RES
<222> LOCATION: (13)..(13)
<223> OTHER INFORMATION: Any amino acid except Pro
<220> FEATURE:
<221> NAME/KEY: MOD_RES
<222> LOCATION: (15)..(15)
<223> OTHER INFORMATION: Any amino acid except Thr
<220> FEATURE:
<221> NAME/KEY: MOD_RES
<222> LOCATION: (16)..(16)
<223> OTHER INFORMATION: Any amino acid except Asn
<220> FEATURE:
<221> NAME/KEY: MOD_RES
<222> LOCATION: (18)..(18)
<223> OTHER INFORMATION: Any amino acid except Tyr
<220> FEATURE:
<221> NAME/KEY: MOD_RES
<222> LOCATION: (134)..(134)

```
<223> OTHER INFORMATION: Any amino acid except Ile
<220> FEATURE:
<221> NAME/KEY: MOD_RES
<222> LOCATION: (139)..(139)
<223> OTHER INFORMATION: Any amino acid except Lys
<220> FEATURE:
<221> NAME/KEY: MOD_RES
<222> LOCATION: (140)..(140)
<223> OTHER INFORMATION: Any amino acid except Glu
<220> FEATURE:
<221> NAME/KEY: MOD_RES
<222> LOCATION: (142)..(142)
<223> OTHER INFORMATION: Any amino acid except Gln

<400> SEQUENCE: 12

Ala Val Thr Trp Thr Cys Leu Asn Xaa Xaa Lys Asn Xaa Lys Xaa Xaa
1               5                   10                  15

Lys Xaa Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Xaa Ile Ala His Thr Xaa Xaa Asn Xaa Gly Glu
    130                 135                 140

Leu Lys Leu Cys Ser His
145                 150

<210> SEQ ID NO 13
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Asp, Ala or Thr
<220> FEATURE:
<221> NAME/KEY: MOD_RES
<222> LOCATION: (10)..(10)
<223> OTHER INFORMATION: Gln, Lys, Arg or Ala
<220> FEATURE:
<221> NAME/KEY: MOD_RES
<222> LOCATION: (13)..(13)
<223> OTHER INFORMATION: Pro or Ile
<220> FEATURE:
<221> NAME/KEY: MOD_RES
<222> LOCATION: (15)..(15)
<223> OTHER INFORMATION: Thr, Gly, Gln or His
<220> FEATURE:
<221> NAME/KEY: MOD_RES
<222> LOCATION: (16)..(16)
<223> OTHER INFORMATION: Asn, Arg, Lys or Ala
<220> FEATURE:
<221> NAME/KEY: MOD_RES
<222> LOCATION: (18)..(18)
<223> OTHER INFORMATION: Tyr, His, Lys or Arg
<220> FEATURE:
```

```
<221> NAME/KEY: MOD_RES
<222> LOCATION: (134)..(134)
<223> OTHER INFORMATION: Ile or Ala
<220> FEATURE:
<221> NAME/KEY: MOD_RES
<222> LOCATION: (139)..(139)
<223> OTHER INFORMATION: Lys, Asp, Glu, Gly, Gln, His or Asn
<220> FEATURE:
<221> NAME/KEY: MOD_RES
<222> LOCATION: (140)..(140)
<223> OTHER INFORMATION: Glu or Asp
<220> FEATURE:
<221> NAME/KEY: MOD_RES
<222> LOCATION: (142)..(142)
<223> OTHER INFORMATION: Gln, Asp, Asn, Thr, Glu, Arg or Gly

<400> SEQUENCE: 13

Ala Val Thr Trp Thr Cys Leu Asn Xaa Xaa Lys Asn Xaa Lys Xaa Xaa
1               5                   10                  15

Lys Xaa Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Xaa Ile Ala His Thr Xaa Xaa Asn Xaa Gly Glu
    130                 135                 140

Leu Lys Leu Cys Ser His
145                 150

<210> SEQ ID NO 14
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Lys or Ala

<400> SEQUENCE: 14

Ala Val Thr Trp Thr Cys Leu Asn Asp Xaa Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
```

```
                    85                  90                  95
Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Gln Gly Glu
        130                 135                 140

Leu Lys Leu Cys Ser His
145                 150

<210> SEQ ID NO 15
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Arg, Lys or Ala

<400> SEQUENCE: 15

Ala Val Thr Trp Thr Cys Leu Asn Asp Gln Lys Asn Pro Lys Thr Xaa
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Gln Gly Glu
        130                 135                 140

Leu Lys Leu Cys Ser His
145                 150

<210> SEQ ID NO 16
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Lys or Arg

<400> SEQUENCE: 16

Ala Val Thr Trp Thr Cys Leu Asn Asp Gln Lys Asn Pro Lys Thr Asn
1               5                   10                  15

Lys Xaa Glu Thr Lys Arg Leu Leu Tyr Asn Gln Asn Lys Ala Glu Ser
            20                  25                  30
```

```
Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
 50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Gln Gly Glu
        130                 135                 140

Leu Lys Leu Cys Ser His
145                 150
```

<210> SEQ ID NO 17
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Asp or Glu

<400> SEQUENCE: 17

```
Ala Val Thr Trp Thr Cys Leu Asn Asp Gln Lys Asn Pro Lys Thr Asn
 1               5                  10                  15

Lys Tyr Glu Thr Lys Arg Leu Leu Tyr Asn Gln Asn Lys Ala Glu Ser
                 20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
 50                  55                  60

Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Xaa Glu Asn Gln Gly Glu
        130                 135                 140

Leu Lys Leu Cys Ser His
145                 150
```

<210> SEQ ID NO 18
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Ala Val Thr Trp Thr Cys Leu Asn Asp Gln Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Asp Asn Gln Gly Glu
130                 135                 140

Leu Lys Leu Cys Ser His
145                 150
```

<210> SEQ ID NO 19
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (142)..(142)
<223> OTHER INFORMATION: Asn, Thr or Glu

<400> SEQUENCE: 19

```
Ala Val Thr Trp Thr Cys Leu Asn Asp Gln Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Lys Glu Asn Xaa Gly Glu
130                 135                 140

Leu Lys Leu Cys Ser His
145                 150
```

<210> SEQ ID NO 20

```
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Asp or Glu

<400> SEQUENCE: 20

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
        115                 120                 125

Lys Val Phe Cys Gly Ile Ile Ala His Thr Xaa Glu Asn Gln Gly Glu
    130                 135                 140

Leu Lys Leu Cys Ser His
145                 150

<210> SEQ ID NO 21
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Asp or Glu

<400> SEQUENCE: 21

Ala Val Thr Trp Thr Cys Leu Asn Asp Gln Lys Asn Pro Lys Thr Arg
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110
```

```
Pro Lys Glu Asn Pro Gly Pro Ala Arg Val Ile Tyr Thr Tyr Pro Asn
            115                 120                 125

Lys Val Phe Cys Gly Ile Ile Ala His Thr Xaa Glu Asn Gln Gly Glu
    130                 135                 140

Leu Lys Leu Cys Ser His
145                 150

<210> SEQ ID NO 22
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Lys or Arg
<220> FEATURE:
<221> NAME/KEY: MOD_RES
<222> LOCATION: (139)..(139)
<223> OTHER INFORMATION: Asp or Glu

<400> SEQUENCE: 22

Ala Val Thr Trp Thr Cys Leu Asn Asp Gln Lys Asn Pro Lys Thr Asn
1               5                   10                  15

Lys Xaa Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
            100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Xaa Glu Asn Gln Gly Glu
    130                 135                 140

Leu Lys Leu Cys Ser His
145                 150

<210> SEQ ID NO 23
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
            20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
```

```
            50                  55                  60
Gly Arg Thr Pro Ile Lys Phe Gly Lys Ser Asp Cys Asp Arg Pro Pro
 65                  70                  75                  80

Lys His Ser Lys Asp Gly Asn Gly Lys Thr Asp His Tyr Leu Leu Glu
                 85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Lys Glu Asn Thr Gly Glu
        130                 135                 140

Leu Lys Leu Cys Ser His
145                 150

<210> SEQ ID NO 24
<211> LENGTH: 150
<212> TYPE: PRT
<213> ORGANISM: Aspergillus sp.

<400> SEQUENCE: 24

Ala Ala Thr Trp Thr Cys Met Asn Glu Gln Lys Asn Pro Lys Thr Asn
  1               5                  10                  15

Lys Tyr Glu Asn Lys Arg Leu Leu Tyr Asn Gln Asn Asn Ala Glu Ser
                 20                  25                  30

Asn Ala His His Ala Pro Leu Ser Asp Gly Lys Thr Gly Ser Ser Tyr
             35                  40                  45

Pro His Trp Phe Thr Asn Gly Tyr Asp Gly Asp Gly Lys Ile Leu Lys
         50                  55                  60

Gly Arg Thr Pro Ile Lys Trp Gly Asn Ser Asp Cys Asp Arg Pro Pro
 65                  70                  75                  80

Lys His Ser Lys Asn Gly Asp Gly Lys Asn Asp His Tyr Leu Leu Glu
                 85                  90                  95

Phe Pro Thr Phe Pro Asp Gly His Gln Tyr Asn Phe Asp Ser Lys Lys
                100                 105                 110

Pro Lys Glu Asp Pro Gly Pro Ala Arg Val Ile Tyr Thr Tyr Pro Asn
            115                 120                 125

Lys Val Phe Cys Gly Ile Val Ala His Thr Arg Glu Asn Gln Gly Asp
        130                 135                 140

Leu Lys Leu Cys Ser His
145                 150

<210> SEQ ID NO 25
<211> LENGTH: 150
<212> TYPE: PRT
<213> ORGANISM: Aspergillus sp.

<400> SEQUENCE: 25

Ala Val Thr Trp Thr Cys Leu Asn Glu Gln Lys Asn Ile Lys Thr Asn
  1               5                  10                  15

Lys Tyr Glu Thr Lys Arg Leu Leu Tyr Asn Gln Asp Lys Ala Glu Ser
                 20                  25                  30

Asn Ser His His Ala Pro Leu Ser Asp Gly Lys Thr Gly Ser Ser Tyr
             35                  40                  45

Pro His Trp Phe Thr Asn Gly Tyr Asp Gly Glu Gly Lys Ile Leu Lys
         50                  55                  60

Gly Arg Thr Pro Ile Lys Phe Gly Lys Ser Asp Cys Asp Arg Pro Pro
```

```
                65                  70                  75                  80
Lys His Ser Lys Asp Gly Asn Gly Lys Asn Asp His Tyr Leu Leu Glu
                    85                  90                  95
Phe Pro Thr Phe Pro Asp Gly His Asp Tyr Lys Phe Asp Ser Lys Lys
                100                 105                 110
Pro Lys Glu Asp Pro Gly Pro Ala Arg Val Ile Tyr Thr Tyr Pro Asn
            115                 120                 125
Lys Val Phe Cys Gly Ile Ile Ala His Thr Arg Glu Asn Gln Gly Glu
        130                 135                 140
Leu Lys Leu Cys Ser His
145                 150

<210> SEQ ID NO 26
<211> LENGTH: 149
<212> TYPE: PRT
<213> ORGANISM: Aspergillus sp.

<400> SEQUENCE: 26

Ala Thr Trp Thr Cys Ile Asn Gln Gln Leu Asn Pro Lys Thr Asn Lys
1               5                   10                  15
Trp Glu Asp Lys Arg Leu Leu Tyr Ser Gln Ala Lys Ala Glu Ser Asn
                20                  25                  30
Ser His His Ala Pro Leu Ser Asp Gly Lys Thr Gly Ser Ser Tyr Pro
            35                  40                  45
His Trp Phe Thr Asn Gly Tyr Asp Gly Asn Gly Lys Leu Ile Lys Gly
        50                  55                  60
Arg Thr Pro Ile Lys Phe Gly Lys Ala Asp Cys Asp Arg Pro Pro Lys
65                  70                  75                  80
His Ser Gln Asn Gly Met Gly Lys Asp His Tyr Leu Leu Glu Phe
                85                  90                  95
Pro Thr Phe Pro Asp Gly His Asp Tyr Lys Phe Asp Ser Lys Lys Pro
                100                 105                 110
Lys Glu Asp Pro Gly Pro Ala Arg Val Ile Tyr Thr Tyr Pro Asn Lys
            115                 120                 125
Val Phe Cys Gly Ile Val Ala His Gln Arg Gly Asn Gln Gly Asp Leu
        130                 135                 140
Arg Leu Cys Ser His
145

<210> SEQ ID NO 27
<211> LENGTH: 9
<212> TYPE: PRT
<213> ORGANISM: Aspergillus sp.

<400> SEQUENCE: 27

Ile Val Ala His Thr Arg Glu Asn Gln
1               5

<210> SEQ ID NO 28
<211> LENGTH: 9
<212> TYPE: PRT
<213> ORGANISM: Aspergillus sp.

<400> SEQUENCE: 28

Leu Lys Gly Arg Thr Pro Ile Lys Trp
1               5

<210> SEQ ID NO 29
```

```
<211> LENGTH: 9
<212> TYPE: PRT
<213> ORGANISM: Aspergillus sp.

<400> SEQUENCE: 29

Val Phe Cys Gly Ile Val Ala His Thr
1               5

<210> SEQ ID NO 30
<211> LENGTH: 9
<212> TYPE: PRT
<213> ORGANISM: Aspergillus sp.

<400> SEQUENCE: 30

Leu Lys Gly Arg Thr Pro Ile Lys Phe
1               5

<210> SEQ ID NO 31
<211> LENGTH: 9
<212> TYPE: PRT
<213> ORGANISM: Aspergillus sp.

<400> SEQUENCE: 31

Gln Lys Asn Ile Lys Thr Asn Lys Tyr
1               5

<210> SEQ ID NO 32
<211> LENGTH: 9
<212> TYPE: PRT
<213> ORGANISM: Aspergillus sp.

<400> SEQUENCE: 32

Ile Ile Ala His Thr Arg Glu Asn Gln
1               5

<210> SEQ ID NO 33
<211> LENGTH: 9
<212> TYPE: PRT
<213> ORGANISM: Aspergillus sp.

<400> SEQUENCE: 33

Ile Lys Gly Arg Thr Pro Ile Lys Phe
1               5

<210> SEQ ID NO 34
<211> LENGTH: 9
<212> TYPE: PRT
<213> ORGANISM: Aspergillus sp.

<400> SEQUENCE: 34

Val Phe Cys Gly Ile Val Ala His Gln
1               5

<210> SEQ ID NO 35
<211> LENGTH: 9
<212> TYPE: PRT
<213> ORGANISM: Aspergillus sp.

<400> SEQUENCE: 35

Ile Val Ala His Gln Arg Gly Asn Gln
1               5

<210> SEQ ID NO 36
<211> LENGTH: 9
<212> TYPE: PRT
```

```
<213> ORGANISM: Aspergillus sp.

<400> SEQUENCE: 36

Gln Leu Asn Pro Lys Thr Asn Lys Trp
1               5

<210> SEQ ID NO 37
<211> LENGTH: 15
<212> TYPE: PRT
<213> ORGANISM: Aspergillus sp.

<400> SEQUENCE: 37

Trp Thr Cys Leu Asn Asp Gln Lys Asn Pro Lys Thr Asn Lys Tyr
1               5                   10                  15

<210> SEQ ID NO 38
<211> LENGTH: 15
<212> TYPE: PRT
<213> ORGANISM: Aspergillus sp.

<400> SEQUENCE: 38

Leu Asn Asp Gln Lys Asn Pro Lys Thr Asn Lys Tyr Glu Thr Lys
1               5                   10                  15

<210> SEQ ID NO 39
<211> LENGTH: 15
<212> TYPE: PRT
<213> ORGANISM: Aspergillus sp.

<400> SEQUENCE: 39

Gln Lys Asn Pro Lys Thr Asn Lys Tyr Glu Thr Lys Arg Leu Leu
1               5                   10                  15

<210> SEQ ID NO 40
<211> LENGTH: 15
<212> TYPE: PRT
<213> ORGANISM: Aspergillus sp.

<400> SEQUENCE: 40

Val Phe Cys Gly Ile Ile Ala His Thr Lys Glu Asn Gln Gly Glu
1               5                   10                  15

<210> SEQ ID NO 41
<211> LENGTH: 15
<212> TYPE: PRT
<213> ORGANISM: Aspergillus sp.

<400> SEQUENCE: 41

Gly Ile Ile Ala His Thr Lys Glu Asn Gln Gly Glu Leu Lys Leu
1               5                   10                  15

<210> SEQ ID NO 42
<211> LENGTH: 15
<212> TYPE: PRT
<213> ORGANISM: Aspergillus sp.

<400> SEQUENCE: 42

Val Phe Cys Gly Ile Ile Ala Gln Thr Lys Glu Asn Gln Gly Glu
1               5                   10                  15

<210> SEQ ID NO 43
<211> LENGTH: 15
<212> TYPE: PRT
<213> ORGANISM: Aspergillus sp.
```

```
<400> SEQUENCE: 43

Gly Ile Ile Ala Gln Thr Lys Glu Asn Gln Gly Glu Leu Lys Leu
1               5                   10                  15

<210> SEQ ID NO 44
<211> LENGTH: 10
<212> TYPE: PRT
<213> ORGANISM: Aspergillus sp.
<220> FEATURE:
<221> NAME/KEY: misc_feature
<222> LOCATION: (1)..(2)
<223> OTHER INFORMATION: This region may encompass "Gln" or "Asp-Gln"
      wherein some positions may be absent

<400> SEQUENCE: 44

Asp Gln Lys Asn Pro Lys Thr Asn Lys Tyr
1               5                   10

<210> SEQ ID NO 45
<211> LENGTH: 149
<212> TYPE: PRT
<213> ORGANISM: Aspergillus sp.

<400> SEQUENCE: 45

Ala Thr Trp Thr Cys Ile Asn Gln Gln Leu Asn Pro Lys Thr Asn Lys
1               5                   10                  15

Trp Glu Asp Lys Arg Leu Leu Tyr Ser Gln Ala Lys Ala Glu Ser Asn
                20                  25                  30

Ser His His Ala Pro Leu Ser Asp Gly Lys Thr Gly Ser Ser Tyr Pro
            35                  40                  45

His Trp Phe Thr Asn Gly Tyr Asp Gly Asn Gly Lys Leu Ile Lys Gly
        50                  55                  60

Arg Thr Pro Ile Lys Phe Gly Lys Ala Asp Cys Asp Arg Pro Lys
65                  70                  75                  80

His Ser Gln Asn Gly Met Gly Lys Asp His Tyr Leu Leu Glu Phe
                85                  90                  95

Pro Thr Phe Pro Asp Gly His Asp Tyr Lys Phe Asp Ser Lys Lys Pro
            100                 105                 110

Lys Glu Asn Pro Gly Pro Ala Arg Val Ile Tyr Thr Tyr Pro Asn Lys
        115                 120                 125

Val Phe Cys Gly Ile Val Ala His Gln Arg Gly Asn Gln Gly Asp Leu
    130                 135                 140

Arg Leu Cys Ser His
145

<210> SEQ ID NO 46
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
            35                  40                  45
```

```
Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Asp Glu Asn Thr Gly Glu
            130                 135                 140

Leu Lys Leu Cys Ser His
145                 150

<210> SEQ ID NO 47
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Val Thr Trp Thr Cys Leu Asn Asp Lys Lys Asn Pro Lys Thr Asn
1               5                   10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
                35                  40                  45

Pro His Trp Phe Thr Asn Gly Tyr Asp Gly Asp Gly Lys Leu Pro Lys
    50                  55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Glu Glu Asn Thr Gly Glu
            130                 135                 140

Leu Lys Leu Cys Ser His
145                 150

<210> SEQ ID NO 48
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Val Thr Trp Thr Cys Leu Asn Asp Gln Lys Asn Pro Lys Thr Arg
1               5                   10                  15

Lys Tyr Glu Thr Lys Arg Leu Leu Tyr Asn Gln Asn Lys Ala Glu Ser
                20                  25                  30
```

```
Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
50                      55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Asp Glu Asn Thr Gly Glu
130                 135                 140

Leu Lys Leu Cys Ser His
145                 150

<210> SEQ ID NO 49
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Val Thr Trp Thr Cys Leu Asn Asp Gln Lys Asn Pro Lys Thr Arg
1               5                   10                  15

Lys Tyr Glu Thr Lys Arg Leu Leu Tyr Asn Gln Asn Lys Ala Glu Ser
                20                  25                  30

Asn Ser His His Ala Pro Leu Ser Asp Gly Lys Thr Gly Ser Ser Tyr
        35                  40                  45

Pro His Trp Phe Thr Asn Gly Tyr Asp Gly Asp Gly Lys Leu Pro Lys
50                      55                  60

Gly Arg Thr Pro Ile Lys Phe Gly Lys Ser Asp Cys Asp Arg Pro Pro
65                  70                  75                  80

Lys His Ser Lys Asp Gly Asn Gly Lys Thr Asp His Tyr Leu Leu Glu
                85                  90                  95

Phe Pro Thr Phe Pro Asp Gly His Asp Tyr Lys Phe Asp Ser Lys Lys
                100                 105                 110

Pro Lys Glu Asn Pro Gly Pro Ala Arg Val Ile Tyr Thr Tyr Pro Asn
            115                 120                 125

Lys Val Phe Cys Gly Ile Ile Ala His Thr Glu Glu Asn Thr Gly Glu
130                 135                 140

Leu Lys Leu Cys Ser His
145                 150

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 50

His His His His His His
1               5
```

<210> SEQ ID NO 51
<211> LENGTH: 15
<212> TYPE: PRT
<213> ORGANISM: Aspergillus sp.

<400> SEQUENCE: 51

Trp Thr Cys Leu Asn Asp Gln Lys Asn Pro Lys Thr Asn Lys Tyr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp, Ala or Thr
<220> FEATURE:
<221> NAME/KEY: MOD_RES
<222> LOCATION: (7)..(7)
<223> OTHER INFORMATION: Gln, Lys, Arg or Ala
<220> FEATURE:
<221> NAME/KEY: MOD_RES
<222> LOCATION: (10)..(10)
<223> OTHER INFORMATION: Pro or Ile
<220> FEATURE:
<221> NAME/KEY: MOD_RES
<222> LOCATION: (12)..(12)
<223> OTHER INFORMATION: Thr, Gly, Gln or His
<220> FEATURE:
<221> NAME/KEY: MOD_RES
<222> LOCATION: (13)..(13)
<223> OTHER INFORMATION: Asn, Arg, Lys or Ala
<220> FEATURE:
<221> NAME/KEY: MOD_RES
<222> LOCATION: (15)..(15)
<223> OTHER INFORMATION: Tyr, His, Lys or Arg

<400> SEQUENCE: 52

Trp Thr Cys Leu Asn Xaa Xaa Lys Asn Xaa Lys Xaa Xaa Lys Xaa
1               5                   10                  15

<210> SEQ ID NO 53
<211> LENGTH: 15
<212> TYPE: PRT
<213> ORGANISM: Aspergillus sp.

<400> SEQUENCE: 53

Leu Asn Asp Gln Lys Asn Pro Lys Thr Asn Lys Tyr Glu Thr Lys
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Ala or Thr
<220> FEATURE:
<221> NAME/KEY: MOD_RES
<222> LOCATION: (4)..(4)
<223> OTHER INFORMATION: Gln, Lys, Arg or Ala
<220> FEATURE:
<221> NAME/KEY: MOD_RES
<222> LOCATION: (7)..(7)

```
<223> OTHER INFORMATION: Pro or Ile
<220> FEATURE:
<221> NAME/KEY: MOD_RES
<222> LOCATION: (9)..(9)
<223> OTHER INFORMATION: Thr, Gly, Gln or His
<220> FEATURE:
<221> NAME/KEY: MOD_RES
<222> LOCATION: (10)..(10)
<223> OTHER INFORMATION: Asn, Arg, Lys or Ala
<220> FEATURE:
<221> NAME/KEY: MOD_RES
<222> LOCATION: (12)..(12)
<223> OTHER INFORMATION: Tyr, His, Lys or Arg

<400> SEQUENCE: 54

Leu Asn Xaa Xaa Lys Asn Xaa Lys Xaa Xaa Lys Xaa Glu Thr Lys
1               5                   10                  15

<210> SEQ ID NO 55
<211> LENGTH: 15
<212> TYPE: PRT
<213> ORGANISM: Aspergillus sp.

<400> SEQUENCE: 55

Val Phe Cys Gly Ile Ile Ala His Thr Lys Glu Asn Gln Gly Glu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ile or Ala
<220> FEATURE:
<221> NAME/KEY: MOD_RES
<222> LOCATION: (10)..(10)
<223> OTHER INFORMATION: Lys, Asp, Glu, Gly, Gln, His or Asn
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (13)..(13)
<223> OTHER INFORMATION: Gln, Asp, Asn, Thr, Glu, Arg or Gly

<400> SEQUENCE: 56

Val Phe Cys Gly Xaa Ile Ala His Thr Xaa Xaa Asn Xaa Gly Glu
1               5                   10                  15

<210> SEQ ID NO 57
<211> LENGTH: 15
<212> TYPE: PRT
<213> ORGANISM: Aspergillus sp.

<400> SEQUENCE: 57

Gly Ile Ile Ala His Thr Lys Glu Asn Gln Gly Glu Leu Lys Leu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Ile or Ala
<220> FEATURE:
<221> NAME/KEY: MOD_RES
<222> LOCATION: (7)..(7)
<223> OTHER INFORMATION: Lys, Asp, Glu, Gly, Gln, His or Asn
<220> FEATURE:
<221> NAME/KEY: MOD_RES
<222> LOCATION: (8)..(8)
<223> OTHER INFORMATION: Glu or Asp
<220> FEATURE:
<221> NAME/KEY: MOD_RES
<222> LOCATION: (10)..(10)
<223> OTHER INFORMATION: Gln, Asp, Asn, Thr, Glu, Arg or Gly

<400> SEQUENCE: 58

Gly Xaa Ile Ala His Thr Xaa Xaa Asn Xaa Gly Glu Leu Lys Leu
1               5                   10                  15
```

RIBOTOXIN MOLECULES DERIVED FROM SARCIN AND OTHER RELATED FUNGAL RIBOTOXINS

CROSS REFERENCE TO RELATED APPLICATIONS

This application is a continuation of U.S. application Ser. No. 14/774,445, filed 10 Sep. 2015 (now U.S. Pat. No. 9,603,911), which is the U.S. National Stage application of PCT/US2014/020035, filed 3 Mar. 2014, which claims the benefit of, and relies on the filing date of, U.S. provisional patent application No. 61/902,972, filed 12 Nov. 2013, and U.S. provisional patent application No. 61/783,589, filed 14 Mar. 2013, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Feb. 22, 2016, is named 0185_0001_Corrected_Sequence_Listing_2-22-16.txt and is 42 kilobytes in size.

BACKGROUND

α-Sarcin was one of the first ribotoxins to be discovered as a product of the mold *Aspergillus giganteum* MDH18894 in 1965. It was named because of its toxicity to certain sarcoma cell lines. This toxicity was determined later in the mid-1970s to be due to specific cleavage by the toxin of a certain segment of ribosomal RNA (the sarcin-ricin loop) conserved throughout the animal kingdom. Cleavage of that ribosomal RNA by the toxin inhibits protein production by the cell. It is highly toxic, killing cells through an apoptotic mechanism.

α-Sarcin is a 150 amino acid protein (Lacadena et al., 2007, FEMS Microbiol Rev 31, 212-237). Much is known about the structure of α-sarcin. Tyr48, His50, Glu96, Arg121, His137 and Leu145 are critical amino acids for the active site of the RNAse activity. The five-stranded beta sheet and single α-helix are important for the molecule's 3D structure. The protein contains two disulfide bonds. Most of the natural variation between α-sarcin and molecules from related organisms resides in the loops between these structural elements. Deletion of amino acids 7-22 does not appear to affect the protein's conformation. (It did however affect membrane interaction.) The molecule is highly negatively charged with a high isoelectric point. Amino acids 116-139 may be involved in cell membrane interactions, such as crossing of the cell membrane. Asn54 may be involved in the binding pocket for the substrate. Arg121 may be critical for interaction with lipid membranes. The immunogenicity of sarcin has not been well studied.

Other fungal ribotoxins belong to the same family as α-sarcin and are produced by other *Aspergillus* species, including, for example, clavin, gigantin, mitogillin, and restrictocin The members of this family of ribotoxins share a high degree of amino acid identity, generally greater than 85%. (Lacadena et al., 2007, FEMS Microbiol Rev 31, 212-237) and mediate toxicity through the same mechanism, i.e., by cleaving a phosphodiester bond in the conserved sarcin-ricin loop of ribosomal RNA. Clavin and gigantin are 150 amino acids in length, while restrictocin and mitogillin, which are variants of the same polypeptide isolated from *A. restrictus*, are 149 amino acids in length.

SUMMARY

Briefly, the present disclosure features modified ribotoxin epitopes of the fungal ribotoxins, including α-sarcin, clavin, gigantin, mitogillin, and restrictocin, e.g., "modified ribotoxin epitopes." Without intending to be bound by any theory or mechanism, it is believed that the modified ribotoxin epitopes disclosed in this application possess reduced binding to human MHC class II and/or elicit a reduced T cell response as compared to the corresponding wild type ribotoxin epitopes.

In one exemplary embodiment, the modified T cell epitope comprises one or more amino acid modifications of a wild type T cell epitope having the amino acid sequence of XKNPKTNKY (SEQ ID NO:44), wherein X is Q or DQ. In another exemplary embodiment, the modified T cell epitope comprises one or more amino acid modifications of a wild type T cell epitope having the amino acid sequence of IIAHTKENQ (SEQ ID NO:4).

The present disclosure also features modified molecules based on the structure of the fungal ribotoxins, including α-sarcin, clavin, gigantin, mitogillin, and restrictocin, e.g., "modified ribotoxin molecules." Without intending to be bound by any theory or mechanism, it is believed that the modified ribotoxin molecules of the present invention are less immunogenic to humans as compared to the wild type ribotoxin. A molecule's efficacy may be limited by an unwanted immune response, particularly if the molecule is used in a therapeutic or prophylactic setting. Therefore, it may be desirable in certain instances to reduce the immunogenicity of a molecule.

In one exemplary embodiment, the modified sarcin polypeptide comprises at least one mutation as compared to a wild type α-sarcin polypeptide (SEQ ID NO:1), wherein the at least one mutation is within a first T cell epitope and/or a second T cell epitope of the wild type α-sarcin polypeptide, wherein the first T cell epitope consists of the amino acid sequence XKNPKTNKY (SEQ ID NO:44), wherein X is Q or DQ and the second T cell epitope consists of the amino acid sequence IIAHTKENQ (SEQ ID NO:4).

The present disclosure also features fusion proteins comprising modified ribotoxin molecules (e.g., α-sarcin, clavin, gigantin, mitogillin, and restrictocin) and targeting molecules. Targeting molecules may include but are not limited to antibodies, Fab fragments, single chain variable fragments (scFvs), VH domains, engineered CH2 domains, peptides, cytokines, hormones, other protein scaffolds, etc. The fusion proteins may be used as therapeutic agents. For example, in some embodiments, the fusion proteins target an unwanted pathogen or a cancer cell. Thus, certain embodiments are directed to methods of using a fusion protein comprising a modified ribotoxin molecule to treat or manage a disease or condition.

Another aspect is directed to nucleic acid constructs encoding the modified ribotoxin molecules (e.g., α-sarcin, clavin, gigantin, mitogillin, and restrictocin) or fusion proteins comprising the same. The nucleic acid constructs can be used, for example, in a method of producing the modified ribotoxin molecule or fusion protein by expressing the nucleic acid construct in a host cell and isolating the modified ribotoxin molecule or fusion protein.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

BRIEF DESCRIPTION OF THE FIGURES

The accompanying drawings, which are included to provide a further understanding of the invention and are incorporated in and constitute a part of this specification, illustrate aspects of the invention and together with the description serve to explain the principles of the invention. In the drawings:

FIG. 7A is an anti-His western blot of soluble (S) and insoluble (I) fractions following B-Per extraction. FIG. 7B is a Coomassie Blue-stained SDS-PAGE gel of His-purified variants.

DEFINITIONS

Figure 1:
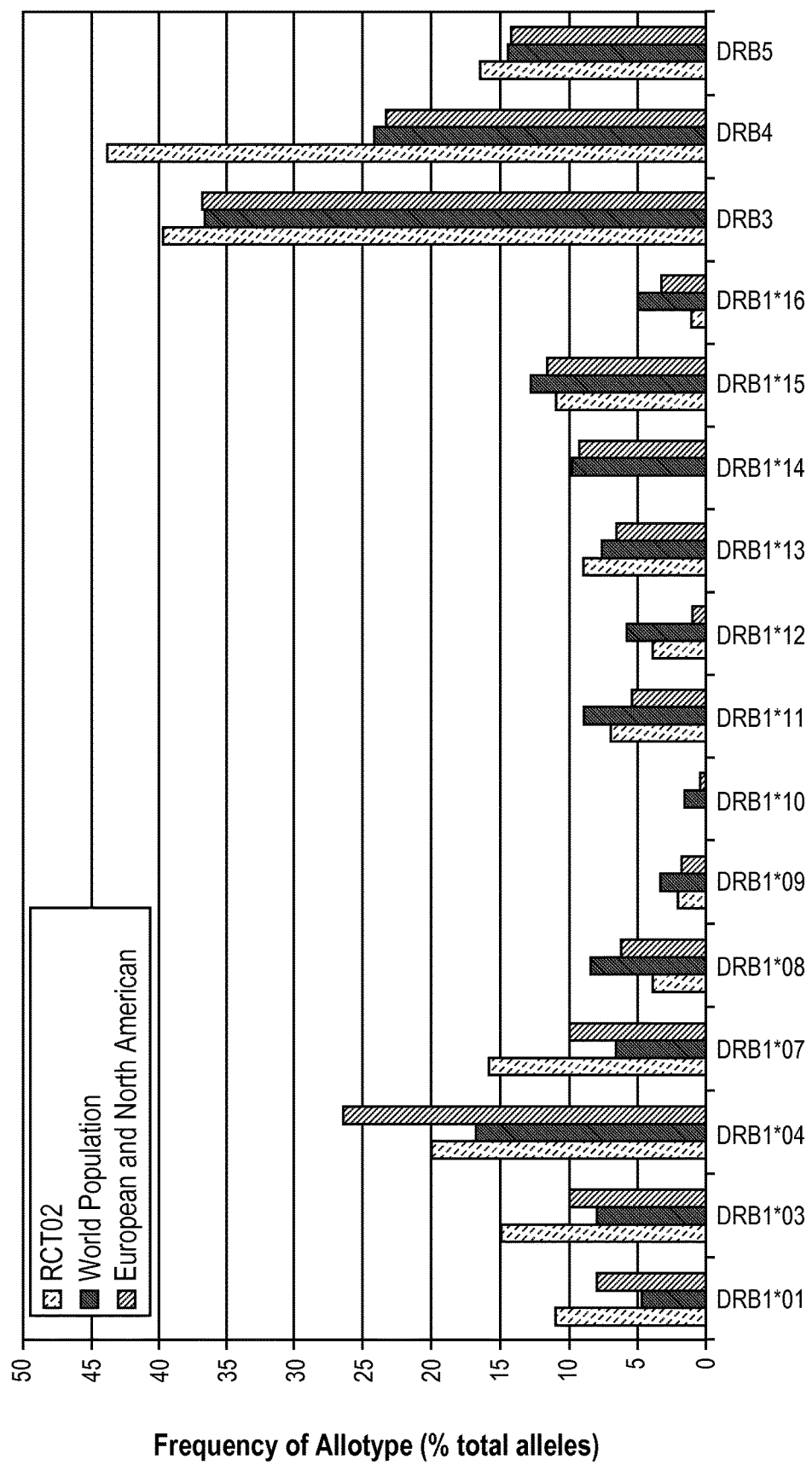
FIG. 1 shows a comparison of the frequency of donor allotypes expressed in the RCT02 study cohort (n=52) and the world, European and North American populations.

In order to facilitate the review of the various embodiments of the invention, the following explanations of specific terms are provided:

Definitions of common terms in molecular biology, cell biology, and immunology may be found in *Kuby Immunology*, Thomas J. Kindt, Richard A. Goldsby, Barbara Anne Osborne, Janis Kuby, published by W.H. Freeman, 2007 (ISBN 1429202114); and *Genes IX*, Benjamin Lewin, published by Jones & Bartlett Publishers, 2007 (ISBN-10: 0763740632).

Antibody: A protein (or complex) that includes one or more polypeptides substantially encoded by immunoglobulin genes or fragments of immunoglobulin genes. The immunoglobulin genes may include the kappa, lambda, alpha, gamma, delta, epsilon, and mu constant region genes, as well as the myriad of immunoglobulin variable region genes. Light chains may be classified as either kappa or lambda. Heavy chains may be classified as gamma, mu, alpha, delta, or epsilon, which in turn define the immunoglobulin classes IgG, IgM, IgA, IgD, and IgE, respectively.

As used herein, the term "antibodies" includes intact immunoglobulins as well as fragments (e.g., having a molecular weight between about 10 kDa to 100 kDa). Antibody fragments may include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with the enzyme pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) scFv, single chain antibody, a genetically engineered molecule containing the variable region of the light chain, the variable region of the heavy chain, linked by a suitable polypeptide linker as a genetically fused single chain molecule. Methods of making antibody fragments are routine (see, for example, Harlow and Lane, *Using Antibodies: A Laboratory Manual*, CSHL, New York, 1999). Antibody fragments are not limited to the aforementioned examples, e.g., an antibody fragment may include a $V_H$, a $V_L$, etc.

Antibodies can be monoclonal or polyclonal. Monoclonal antibodies can be prepared from a variety of methods, e.g., methods involving phage display and human antibody libraries. Examples of procedures for monoclonal antibody production are described in Longberg and Huzar (Int Rev Immunol., 1995, 13:65-93), Kellermann and Green (Curr Opin Biotechnol., 2002, 13:593-7, and Harlow and Lane (*Using Antibodies: A Laboratory Manual*, CSHL, New York, 1999). Classical methods of preparing murine hybridomas are discussed in Kohler and Milstein (*Nature* 256:495-97, 1975).

A standard "humanized" immunoglobulin, such as a humanized antibody, is an immunoglobulin including a human framework region and one or more CDRs from a non-human (e.g., mouse, rat, synthetic, etc.) immunoglobulin. A humanized antibody binds to the same or similar antigen as the donor antibody that provides the CDRs. The molecules can be constructed by means of genetic engineering (see, for example, U.S. Pat. No. 5,585,089).

Antigen: A compound, composition, or substance that can stimulate the production of antibodies or a T cell response, including compositions that are injected or absorbed. An antigen (Ag) reacts with the products of specific humoral or cellular immunity. In some embodiments, an antigen also may be the specific binding target of the modified sarcin molecule and/or ribotoxin fusion protein (e.g., binding moieties) whether or not such interaction could produce an immunological response.

Avidity: binding affinity (e.g., increased) as a result from bivalent or multivalent binding sites that may simultaneously bind to a multivalent target antigen or receptor that is either itself multimeric or is present on the surface of a cell or virus such that it can be organized into a multimeric form. For example, the two Fab arms of an immunoglobulin can provide such avidity increase for an antigen compared with the binding of a single Fab arm, since both sites must be unbound for the immunoglobulin to dissociate.

Binding affinity: The strength of binding between a binding site and a ligand (e.g., between a binding moiety, e.g., an antibody, and an antigen or epitope). The affinity of a binding site X for a ligand Y is represented by the dissociation constant (Kd), which is the concentration of Y that is required to occupy half of the binding sites of X present in a solution. A lower (Kd) indicates a stronger or higher-affinity interaction between X and Y and a lower concentration of ligand is needed to occupy the sites. In general, binding affinity can be affected by the alteration, modification and/or substitution of one or more amino acids in the epitope recognized by the paratope (portion of the molecule that recognizes the epitope). Binding affinity can also be affected by the alteration, modification and/or substitution of one or more amino acids in the paratope. Binding affinity can be the affinity of antibody binding an antigen.

In one example, binding affinity can be measured by end-point titration in an Ag-ELISA assay. Binding affinity can be substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

CH2 or CH3 domain molecule: A polypeptide (or nucleic acid encoding a polypeptide) derived from an immunoglobulin CH2 or CH3 domain. Unless noted otherwise, the immunoglobulin can be IgG, IgA, IgD, IgE or IgM. The CH2 or CH3 molecule is composed of a number of parallel β-strands connected by loops of unstructured amino acid sequence. The CH2 or CH3 domain molecule can further comprise an additional amino acid sequence(s), such as a complete hypervariable loop. In some embodiments, the CH2 or CH3 domains comprise one or more mutations in a loop region of the molecule. In some embodiments, the CH2 or CH3 domains comprise one or more mutations in a scaffold region (e.g., for stabilization, etc.). A "loop region" of a CH2 or CH3 domain refers to the portion of the protein located between regions of β-sheet (for example, each CH2 domain comprises seven β-sheets, A to G, oriented from the N- to C-terminus). A CH2 domain comprises six loop regions: Loop 1, Loop 2, Loop 3, Loop A-B, Loop C-D and Loop E-F. Loops A-B, C-D and E-F are located between β-sheets A and B, C and D, and E and F, respectively. Loops 1, 2 and 3 are located between β-sheets B and C, D and E, and F and G, respectively. These loops in the natural CH2 domain are often referred to as structural loops. Non-limiting examples of CH2 domain molecules can be found in WO 2009/099961.

Naturally occurring CH2 and CH3 domain molecules are small in size, usually less than 15 kD. Engineered CH2 and CH3 domain molecules can vary in size depending on the length of donor loops inserted in the loop regions, how many donor loops are inserted and whether another molecule (such as a binding moiety, an effector molecule, or a label) is conjugated or linked to the CH2 or CH3 domain. The CH2 domain may be from IgG, IgA or IgD. The CH2 domain may be from a CH3 domain from IgE or IgM, which is homologous to the CH2 domains of IgG, IgA or IgD.

CH2D: A CH2 or CH3 domain molecule. The CH2 or CH3 domain molecule may be engineered such that the molecule specifically binds an antigen. The CH2 and CH3 domain molecules engineered to bind antigen are among the smallest known antigen-specific binding antibody domain-based molecules that can retain Fc receptor binding.

Contacting: Placement in direct physical association, which includes both in solid and in liquid form.

Degenerate polynucleotide: As used herein, a "degenerate polynucleotide" is a polynucleotide encoding a protein (e.g., a modified sarcin molecule, a fusion protein) that includes a sequence that is degenerate as a result of redundancies in the genetic code. There are 20 natural amino acids, most of which are specified by more than one codon. Therefore, all degenerate nucleotide sequences are included as long as the amino acid sequence of the protein (e.g., the modified sarcin molecule, fusion protein) encoded by the nucleotide sequence is unchanged.

Preferably, the codons are well expressed in the selected host organism. Use of the degenerate versions of the encoding nucleic acids may optimize expression ("codon optimization") in different expression systems. For example, *E. coli* expression systems may prefer one codon for an amino acid while a *Pichia* protein expression system may prefer a different codon for the same amino acid in that position of the protein.

Domain: A protein structure that retains its tertiary structure independently of the remainder of the protein. In some cases, domains have discrete functional properties and can be added, removed or transferred to another protein without a loss of function.

Effector molecule: A molecule, or the portion of a chimeric molecule, that is intended to have a desired effect on a cell to which the molecule or chimeric molecule is targeted. An effector molecule is also known as an effector moiety (EM), therapeutic agent, or diagnostic agent, or similar terms. Examples of effector molecules include, but are not limited to, a detectable label, biologically active protein, drug, cytotoxic molecule, or toxin (cytotoxic molecule).

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: The translation of a nucleic acid sequence into a protein. Proteins may be expressed and remain intracellular, become a component of the cell surface membrane, or be secreted into the extracellular matrix or medium.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (e.g., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Both constitutive and inducible promoters are included (see, for example, Bitter et al. (1987) Methods in Enzymology 153:516-544).

Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see, for example, Bitter et al. (1987) Methods in Enzymology 153:516-544). For example, when cloning in bacterial systems, inducible promoters such as pL of bacteriophage lambda, plac, ptrp, ptac (ptrp-lac hybrid promoter) and the like may be used. In some embodiments, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5 K promoter, etc.) can be used. Promoters produced by recombinant DNA or synthetic techniques may also be used to provide for transcription of the nucleic acid sequences.

A polynucleotide can be inserted into an expression vector that contains a promoter sequence that facilitates the efficient transcription of the inserted genetic sequence of the host. The expression vector typically contains an origin of replication, a promoter, as well as specific nucleic acid sequences that allow phenotypic selection of the transformed cells.

Expression system: A system for expressing a gene product, e.g., a protein. Expression systems may be cell-based or cell-free. Examples of expression systems include but are not limited to bacterial systems (e.g., *E. coli*, *B. subtilis*), yeast systems (e.g., *Pichia*, *S. cerevisiae*), an insect system, a eukaryotic system, viral systems (e.g., baculovirus, lambda, retrovirus), and the like.

Fc binding regions: The FcRn binding region of the CH2 region is known to comprise the amino acid residues M252, I253, S254, T256, V259, V308, H310, Q311 (Kabat numbering of IgG). These amino acid residues have been identified from studies of the full IgG molecule and/or the Fc fragment to locate the residues of the CH2 domain that directly affect the interaction with FcRn. Three lines of investigation have been particularly illuminating: (a) crystallographic studies of the complexes of FcRn bound to Fc, (b) comparisons of the various human isotypes (IgG1, IgG2, IgG3 and IgG4) with each other and with IgGs from other species that exhibit differences in FcRn binding and serum half-life, correlating the variation in properties to specific amino acid residue differences, and (c) mutation analysis, particularly the isolation of mutations that show enhanced binding to FcRn, yet retain the pH-dependence of FcRn interaction. All three approaches highlight the same regions of CH2 region as crucial to the interaction with FcRn. The CH3 domain of IgG also contributes to the interaction with FcRn, but the protonation/deprotonation of H310 is thought to be primarily responsible and sufficient for the pH dependence of the interaction. In the present invention, a ribotoxin fusion protein may optionally comprise a CH2 domain with a functional FcRn binding site (or additional binding sites) for enhanced half life of the fusion protein molecule.

Heterologous: A heterologous polypeptide or polynucleotide refers to a polypeptide or polynucleotide derived from a different source or species.

Immune response: A response of a cell of the immune system, such as a B-cell, T cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunoconjugate: A covalent linkage of an effector molecule to a targeting molecule. The effector molecule can be a detectable label, biologically active protein, drug, cytotoxic molecule, or toxin (cytotoxic molecule).

Specific, non-limiting examples of toxins include, but are not limited to, abrin, ricin, *Pseudomonas* exotoxin (PE, such as PE35, PE37, PE38, and PE40), diphtheria toxin (DT), botulinum toxin, small molecule toxins, saporin, restrictocin or gelonin, sarcin, ricin, fragments thereof, or modified toxins thereof. Other cytotoxic agents may include auristatin, maytansinoids, and cytolytic peptides. Other immunoconjugates may be composed of a binding protein (e.g., a targeting molecule with a binding moiety) linked to drug molecules (ADC or "antibody drug conjugates"; Ducry and Stump, Bioconj Chem 21: 5-13, 2010; Erikson et al., Bioconj Chem 21: 84-92, 2010). These toxins/immunotoxins may directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as domain Ia of PE and the B chain of DT) and replacing it with a different targeting moiety. In some embodiments, a modified sarcin molecule or a fusion protein of the present invention is joined to an effector molecule (EM). Antibody drug conjugates (ADCs), which are drugs (e.g., cytotoxic agents) conjugated to antibodies (or fragments thereof), deliver therapeutic molecules to their conjugate binding partners. The effector molecule may be a small molecule drug or biologically active protein, such as erythropoietin. In some embodiments, the effector molecule may be an immunoglobulin domain, such as a VH or CH1 domain. In some embodiments, the modified sarcin molecule or the fusion protein joined to an effector molecule is further joined to a lipid or other molecule to a protein or peptide to increase its half-life. The linkage can be either by chemical or recombinant means. "Chemical means" refers to a reaction between the modified sarcin molecule or the fusion protein and the effector molecule such that there is a covalent bond formed between the two molecules to form one molecule. A peptide linker (short peptide sequence) can optionally be included between the modified sarcin molecule or the fusion protein and the effector molecule. Such a linker may be subject to proteolysis by an endogenous or exogenous linker to release the effector molecule at a desired site of action. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand, antibody or fragment or domain thereof, conjugated (coupled) to an effector molecule.

The terms "conjugating," "joining," "bonding" or "linking" refer to making two polypeptides into one contiguous polypeptide molecule, or to covalently attaching a radionucleotide or other molecule to a polypeptide. In the specific context, the terms can in some embodiments refer to joining a ligand, such as an antibody moiety, to an effector molecule ("EM"). The terms "conjugating," "joining," "bonding" or "linking" may also refer to attaching a peptide to a toxin (e.g., sarcin, modified sarcin molecule, etc.).

Immunogen: A compound, composition, or substance that is capable, under appropriate conditions, of stimulating an immune response, such as the production of antibodies or a T cell response in an animal, including compositions that are injected or absorbed into an animal.

The term "Immunogenicity" as used herein is the ability of an immunogen to elicit an immune response. The immune response can be both a humoral or cellular response. Preferably, the immune response is a T cell response. Measuring the activation of an immune response can be done by several methods well known in the art.

The term "reduced immunogenicity" as used herein means that the modified ribotoxin or modified ribotoxin fusion protein is less immunogenic than the corresponding non-modified ribotoxin or non-modified ribotoxin fusion protein. Preferably, the modified ribotoxin or modified ribotoxin fusion protein elicits a reduced T cell response as compared to the corresponding non-modified ribotoxin or non-modified ribotoxin fusion protein.

The term "reduced T cell response" as used herein means that the modified ribotoxin or modified ribotoxin fusion protein induces less T cell activation than the corresponding non-modified ribotoxin or non-modified ribotoxin fusion protein, as measured by an in vitro T cell proliferation ($^3${H}-thymidine incorporation) assay using CD8+ depleted, human peripheral blood mononuclear cells. In one embodiment, the stimulation index (SI) of the modified ribotoxin or modified ribotoxin fusion protein is less than 2.0, and more preferably less than 1.5. The term "stimulation index" as used herein refers to the ability of the modified ribotoxin or modified ribotoxin fusion protein to activate T cells. The SI is conventionally presented as the mean cpm per test samples/mean cpm per control samples (without any test peptide).

Isolated: An "isolated" biological component (such as a nucleic acid molecule or protein) that has been substantially separated or purified away from other biological components from which the component naturally occurs (for example, other biological components of a cell), such as other chromosomal and extra-chromosomal DNA and RNA and proteins, including other antibodies. Nucleic acids and proteins that have been "isolated" include nucleic acids and proteins purified by standard purification methods. An "isolated antibody" is an antibody that has been substantially separated or purified away from other proteins or biological components such that its antigen specificity is maintained. The term also embraces nucleic acids and proteins prepared by recombinant expression in a host cell, as well as chemically synthesized nucleic acids or proteins, or fragments thereof.

Label: A detectable compound or composition that is conjugated directly or indirectly to another molecule (e.g., a modified sarcin molecule, a targeting molecule, a ribotoxin fusion protein, etc.) to facilitate detection of that molecule. Specific, non-limiting examples of labels include fluorescent tags, enzymatic linkages, and radioactive isotopes.

Ligand contact residue or Specificity Determining Residue (SDR): An amino acid residue within a molecule that participates in contacting a ligand or antigen. A ligand contact residue is also known as a specificity determining residue (SDR).

Linkers: covalent or very tight non-covalent linkages; chemical conjugation or direct gene fusions of various amino acid sequences, especially those rich in Glycine, Serine, Proline, Alanine, or variants of naturally occurring linking amino acid sequences that connect immunoglobulin domains, and/or carbohydrates including but not limited to polyethylene glycols (PEGs), e.g., discrete PEGs (dPEGs). Typical lengths may range from 2 up to 20 or more amino acids, however the present invention is not limited to these lengths (e.g., the linker may be a peptide between 1 and 20 amino acids). The optimal lengths may vary to match the spacing and orientation of the specific target antigen(s), minimizing entropy but allowing effective binding of multiple antigens.

Modification: changes to a protein sequence, structure, etc., or changes to a nucleic acid sequence, etc. As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well.

Multimerizlng Domain. Many domains within proteins are known that form a very tight non-covalent dimer or multimer by associating with other protein domain(s). Some of the smallest examples are the so-called leucine zipper motifs, which are compact domains comprising heptad repeats that can either self-associate to form a homodimer (e.g. GCN4); alternatively, they may associate preferentially with another leucine zipper to form a heterodimer (e.g. myc/max dimers) or more complex tetramers (Chem Biol. 2008 Sep. 22; 15 (9):908-19. A heterospecific leucine zipper tetramer. Deng Y, Liu J, Zheng Q, Li Q, Kallenbach N R, Lu M.). Closely related domains that have isoleucine in place of leucine in the heptad repeats form trimeric "coiled coil" assemblies (e.g. HIV gp41). Substitution of isoleucine for leucine in the heptad repeats of a dimer can alter the favoured structure to a trimer. Small domains have advantages for manufacture and maintain a small size for the whole protein molecule, but larger domains can be useful for multimer formation. Any domains that form non-covalent multimers could be employed. For example, the CH3 domains of IgG form homodimers, while CH1 and CL domains of IgG form heterodimers.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide"

typically refers to short polynucleotides, generally no greater than about 50 nucleotides. It will be understood that when a nucleotide sequence is represented by a DNA sequence (i.e., A, T, G, C), this also includes a complementary RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

cDNA refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Recombinant nucleic acid refers to a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure may be conventional but are not limited to conventional vehicles. For example, E. W. Martin, *Remington's Pharmaceutical Sciences*, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21$^{st}$ Edition (2006) describe compositions and formulations suitable for pharmaceutical delivery of one or more therapeutic compounds or molecules, such as one or more antibodies, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. As a non-limiting example, the formulation for injectable trastuzumab includes L-histidine HCl, L-histidine, trehalose dihydrate and polysorbate 20 as a dry powder in a glass vial that is reconstituted with sterile water prior to injection. Other formulations of antibodies and proteins for parenteral or subcutaneous use are well known in the art. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are α-amino acids, either the L-optical isomer or the D-optical isomer can be used. The terms "polypeptide" or "protein" as used herein are intended to encompass any amino acid sequence and include modified sequences such as glycoproteins. The term "polypeptide" may cover naturally occurring proteins, as well as those that are recombinantly or synthetically produced. The term "residue" or "amino acid residue" includes reference to an amino acid that is incorporated into a protein, polypeptide, or peptide.

"Conservative" amino acid substitutions are those substitutions that do not substantially affect or decrease an activity or antigenicity of a polypeptide. For example, a polypeptide can include at most about 1, at most about 2, at most about 5, at most about 10, or at most about 15 conservative substitutions and specifically bind an antibody that binds the original polypeptide. The term conservative variation also includes the use of a substituted amino acid in place of an unsubstituted parent amino acid, provided that antibodies raised antibodies raised to the substituted polypeptide also immunoreact with the unsubstituted polypeptide. Examples of conservative substitutions include: (i) Ala-Ser; (ii) Arg-Lys; (iii) Asn-Gln or His; (iv) Asp-Glu; (v) Cys-Ser; (vi) Gln-Asn; (vii) Glu-Asp; (viii) His-Asn or Gln; (ix) Ile-Leu or Val; (x) Leu-Ile or Val; (xi) Lys-Arg, Gln, or Glu; (xii) Met-Leu or lie; (xiii) Phe-Met, Leu, or Tyr; (xiv) Ser-Thr; (xv) Thr-Ser; (xvi) Trp-Tyr; (xvii) Tyr-Trp or Phe; (xviii) Val-Ile or Leu.

Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain. The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamate or aspartate; or (d) a residue having a bulky side chain, for example, phenylalanine, is substituted for (or by) one not having a side chain, for example, glycine.

Preventing, treating, managing, or ameliorating a disease: "Preventing" a disease refers to inhibiting the full development of a disease. "Treating" refers to a therapeutic intervention that ameliorates a sign or symptom of a disease or pathological condition after it has begun to develop. "Managing" refers to a therapeutic intervention that does not allow the signs or symptoms of a disease to worsen. "Ameliorating" refers to the reduction in the number or severity of signs or symptoms of a disease.

Probes and primers: A probe comprises an isolated nucleic acid attached to a detectable label or reporter molecule. Primers are short nucleic acids, and can be DNA oligonucleotides 15 nucleotides or more in length, for example. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Purified: The term purified does not require absolute purity; rather, it is intended as a relative term. Thus, for example, a purified molecule is one that is isolated in whole or in part from naturally associated proteins and other contaminants in which the molecule is purified to a measurable degree relative to its naturally occurring state, for example, relative to its purity within a cell extract or biological fluid.

The term "purified" includes such desired products as analogs or mimetics or other biologically active compounds wherein additional compounds or moieties are bound to the molecule in order to allow for the attachment of other compounds and/or provide for formulations useful in therapeutic treatment or diagnostic procedures.

Generally, substantially purified molecules include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the molecule is purified to represent greater than 90%, often greater than 95% of all macromolecular species present in a purified preparation prior to admixture with other formulation ingredients. In other cases, the purified preparation may be essentially homogeneous, wherein other macromolecular species are less than 1%.

Recombinant protein: For a recombinant nucleic acid, see "Recombinant Nucleic Acid" above. A recombinant protein or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. Recombinant proteins may be made in cells transduced, transfected, or transformed with genetic elements to direct the synthesis of the heterologous protein. They may also be made in cell-free systems. Host cells that are particularly useful include mammalian cells such as CHO and HEK 293, insect cells, yeast such as *Pichia pastoris* or *Saccharomyces*, or bacterial cells such as *E. coli* or *Pseudomonas*.

Sample: A portion, piece, or segment that is representative of a whole. This term encompasses any material, including for instance samples obtained from a subject.

A "biological sample" is a sample obtained from a subject including, but not limited to, cells, tissues and bodily fluids. Bodily fluids include, for example, saliva, sputum, spinal fluid, urine, blood and derivatives and fractions of blood, including serum and lymphocytes (such as B cells, T cells and subfractions thereof). Tissues include those from biopsies, autopsies and pathology specimens, as well as biopsied or surgically removed tissue, including tissues that are, for example, unfixed, frozen, fixed in formalin and/or embedded in paraffin.

In some embodiments, a biological sample is obtained from a subject, such as blood or serum. A biological sample is typically obtained from a mammal, such as a rat, mouse, cow, dog, guinea pig, rabbit, or primate. In some embodiments, the primate is macaque, chimpanzee, or a human.

Scaffold: A platform molecule often used for introduction of other domains, loops, mutations, and the like. As an example, a CH2 or CH3 domain scaffold is a CH2 or CH3 domain that can be used to introduce donor loops and/or mutations (such as into the loop regions) in order to confer antigen binding to the CH2 or CH3 domain. In some embodiments, a scaffold is altered to exhibit increased stability compared with the native molecule. For example, a scaffold may be mutated to introduce pairs of cysteine residues to allow formation of one or more non-native disulfide bonds. Scaffolds are not limited to these definitions. In another example a scaffold can be the fibronectin type III domain, Centryns, Affibodies, DARPINS, cyclic peptides, nanoantibodies (VHH domains from llamas), shark domains, etc.

Sequence identity: The similarity between nucleotide or amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants will possess a relatively high degree of sequence identity overall or in certain regions when aligned using standard methods.

Methods of alignment of sequences for comparison are well known in the art. Various programs and alignment algorithms are described in: Smith and Waterman, Adv. Appl. Math. 2:482, 1981; Needleman and Wunsch, Journal of Molecular Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genetics 6:119-129, 1994.

The NCBI Basic Local Alignment Search Tool (BLAST™) (Altschul et al., Journal of Molecular Biology 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Specific binding agent: An agent that binds substantially only to a defined target. Thus an antigen specific binding agent is an agent that binds substantially to an antigenic polypeptide or antigenic fragment thereof. In one embodiment, the specific binding agent is a monoclonal or polyclonal antibody or a peptide or a scaffold molecule that specifically binds the antigenic polypeptide or antigenic fragment thereof.

The term "specifically binds" refers to the preferential association of a binding agent or targeting moiety (such as hormones, peptides, peptide fragments, domains, cytokines, other ligands and receptors, scaffolds, etc.), in whole or part, with target (e.g., a cell or tissue bearing that target of that binding agent) and not to non-targets (e.g., cells or tissues lacking a detectable amount of that target). It is, of course, recognized that a certain degree of non-specific interaction may occur between a molecule and a non-target cell or tissue. Nevertheless, specific binding may be distinguished as mediated through specific recognition of the antigen. A variety of immunoassay formats are appropriate for selecting molecules specifically reactive with a particular protein. For example, solid-phase ELISA immunoassays are routinely used.

Subject: Living multi-cellular organisms, including vertebrate organisms, a category that includes both human and non-human mammals.

Therapeutic agents include such compounds as nucleic acids, proteins, peptides, amino acids or derivatives, glycoproteins, radioisotopes, lipids, carbohydrates, small molecules, recombinant viruses, or the like. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al. 1985, Pharm. Ther. 28:341-365. Diagnostic agents or moieties include radioisotopes and other detectable labels. Detectable labels useful for such purposes are also well known in the art, and include radioactive isotopes such as $Tc^{99m}$, $In^{111}$, $^{32}P$, $^{125}I$, and $^{131}I$, fluorophores, chemiluminescent agents, and enzymes.

Therapeutically effective amount: A quantity of a specified agent sufficient to achieve a desired effect in a subject being treated with that agent. Such agents include the modified ribotoxin molecules (e.g., modified sarcin, clavin, gigantin, mitogillin, or restrictocin molecule) and fusion proteins described herein. For example, this may be the amount of a fusion protein comprising a modified sarcin molecule useful in preventing, treating or ameliorating a disease or condition, such as cancer. Ideally, a therapeutically effective amount of a modified ribotoxin molecule (e.g., modified sarcin, clavin, gigantin, mitogillin, or restrictocin molecule) or fusion protein is an amount sufficient to prevent, treat or ameliorate the condition or disease, in a subject without causing a substantial cytotoxic effect in the subject. The therapeutically effective amount of an agent useful for preventing, ameliorating, and/or treating a subject will be dependent on the subject being treated, the type and severity of the affliction, and the manner of administration of the therapeutic composition.

Toxin: See Immunoconjugate

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration. Such cells are sometimes called transformed cells.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

DETAILED DESCRIPTION

The present disclosure provides modified ribotoxin (e.g., α-sarcin, clavin, gigantin, mitogillin, and restrictocin) molecules, wherein the modified ribotoxin (e.g., α-sarcin, clavin, gigantin, mitogillin, and restrictocin) molecules are less or non-immunogenic compared to the corresponding wild type ribotoxin (e.g., wild type α-sarcin, clavin, gigantin, mitogillin, or restrictocin). The wild type ribotoxin (e.g., wild type α-sarcin, clavin, gigantin, mitogillin, or restrictocin) molecule is modified to create the "modified ribotoxin molecule," where the modification of the wild type ribotoxin molecule reduces its immunogenicity, e.g., reduces or eliminates the number of T cell epitopes (as described below). As used herein, the term "modified" can include one or more mutations, deletions, additions, substitutions, truncations, physical alteration (e.g., cross-linking modification, covalent bonding of a component, post-translational modification, e.g., acetylation, glycosylation), and the like.

T Cell Epitopes

When an antigen-presenting cell of the immune system takes up a protein, the protein is proteolytically digested ("processed") into peptides, some of which can bind to MHC class II molecules and be presented on the surface of antigen-presenting cells to T cells. The binding of peptides to MHC class II is believed to be due to interactions between amino acid side chains of the peptides and specific binding "pockets" within the MHC groove, e.g., pocket positions p1, p4, p6, p7 and p9 within the open-ended binding grooves of 34 human MHC class II alleles. The amino acids of the peptide that interact with the p1, p4, p6, p7, and p9 pocket positions of the class II MHC molecule are called anchor residues (e.g., P1, P4, P6, P7, and P9 class II MHC anchor residues).

In situations where such presented peptides activate CD4+ (helper) T cells, these peptides are defined as CD4+ T cell epitopes, which arise where the complex of peptide and MHC class II is bound by a T cell receptor and, in conjunction with co-stimulatory signals, result in T cell activation. In such cases, these peptides bind within a groove within the MHC class II molecule and allotypic variations in MHC class II can influence the binding of such peptides and, in some cases, can restrict binding to a small number of allotypes ("allotype-restricted"). In other cases, peptides can bind broadly to different MHC allotypes—such non-restricted binding is referred to as "promiscuous" or "degenerate" binding.

Modified Sarcin Molecules

Table 1 shows the sequence corresponding to wild type α-sarcin (SEQ ID NO: 1). The modified sarcin molecules of the present invention are derived from a "parent" α-sarcin, for example wild type α-sarcin or fragments of wild type α-sarcin.

TABLE 1

| SEQ ID NO | WILD TYPE α-SARCIN |
|---|---|
| 1 | AVTWTCLNDQ KNPKTNKYET KRLLYNQNKA ESNSHHAPLS DGKTGSSYPH WFTNGYDGDG KLPKGRTPIK FGKSDCDRPP KHSKDGNGKT DHYLLEFPTF PDGHDYKFDS KKPKENPGPA RVIYTYPNKV FCGIIAHTKE NQGELKLCSH |

U.S. Provisional Application No. 61/783,589, filed 15 Mar. 2013, which is incorporated by reference in its entirety, describes in silico analysis of the wild type α-sarcin protein to identify potential T cell epitopes. Briefly, all overlapping 9mer peptides from the wild type α-sarcin sequence were threaded through a database of 34 human MHC class II DR allotypes and individually scored based on their fit and interactions with each of the MHC class II molecules.

The results of this work suggest that wild type α-sarcin contains at least three potential T cell epitopes comprising a single promiscuous high affinity MHC binding peptide with p1 anchor at residue 24 (L/leucine), and two promiscuous moderate affinity MHC binding peptides with p1 anchors at residues 122 (V/valine) and 134 (I/isoleucine) (see Table 2). Other potential low to very low immunogenic T cell epitopes were also identified.

TABLE 2

| SEQ ID NO | POTENTIAL T CELL EPITOPES |
|---|---|
| 2 | Promiscuous high affinity MHC binding peptide with p1 anchor LYNQNKAES |
| 3 | Promiscuous moderate affinity MHC binding peptide with p1 anchor VIYTYPNKV |
| 4 | Promiscuous moderate affinity MHC binding peptide with p1 anchor IIAHTKENQ |

The wild type α-sarcin was further analyzed by the EpiScreen™ (Cambridge, UK) immunogenicity assay to identify the presence and potency of T cell epitopes within the wild type α-sarcin. Briefly, 46 15-mer peptides overlapping by 12 amino acids and spanning the wild type α-sarcin were tested for proliferation against 50 healthy PBMC donors selected to best represent the spread of HLA-DR alleles in the population. From this analysis, two T cell epitopes were identified within the wild type α-sarcin, as shown in Table 3.

TABLE 3

| SEQ ID NO | T CELL EPITOPES IDENTIFIED BY EPISCREEN ™ |
|---|---|
| 5 | QKNPKTNKY (Sarcin Epitope 1) |
| 4 | IIAHTKENQ (Sarcin Epitope 2) |

Sarcin Epitope 1 corresponds to amino acid residues 10-18 of the wild type α-sarcin within the N-terminal 22 amino acid region involved in membrane and interaction and binding of α-sarcin to the ribosome. Sarcin Epitope 1 can optionally include the immediately adjacent N-terminal amino acid (P-1 anchor residue) and, thus, comprise the amino acid sequence DQKNPKTNKY (SEQ ID NO:6) corresponding to amino acids 9-18 of the wild type α-sarcin.

The Sarcin Epitope 1 can be modified to reduce or eliminate human MHC class II binding. In one embodiment, the modified Sarcin Epitope 1 has one or more mutations in one or more of the P-1, P1, P4, P6, P7, or P9 MHC class II anchor residues of Sarcin Epitope 1, where the P-1 anchor residue corresponds to the amino acid (D) directly N-terminal to the Sarcin Epitope 1 in the wild type α-sarcin. In another embodiment, the modified Sarcin Epitope 1 has one or more of the following substitutions: P-1 at residue D9: D9T or D9A; P1 anchor at residue Q10: Q10K, Q10R, or Q10A; P4 anchor at residue P13: P13I; P6 anchor at residue T15: T15G, T15Q, or T15H; P7 anchor residue at N16: N16R, N16K, N16A; and/or P9 anchor at residue Y18: Y18H, Y18K, or Y18R. Put another way, the modified Sarcin Epitope 1 has the amino acid sequence of $X_1X_2KNX_3KX_4X_5KX_6$, wherein $X_1$ is D, A, or T; $X_2$ is Q, K, R, or A; $X_3$ is P or I; $X_4$ is T, G, Q, or H; $X_5$ is N, R, K or A; and $X_6$ is Y, H, K, or R (SEQ ID NO:7).

In addition to modifying one or more anchor residues, it is also possible to modify one or more non-anchor residues in the Sarcin Epitope 1 provided the modified epitope retains reduced MHC class II binding as compared to wild type α-sarcin. An alignment of Sarcin Epitope 1 with the corresponding epitope in other related, fungal ribotoxins provides guidance as to possible non-anchor residue substitutions. One of ordinary skill in the art could readily identify other non-anchor residue substitutions using conventional methods and techniques.

In another embodiment, the modified Sarcin Epitope 1 has the amino acid sequence of $X_1X_2NX_3KX_4X_5KX_6$, wherein $X_1$ is Q, K, R, or A; $X_2$ is K or L; $X_3$ is P or I; $X_4$ is T, G, Q, or H; $X_5$ is N, R, K or A; and $X_6$ is Y, H, K, R, or W (SEQ ID NO:8). In yet another embodiment the modified Sarcin Epitope 1 has the amino acid sequence of $X_1X_2X_3NX_4KX_5X_6KX_7$, wherein $X_1$ is D, A, or T; $X_2$ is Q, K, R, or A; $X_3$ is K or L; $X_4$ is P or I; $X_5$ is T, G, Q, or H; $X_6$ is N, R, K or A; and $X_7$ is Y, H, K, R, or W (SEQ ID NO:9).

Sarcin Epitope 2 corresponds to amino acid residues 134-142 of the wild type α-sarcin and, thus, spans H137, which is part of the catalytic triad. The Sarcin Epitope 2 can be modified to reduce or eliminate human MHC class II binding. In one embodiment, the modified Sarcin Epitope 2 has one or more mutations in one or more of the P1, P6, P7, or P9 MHC class II anchor residues of Sarcin Epitope 2. In another embodiment, the modified Sarcin Epitope 2 has one or more of the following substitutions: P1 anchor at residue I134: I134A; P6 anchor at residue K139: K139D, K139E, K139G, K139Q, K139H, or K139N; P7 anchor residue at E140: E140D; and/or P9 anchor at residue Q142: Q142D, Q142N, Q142T, Q142E, Q142R, or Q142G. Put another way, the modified Sarcin Epitope 2 has the amino acid sequence of $X_1IAHTX_2X_3NX_4$, wherein $X_1$ is I or A; $X_2$ is K, D, E, G, Q, H, or N; $X_3$ is E or D; and $X_4$ is Q, D, N, T, E, R, or G (SEQ ID NO:10).

In addition to modifying one or more anchor residues, it is also possible to modify one or more non-anchor residues in the Sarcin Epitope 2 provided the modified epitope retains reduced MHC class II binding as compared to wild type α-sarcin. An alignment of Sarcin Epitope 2 with the corresponding epitope in other related, fungal ribotoxins provides guidance as to possible non-anchor residue substitutions. One of ordinary skill in the art could readily identify other non-anchor residue substitutions using conventional methods and techniques.

In another embodiment, the modified Sarcin Epitope 2 has the amino acid sequence of $X_1X_2AHX_3X_4X_5NX_6$, wherein $X_1$ is I or A; $X_2$ is I or V; $X_3$ is T or Q; $X_4$ is K, D, E, G, Q, H, or N; $X_5$ is E or D; and $X_6$ is Q, D, N, T, E, R, or G (SEQ ID NO:11).

Without intending to be bound by any theory or mechanism, it is believed that the mutations that reduce or eliminate human MHC class II binding as described herein may help reduce or eliminate the immunogenicity of wild type α-sarcin in humans (e.g., via reducing the number and/or immunogenicity of T cell epitopes).

In some embodiments, the modified sarcin molecule comprises at least one fewer T cell epitope as compared to wild type α-sarcin (or at least two fewer T cell epitopes, at least three fewer T cell epitopes, etc.). For example, if the wild type α-sarcin comprises two T cell epitopes, in some embodiments, the modified sarcin molecule comprises one T cell epitope or zero T cell epitopes. Or, if the wild type α-sarcin comprises three T cell epitopes, in some embodiments, the modified sarcin molecule comprises two T cell epitopes, one T cell epitope, or zero T cell epitopes. Or, if the wild type α-sarcin comprises ten T cell epitopes, in some embodiments, the modified sarcin molecule comprises nine T cell epitopes, eight T cell epitopes, seven T cell epitopes, six T cell epitopes, five T cell epitopes, four T cell epitopes, three T cell epitopes, two T cell epitopes, one T cell epitope, or zero T cell epitopes. Or, if the wild type α-sarcin comprises eight T cell epitopes, in some embodiments, the modified sarcin molecule comprises seven T cell epitopes, six T cell epitopes, five T cell epitopes, four T cell epitopes, three T cell epitopes, two T cell epitopes, one T cell epitope, or zero T cell epitopes. Or, if the wild type α-sarcin comprises six T cell epitopes, in some embodiments, the modified sarcin molecule comprises five T cell epitopes, four T cell epitopes, three T cell epitopes, two T cell epitopes, one T cell epitope, or zero T cell epitopes. Or, if the wild type α-sarcin comprises four T cell epitopes, in some embodiments, the modified sarcin molecule comprises three T cell epitopes, two T cell epitopes, one T cell epitope, or zero T cell epitopes.

More specifically, the modified sarcin molecule may comprise at least one mutation compared with a "parent" α-sarcin, the parent α-sarcin being at least a portion of wild type α-sarcin (e.g., wild type α-sarcin, a fragment of wild type α-sarcin, etc.). In one embodiment, the at least one mutation comprises a mutation of a T cell epitope, e.g., resulting in the epitope having reduced ability to bind to MHC class II molecules or having no ability to bind MHC class II molecules or resulting in a modified sarcin molecule that elicits a reduced T cell response as compared to the corresponding wild type α-sarcin. For example, the at least one mutation may be within Sarcin T Cell Epitope 1 (SEQ ID NO:5 or SEQ ID NO:6) and/or within Sarcin T Cell Epitope 2 (SEQ ID NO:4).

In some embodiments, the modified sarcin molecule comprises at least one mutation compared with a "parent" α-sarcin (e.g., a wild type α-sarcin, a fragment of wild type α-sarcin, etc.), wherein the at least one mutation comprises a mutation of at least one of amino acids D9, Q10, P13, T15, N16, or Y18 (of wild type α-sarcin).

For example, in some embodiments, the modified sarcin molecule comprises one or more of the following mutations compared with a "parent" α-sarcin (e.g., a wild type α-sarcin, a fragment of wild type α-sarcin, etc.): D9T, D9A, Q10K, Q10R, Q10A, P13I, T15G, T15Q, T15H, N16R, N16K, N16A, Y18H, Y18K, or Y18R.

In some embodiments, the modified sarcin molecule comprises at least one mutation compared with a "parent" α-sarcin (e.g., a wild type α-sarcin, a fragment of wild type α-sarcin, etc.), wherein the at least one mutation comprises a mutation of at least one of amino acids I134, K139, E140, or Q142.

For example, in some embodiments, the modified sarcin molecule comprises one or more of the following mutations compared with a "parent" α-sarcin (e.g., a wild type α-sarcin, a fragment of wild type α-sarcin, etc.): I134A, K139D, K139E, K139G, K139Q, K139H, K139N, E140D, Q142D, Q142N, Q142T, Q142E, Q142R, or Q142G.

In other embodiments, the modified sarcin molecule comprises a first and a second mutation compared with a "parent" α-sarcin (e.g., a wild type α-sarcin, a fragment of wild type α-sarcin, etc.), wherein the first mutation comprises a mutation of at least one of amino acids D9, Q10, P13, T15, N16, or Y18 (of wild type α-sarcin) and wherein the second mutation comprises a mutation of at least one of amino acids I134, K139, E140, or Q142 (of wild type α-sarcin). For example, in certain embodiments, the modified sarcin molecule comprises one or more of the following mutations compared with a "parent" α-sarcin (e.g., a wild type α-sarcin, a fragment of wild type α-sarcin, etc.): a first mutation at Q10 and a second mutation at K139 or Q142; a first mutation at N16 and a second mutation at K139 or Q142; or a first mutation at Y18 and a second mutation at K139 or Q142.

For example, in some embodiments, the modified sarcin molecule comprises a first mutation compared with a wild type α-sarcin (SEQ ID NO:1), wherein the first mutation is selected from D9T, D9A, Q10K, Q10R, Q10A, P13I, T15G, T15Q, T15H, N16R, N16K, N16A Y18H, Y18K, or Y18R and a second mutation compared with a wild type α-sarcin, wherein the second mutation is selected from I134A, K139D, K139E, K139G, K139Q, K139H, K139N, E140D, Q142D, Q142N, Q142T, Q142E, Q142R, or Q142G.

In other embodiments, the modified sarcin molecule comprises one or more of the following mutations compared with a "parent" α-sarcin (e.g., a wild type α-sarcin, a fragment of wild type α-sarcin, etc.): a first mutation comprising Q10K and a second mutation comprising K139D, K139E, Q142N or Q142T; a first mutation comprising N16R and a second mutation comprising K139D, K139E, Q142N, or Q142T; a first mutation comprising N16K and a second mutation comprising K139D, K139E, Q142N, or Q142T; a first mutation comprising Y18K and a second mutation comprising K139D, K139E, Q142N, or Q142T; or a first mutation comprising Y18R and a second mutation comprising K139D, K139E, Q142N, or Q142T.

In other embodiments, the modified sarcin molecule comprises three mutations compared with a "parent" α-sarcin (e.g., a wild type α-sarcin, a fragment of wild type α-sarcin, etc.). For example, the modified sarcin molecule may comprise a first and second mutation within Sarcin T Cell Epitope 1 (SEQ ID NO:5 or SEQ ID NO:6) and a third mutation within Sarcin T Cell Epitope 2 (SEQ ID NO:4). Alternatively, the modified sarcin molecule may comprise a first mutation within Sarcin T Cell Epitope 1 (SEQ ID NO:5 or SEQ ID NO:6) and a second and third mutation within Sarcin T Cell Epitope 2 (SEQ ID NO:4).

In certain embodiments, the modified sarcin molecule comprises one or more of the following mutations compared with a "parent" α-sarcin (e.g., a wild type α-sarcin, a fragment of wild type α-sarcin, etc.): a first mutation at amino acid Q10 or N16, a second mutation at K139, and a third mutation at Q142. In one embodiment, the first mutation at Q10 or N16 is selected from Q10K, Q10R, or Q10A or N16R, N16K, or N16A (preferably Q10K or N16R). In another embodiment, the second mutation at K139 is selected from K139D, K139E, K139G, K139Q, K139H, or K139N (preferably K139D or K139E). In another embodiment, the third mutation at Q142 is selected from Q142D, Q142N, Q142T, Q142E, Q142R, or Q142G (preferably Q142T).

In yet another embodiment, the first mutation is Q10K or N16R, the second mutation is K139E or K139D and the third mutation is Q142T. In another embodiment, the first mutation is Q10K, the second mutation is K139E, and the third mutation is Q142T. In another embodiment, the first mutation is Q10K, the second mutation is K139D, and the third mutation is Q142T. In another embodiment, the first mutation is N16R, the second mutation is K139E, and the third mutation is Q142T. In another embodiment, the first mutation is N16R, the second mutation is K139D, and the third mutation is Q142T.

In other embodiments, modified sarcin molecule comprises four mutations mutations compared with a "parent" α-sarcin (e.g., a wild type α-sarcin, a fragment of wild type α-sarcin, etc.). For example, the modified sarcin molecule may comprise two mutations within Sarcin T Cell Epitope 1 (SEQ ID NO:5 or SEQ ID NO:6) and two mutations within Sarcin T Cell Epitope 2 (SEQ ID NO:4); one mutation within Sarcin T Cell Epitope 1 (SEQ ID NO:5 or SEQ ID NO:6) and three mutations within Sarcin T Cell Epitope 2 (SEQ ID NO:4); or three mutations within Sarcin T Cell Epitope 1 (SEQ ID NO:5 or SEQ ID NO:6) and one mutation within Sarcin T Cell Epitope 2 (SEQ ID NO:4).

In yet another embodiment, the modified sarcin polypeptide comprises at least one mutation as compared to a wild type α-sarcin polypeptide (SEQ ID NO:1), wherein the amino acid sequence of the modified sarcin polypeptide comprises:

AVTWTCLNX$_1$X$_2$ KNX$_3$KX$_4$X$_5$KX$_6$ET KRLLYNQNKA ESNSHHAPLS
DGKTGSSYPH WFTNGYDGDG KLPKGRTPIK FGKSDCDRPP
KHSKDGNGKT DHYLLEFPTF PDGHDYKFDS KKPKENPGPA
RVIYTYPNKV FCGX$_7$IAHTX$_8$X$_9$ NX$_{10}$GELKLCSH, wherein X$_1$ through X$_{10}$ can be any amino acid (SEQ ID NO:12), provided the modified sarcin polypeptide is not identical to the wild type α-sarcin polypeptide (SEQ ID NO:1).

In another embodiment, X$_1$ is D, A, or T; X$_2$ is Q, K, R, or A; X$_3$ is P or I; X$_4$ is T, G, Q, or H; X$_5$ is N, R, K or A; X$_6$ is Y, H, K, or R; X$_7$ is I or A; X$_8$ is K, D, E, G, Q, H, or N; X$_9$ is E or D; and X$_{10}$ is Q, D, N, T, E, R, or G (SEQ ID NO:13).

Table 4 describes non-limiting examples of modified sarcin molecules. The modified sarcin molecules in Table 4 comprise one or more of the amino acid substitutions described above.

TABLE 4

| SEQ ID NO: | Variant |
|---|---|
| 14 | Q10X (X = K or A)<br>AVTWTCLND<u>X</u> KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCG<u>II</u>AHTKE NQGELKLCSH |
| 15 | N16X (X = R, K or A)<br>AVTWTCLNDQ KNPKT<u>X</u>KYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHT<u>KE</u> NQGELKLCSH |
| 16 | Y18X (X = K or R)<br>AVTWTCLNDQ KNPKTNK<u>X</u>ET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE N<u>Q</u>GELKLCSH |
| 17 | K139X (X = D or E)<br>AVTWTCLNDQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTX<u>E</u> NQGELKLCSH |
| 18 | E140D<br>AVTWTCLNDQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTK<u>D</u> NQGELKLCSH |
| 19 | Q142X (X = N, T, or E)<br>AVTWTCLNDQ KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE N<u>X</u>GELKLCSH |
| 20 | Q10K + K139X (X = D or E)<br>AVTWTCLND<u>K</u> KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHT<u>XE</u> NQGELKLCSH |
| 21 | N16R + K139X (X = D or E)<br>AVTWTCLNDQ KNPKT<u>R</u>KYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHT<u>XE</u> NQGELKLCSH |
| 22 | Y18X$_1$ (X$_1$ = K or R) + K139X$_2$ (X$_2$ = D or E)<br>AVTWTCLNDQ KNPKTNK<u>X$_1$</u>ET KRLLYNQNKA ESNSHHAPLS<br>DGKTGSSYPH WFTNGY<u>D</u>GDG KLPKGRTPIK FGKSDCDRPP<br>KHSKDGNGKT DHYLLEFPTF PDGHDYKFDS KKPKENPGPA<br>RVIYTYPNKV FCGIIAHT<u>X$_2$</u>E NQGELKLCSH |
| 23 | Q10K + Q142T<br>AVTWTCLND<u>K</u> KNPKTNKYET KRLLYNQNKA ESNSHHAPLS<br>DGKTGSSYPH WFTNGYDGDG KLPKGRTPIK FGKSDCDRPP<br>KHSKDGNGKT DHYLLEFPTF PDGHDYKFDS KKPKENPGPA<br>RVIYTYPNKV FCGIIAHTKE N<u>T</u>GELKLCSH |
| 46 | Q10K + K139D + Q142T<br>AVTWTCLND<u>K</u> KNPKTNKYET KRLLYNQNKA ESNSHHAPLS<br>DGKTGSSYPH WFTNGYDGDG KLPKGRTPIK FGKSDCDRPP |

TABLE 4-continued

| SEQ ID NO: | Variant |
|---|---|
| | KHSKDGNGKT DHYLLEFPTF PDGHDYKFDS KKPKENPGPA RVIYTYPNKV FCGIIAHTDE NTGELKLCSH |
| 47 | Q10K + K139E + Q142T AVTWTCLNDK KNPKTNKYET KRLLYNQNKA ESNSHHAPLS DGKTGSSYPH WFTNGYDGDG KLPKGRTPIK FGKSDCDRPP KHSKDGNGKT DHYLLEFPTF PDGHDYKFDS KKPKENPGPA RVIYTYPNKV FCGIIAHTEE NTGELKLCSH |
| 48 | N16R + K139D + Q142T AVTWTCLNDQ KNPKTRKYET KRLLYNQNKA ESNSHHAPLS DGKTGSSYPH WFTNGYDGDG KLPKGRTPIK FGKSDCDRPP KHSKDGNGKT DHYLLEFPTF PDGHDYKFDS KKPKENPGPA RVIYTYPNKV FCGIIAHTDE NTGELKLCSH |
| 49 | N16R + K139E + Q142T AVTWTCLNDQ KNPKTRKYET KRLLYNQNKA ESNSHHAPLS DGKTGSSYPH WFTNGYDGDG KLPKGRTPIK FGKSDCDRPP KHSKDGNGKT DHYLLEFPTF PDGHDYKFDS KKPKENPGPA RVIYTYPNKV FCGIIAHTEE NTGELKLCSH |

Modification of the wild type α-sarcin may include an amino acid substitution as described above. In some embodiments, the amino acid substitution is a 1 amino acid substitution (e.g., Q10A), a 2 amino acid substitution (e.g., Q10A and Q142G), a 3 amino acid substitution (e.g., Q10A, N16A, Q142G), a 4 amino acid substitution, a 5 amino acid substitution, 6 amino acid substitution, a 7 amino acid substitution, an 8 amino acid substitution, a nine amino acid substitution, a 10 amino acid substitution, or a more than 10 amino acid substitution.

Modification of the wild type α-sarcin is not limited to an amino acid substitution. For example, the modification may include an amino acid deletion or an amino acid addition. In some embodiments, the amino acid deletion is a 1 amino acid deletion, a 2 amino acid deletion, a 3 amino acid deletion, a 4 amino acid deletion, a 5 amino acid deletion, 6 amino acid deletion, a 7 amino acid deletion, an 8 amino acid deletion, a nine amino acid deletion, a 10 amino acid deletion, or a more than 10 amino acid deletion. In some embodiments, the amino acid addition is a 1 amino acid addition, a 2 amino acid addition, a 3 amino acid addition, a 4 amino acid addition, a 5 amino acid addition, 6 amino acid addition, a 7 amino acid addition, an 8 amino acid addition, a nine amino acid addition, a 10 amino acid addition, or a more than 10 amino acid addition. Deletions and/or additions may optionally correspond to deletions in regions of the molecule other than T cell epitope regions.

Wild type α-sarcin comprises two disulfide bonds (between amino acids Cys 6 and Cys 148 and between amino acids Cys 76 and Cys 132). In some embodiments, the modified sarcin molecule comprises an additional disulfide bond. In some embodiments, the additional disulfide bond can be added in sites adjacent to the wild type disulfide bond sites. In some embodiments, additional disulfide bonds are incorporated into the molecule by adding amino acids. In some embodiments, disulfide bonds are incorporated into the molecule by substituting amino acids. In some embodiments, the modified sarcin molecule has no disulfide bonds.

Modification of the wild type α-sarcin may include an amino acid substitution (as described above) and an additional modification, for example a deletion, an addition, a truncation (e.g., N-terminal truncation, C-terminal truncation), or a combination thereof.

Other Modified Fungal Ribotoxin Molecules

As discussed above, in addition to α-sarcin, there are other related ribotoxin family members produced by other *Aspergillus* species, including clavin, gigantin, mitogillin, and restrictocin. Table 5 shows the sequences corresponding to wild type clavin (SEQ ID NO:24), gigantin (SEQ ID NO:25), mitogillin (SEQ ID NO:26), and restrictocin (SEQ ID NO:45). The modified clavin, gigantin, mitogillin, and restrictocin molecules of the present invention are derived from a "parent" clavin, gigantin, mitogillin, and restrictocin, respectively, for example wild type clavin, gigantin, mitogillin, or restrictocin, or fragments of wild type clavin, gigantin, mitogillin, or restrictocin.

TABLE 5

| SEQ ID NO | WILD TYPE CLAVIN |
|---|---|
| 24 | AATWTCMNEQKNPKTNKYENKRLLYNQNNAESNAHHAPL SDGKTGSSYPHWFTNGYDGDGKILKGRTPIKWGNSDCDR PPKHSKNGDGKNDHYLLEFPTFPDGHQYNFDSKKPKEDP GPARVIYTYPNKVFCGIVAHTRENQGDLKLCSH |
| SEQ ID NO | WILD TYPE GIGANTIN |
| 25 | AVTWTCLNEQKNIKTNKYETKRLLYNQDKAESNSHHAPL SDGKTGSSYPHWFTNGYDGEGKILKGRTPIKFGKSDCDR PPKHSKDGNGKNDHYLLEFPTFPDGHDYKFDSKKPKEDP GPARVIYTYPNKVFCGIIAHTRENQGELKLCSH |
| SEQ ID NO | WILD TYPE MITOGILLIN |
| 26 | ATWTCINQQLNPKTNKWEDKRLLYSQAKAESNSHHAPLS DGKTGSSYPHWFTNGYDGNGKLIKGRTPIKFGKADCDRP PKHSQNGMGKDDHYLLEFPTFPDGHDYKFDSKKPKEDPG PARVIYTYPNKVFCGIVAHQRGNQGDLRLCSH |
| SEQ ID NO | WILD TYPE RESTRICTOCIN |
| 45 | ATWTCINQQLNPKTNKWEDKRLLYSQAKAESNSHHAPLS DGKTGSSYPHWFTNGYDGNGKLIKGRTPIKFGKADCDRP PKHSQNGMGKDDHYLLEFPTFPDGHDYKFDSKKPKENPG PARVIYTYPNKVFCGIVAHQRGNQGDLRLCSH |

An example of a rapid method for analysis of the immunogenicity of a protein molecule involves the prediction of peptide binding to human MHC class II molecules. While only a proportion of peptides that bind to MHC class II will be actual T cell epitopes, the analysis of peptide binding to MHC class II can provide a rapid analysis of the potential for immunogenicity of a protein sequence because CD4+ T cell epitopes bind MHC class II. Furthermore, promiscuous high affinity MHC class II binding peptides have been shown to correlate with the presence of T cell epitopes (Hill et al., 2003, Arthritis Res Ther, 1:R40-R48) and thus analysis of such promiscuous binding peptides provides a basis for analysis of "potential" T cell epitopes.

Computer methods have been developed to model such interactions, such as iTope (Perry et al., 2008, Drugs in R&D, 9 (6) 385-396), which is based on Peptide Threading software (WO 02/069232, WO 98/59244). In iTope, overlapping 9mers from a sequence of interest are individually tested for interaction with 34 different human MHC class II DR allotypes and individually scored based on their fit and interactions with each of the MHC class II molecules. For each MHC allotype, the combined strength of interactions can provide a prediction of the strength of physical binding of each 9mer peptide and the designation of high affinity binding peptides. By collective analysis of the binding of a 9mer to all 34 MHC class II allotypes, the extent of promiscuous or restricted binding can be determined. This allows the identification of promiscuous high affinity MHC class II binding peptides that are thus considered to have high potential for having T cell epitope activities.

The wild type amino acid sequences of clavin, gigantin, mitogillin, and restrictocin were analyzed for non-self human MHC class II binders. All overlapping 9mers from the wild type ribotoxin sequences were threaded through a database of 34 human MHC class II DR allotypes and individually scored based on their fit and interactions with each of the MHC class II molecules. The predicted binding to MHC class II where the position of the first residue of a 9mer peptide binding to MHC class II allotype ("p1 anchor") has a binding score of 0.55-0.6 or a binding score was >0.6. Regions containing potentially immunogenic peptides are indicated as "Promiscuous High" and "Promiscuous Moderate." "Promiscuous High" MHC binding peptides are defined as both 50% of Total Alleles Binding and High Affinity alleles binding to MHC class II. "Promiscuous Moderate" MHC binding peptides are defined as 50% of Total Alleles Binding to MHC class II but <50% of High Affinity alleles binding to MHC class II.

The results of this work suggest that wild type clavin contains several potential T cell epitopes, including a promiscuous high affinity MHC binding peptide with p1 anchor at residue 134 (I/isoleucine), and three promiscuous moderate affinity MHC binding peptides with p1 anchors at residues 63 (L/leucine), 122 (V/valine), and 130 (V/valine) (see Table 6). Potential low to very low immunogenic T cell epitopes were also identified.

TABLE 6

| SEQ ID NO | POTENTIAL CLAVIN T CELL EPITOPES |
|---|---|
| 27 | Promiscuous high affinity MHC binding peptide with p1 anchor I134<br>IVAHTRENQ |
| 28 | Promiscuous moderate affinity MHC binding peptide with p1 anchor L63<br>LKGRTPIKW |
| 3 | Promiscuous moderate affinity MHC binding peptide with p1 anchor V122<br>VIYTYPNKV |
| 29 | Promiscuous moderate affinity MHC binding peptide with p1 anchor V130<br>VFCGIVAHT |

In addition, the EpiScreen™ (Cambridge, UK) immunogenicity analysis of α-sarcin, suggests that clavin contains the following T cell epitope having a p1 anchor residue of Q10: QKNPKTNKY (SEQ ID NO:5).

The in silico work also suggests that wild type gigantin contains several potential T cell epitopes, including two promiscuous high affinity MHC binding peptides with p1 anchors at residue at residues 63 (L/leucine) and 122 (V/valine) (see Table 7). Potential low to very low immunogenic T cell epitopes were also identified.

TABLE 7

| SEQ ID NO | POTENTIAL GIGANTIN T CELL EPITOPES |
|---|---|
| 30 | Promiscuous high affinity MHC binding peptide with p1 anchor L63<br>LKGRTPIKF |

TABLE 7-continued

| SEQ ID NO | POTENTIAL GIGANTIN T CELL EPITOPES |
|---|---|
| 3 | Promiscuous moderate affinity MHC binding peptide with p1 anchor V122<br>VIYTYPNKV |

In addition, the EpiScreen™ (Cambridge, UK) immunogenicity analysis of α-sarcin, suggests that gigantin contains the following two T cell epitopes having p1 anchor residues of Q10 and I134, respectively: QKNIKTNKY (SEQ ID NO:31) and IIAHTRENQ (SEQ ID NO:32).

The in silico work also suggests that wild type mitogillin and restrictocin, which are variants of the same protein isolated from *Aspergillus restrictus*, contain several potential T cell epitopes, including three promiscuous high affinity MHC binding peptides with p1 anchors at residue at residues 62 (I/Isoleucine), 129 (V/valine), and 133 (I/isoleucine) and a single promiscuous moderate affinity MHC binding peptide with a p1 anchor at residue 121 (V/valine) (see Table 8). Potential low to very low immunogenic T cell epitopes were also identified.

TABLE 8

| SEQ ID NO | POTENTIAL MITOGILLIN/RESTRICTOCIN T CELL EPITOPES |
|---|---|
| 33 | Promiscuous high affinity MHC binding peptide with p1 anchor 162<br>IKGRTPIKF |
| 34 | Promiscuous high affinity MHC binding peptide with p1 anchor V129<br>VFCGIVAHQ |
| 35 | Promiscuous high affinity MHC binding peptide with p1 anchor I133<br>IVAHQRGNQ |
| 3 | Promiscuous moderate affinity MHC binding peptide with p1 anchor V121<br>VIYTYPNKV |

In addition, the EpiScreen™ (Cambridge, UK) immunogenicity analysis of α-sarcin suggests that mitogillin and restrictocin contain the following T cell epitope having a p1 anchor residue of Q10: QLNPKTNKW (SEQ ID NO:36).

The above-identified clavin, gigantin, mitogillin, and restrictocin T cell epitopes can be modified to reduce or eliminate human MHC class II binding. In one embodiment, the modified clavin, gigantin, mitogillin, or restrictocin T cell epitope has one or more mutations in one or more of the P1, P4, P6, P7, or P9 MHC class II anchor residues.

In one embodiment, the modified clavin or gigantin epitope with p1 anchor Q10 has one or more of the following substitutions: P1 anchor at residue Q10: Q10K, Q10R, or Q10A; P4 anchor at residue P13 (for clavin only): P13I; P6 anchor at residue T15: T15G, T15Q, or T15H; P7 anchor residue at N16: N16R, N16K, or N16A; and/or P9 anchor at residue Y18: Y18H, Y18K, or Y18R.

In another embodiment, the modified mitogillin or restrictocin epitope with p1 anchor Q9 has one or more of the following substitutions: P1 anchor at residue Q9: Q9K, Q9R, or Q9A; P4 anchor at residue P12: P12I; P6 anchor at residue T14: T14G, T14Q, or T14H; P7 anchor residue at N15: N15R, N15K, or N15A; and/or P9 anchor at residue Y17: Y17H, Y17K, or Y17R.

In another embodiment, the modified clavin epitope with p1 anchor L63 has one or more of the following substitutions: P1 anchor at residue L63: L63A or L63D; P4 anchor at residue R66: R66G, R66Q, R66H, R66N, R66D, R66E; P7 anchor residue at I69: I69A or I69D; and/or P9 anchor at residue W71: W71G, W71A, W71D, or W71E.

In another embodiment, the modified gigantin epitope with p1 anchor L63 has one or more of the following substitutions: P1 anchor at residue L63: L63A or L63D; P4 anchor at residue R66: R66G, R66Q, R66H, R66N, R66D, R66E; P7 anchor residue at I69: I69A or I69D; and/or P9 anchor at residue F71: F71G, F71A, F71 D, or F71E.

In another embodiment, the modified mitogillin or restrictocin epitope with p1 anchor I62 or has one or more of the following substitutions: P1 anchor at residue I62: I62A or I62D; P4 anchor at residue R65: R65G, R65Q, R65H, R65N, R65D, R65E; P7 anchor residue at I68: I68A or I68D; and/or P9 anchor at residue F70: F70G, F70A, F70D, or F70E.

In another embodiment, the modified clavin or gigantin epitope with p1 anchor V122 has one or more of the following substitutions: P1 anchor at residue V122: V122A, V122K, or V122R; P4 anchor at residue T125: T125G, T125Q, or T125H; P6 anchor at residue P127: P127I; P7 anchor residue at N128: N128R, N128K, or N128A; and/or P9 anchor at residue V130: V130A, V130K or V130R.

In another embodiment, the modified mitogillin or restrictocin epitope with p1 anchor V121 has one or more of the following substitutions: P1 anchor at residue V121: V121A, V121K, or V121R; P4 anchor at residue T124: T124G, T124Q, or T124H; P6 anchor at residue P126: P126I; P7 anchor residue at N127: N127R, N127K, or N127A; and/or P9 anchor at residue V129: V129A, V129K or V129R.

In another embodiment, the modified clavin epitope with p1 anchor V130 has one or more of the following substitutions: P1 anchor at residue V130: V130A, V130K, or V130R; P4 anchor at residue G133: G133A, G133D, G133E, or G133K; P7 anchor residue at A136: A136R, A136K, or A136D; and/or P9 anchor at residue T138: T138G or T138H.

In another embodiment, the modified mitogillin or restrictocin epitope with p1 anchor V129 has one or more of the following substitutions: P1 anchor at residue V129: V129A, V129K, or V129R; P4 anchor at residue G132: G132A, G132D, G132E, or G132K; P7 anchor residue at A135: A135R, A135K, or A135D; and/or P9 anchor at residue Q137: Q137G or Q137H.

In another embodiment, the modified clavin epitope with p1 anchor I134 has one or more of the following substitutions: P1 anchor at residue I134: I134A; P6 anchor at residue R139: R139D, R139E, R139G, R139Q, R139H, or R139N; P7 anchor residue at E140: E140D; and/or P9 anchor at residue Q142: Q142D, Q142N, Q142T, Q142E, Q142R, or Q142G.

In another embodiment, the modified mitogillin or restrictocin epitope with p1 anchor I133 has one or more of the following substitutions: P1 anchor at residue I133: I133A; P6 anchor at residue R138: R138D, R138E, R138G, R138Q, R138H, or R138N; P7 anchor residue at G139: G139D; and/or P9 anchor at residue Q141: Q141D, Q141N, Q141T, Q141E, Q141R, or Q141G.

In addition to modifying one or more anchor residues, it is also possible to modify one or more non-anchor residues in the above-identified clavin, gigantin, mitogillin, and restrictocin T cell epitopes, provided the modified epitope retains reduced MHC class II binding as compared to the corresponding wild type ribotoxin.

In some embodiments, the modified T cell epitope is part of a modified ribotoxin molecule (e.g., modified clavin, gigantin, mitogillin, or restrictocin molecule), where the modified ribotoxin molecule comprises at least one fewer T cell epitope as compared to the corresponding wild type ribotoxin (or at least two fewer T cell epitopes, at least three fewer T cell epitopes, etc.). For example, if the wild type ribotoxin comprises two T cell epitopes, in some embodiments, the modified ribotoxin molecule comprises one T cell epitope or zero T cell epitopes. Or, if the wild type ribotoxin comprises three T cell epitopes, in some embodiments, the modified ribotoxin molecule comprises two T cell epitopes, one T cell epitope, or zero T cell epitopes. Or, if the wild type ribotoxin comprises ten T cell epitopes, in some embodiments, the modified ribotoxin molecule comprises nine T cell epitopes, eight T cell epitopes, seven T cell epitopes, six T cell epitopes, five T cell epitopes, four T cell epitopes, three T cell epitopes, two T cell epitopes, one T cell epitope, or zero T cell epitopes. Or, if the wild type ribotoxin comprises eight T cell epitopes, in some embodiments, the modified ribotoxin molecule comprises seven T cell epitopes, six T cell epitopes, five T cell epitopes, four T cell epitopes, three T cell epitopes, two T cell epitopes, one T cell epitope, or zero T cell epitopes. Or, if the wild type ribotoxin comprises six T cell epitopes, in some embodiments, the modified ribotoxin molecule comprises five T cell epitopes, four T cell epitopes, three T cell epitopes, two T cell epitopes, one T cell epitope, or zero T cell epitopes. Or, if the wild type ribotoxin comprises four T cell epitopes, in some embodiments, the modified ribotoxin molecule comprises three T cell epitopes, two T cell epitopes, one T cell epitope, or zero T cell epitopes.

More specifically, the modified ribotoxin molecule (e.g., modified clavin, gigantin, mitogillin, or restrictocin molecule) may comprise at least one mutation compared with a "parent" ribotoxin, the parent ribotoxin being at least a portion of wild type ribotoxin (e.g., wild type clavin, gigantin, mitogillin, or restrictocin, a fragment of wild type clavin, gigantin, mitogillin, or restrictocin, etc.). In one embodiment, the at least one mutation comprises a mutation of a T cell epitope, e.g., resulting in the epitope having reduced ability to bind to MHC class II molecules or having no ability to bind MHC class II molecules.

More specifically, the modified ribotoxin molecule may comprise at least one mutation compared with a "parent" ribotoxin, the parent ribotoxin being at least a portion of wild type ribotoxin (e.g., wild type clavin, gigantin, mitogillin, or restrictocin, a fragment of wild type clavin, gigantin, mitogillin, or restrictocin, etc.). In one embodiment, the at least one mutation comprises a mutation of a T cell epitope, e.g., resulting in the epitope having reduced ability to bind to MHC class II molecules or having no ability to bind MHC class II molecules. For example, the at least one mutation may be within one or more of the following clavin T cell epitopes (SEQ ID NO:27, SEQ ID NO:28, SEQ ID NO:29, SEQ ID NO:3, and/or SEQ ID NO:5), one or more of the following gigantin T cell epitopes (SEQ ID NO:30, SEQ ID NO:31, SEQ ID NO:32, and/or SEQ ID NO:3), or one or more of the following mitogillin or restrictocin T cell epitopes (SEQ ID NO:33, SEQ ID NO:34, SEQ ID NO:35, SEQ ID NO:36, and/or SEQ ID NO:3).

In some embodiments, the modified clavin molecule comprises at least one mutation compared with a "parent" clavin (e.g., a wild type clavin, a fragment of wild type clavin, etc.), wherein the at least one mutation comprises a mutation of at least one of amino acids Q10, P13, T15, N16, Y18, L63, R66, I69, W71, V122, T125, P127, N128, V130, G133, I134, A136, T138, R139, E140, or Q142 (of wild type clavin).

In other embodiments, the modified gigantin molecule comprises at least one mutation compared with a "parent" gigantin (e.g., a wild type gigantin, a fragment of wild type gigantin, etc.), wherein the at least one mutation comprises a mutation of at least one of amino acids Q10, T15, N16, Y18, L63, R66, I69, F71, V122, T125, P127, N128, V130 (of wild type gigantin).

In other embodiments, the modified mitogillin or restrictocin molecule comprises at least one mutation compared with a "parent" mitogillin or restrictocin (e.g., a wild type mitogillin or restrictocin, a fragment of wild type mitogillin or restrictocin, etc.), wherein the at least one mutation comprises a mutation of at least one of amino acids Q9, P12, T14, N15, Y17, I62, R65, I68, F70, V121, T124, P126, N127, V129, G132, I133, A135, Q137, R138, G139, or Q141 (of wild type mitogillin or restrictocin).

Modification of the wild type clavin, gigantin, mitogillin, or restrictocin may include an amino acid substitution as described above. In some embodiments, the amino acid substitution is a 1 amino acid substitution (e.g., Q10A), a 2 amino acid substitution (e.g., Q10A and Q142G), a 3 amino acid substitution (e.g., Q10A, N16A, Q142G), a 4 amino acid substitution, a 5 amino acid substitution, 6 amino acid substitution, a 7 amino acid substitution, an 8 amino acid substitution, a nine amino acid substitution, a 10 amino acid substitution, or a more than 10 amino acid substitution.

Modification of the wild type clavin, gigantin, mitogillin, or restrictocin is not limited to an amino acid substitution. For example, the modification may include an amino acid deletion or an amino acid addition. In some embodiments, the amino acid deletion is a 1 amino acid deletion, a 2 amino acid deletion, a 3 amino acid deletion, a 4 amino acid deletion, a 5 amino acid deletion, 6 amino acid deletion, a 7 amino acid deletion, an 8 amino acid deletion, a nine amino acid deletion, a 10 amino acid deletion, or a more than 10 amino acid deletion. In some embodiments, the amino acid addition is a 1 amino acid addition, a 2 amino acid addition, a 3 amino acid addition, a 4 amino acid addition, a 5 amino acid addition, 6 amino acid addition, a 7 amino acid addition, an 8 amino acid addition, a nine amino acid addition, a 10 amino acid addition, or a more than 10 amino acid addition. Deletions and/or additions may optionally correspond to deletions in regions of the molecule other than T cell epitope regions.

Ribotoxicity and Cytotoxicity

The modified ribotoxin (e.g., α-sarcin, clavin, gigantin, mitogillin, or restrictocin) molecule may retain the cytotoxicity of the corresponding wild type ribotoxin. Cytotoxicity may refer to ribonucleolytic activity toward a specific substrate, e.g., an oligonucleotide substrate (e.g., the ribosome), ability to interfere with protein synthesis in a cell-based assay, or cell killing activity toward a particular cell type. For example, a cytotoxicity assay may measure the ability of the toxin to degrade the ribosome. Cytotoxicity is not limited to the aforementioned definitions.

In some embodiments, the modified ribotoxin (e.g., α-sarcin, clavin, gigantin, mitogillin, or restrictocin) molecule may be as cytotoxic as the corresponding wild type ribotoxin. In some embodiments, the modified ribotoxin (e.g., α-sarcin, clavin, gigantin, mitogillin, or restrictocin) molecule is at least as cytotoxic as the corresponding wild type ribotoxin. It was surprisingly discovered that in certain embodiments, the modified sarcin molecule was more cytotoxic than wild type α-sarcin. In some embodiments, the modified ribotoxin (e.g., α-sarcin, clavin, gigantin, mitogillin, or restrictocin) molecule is less cytotoxic than the corresponding wild type ribotoxin. In some embodiments, the modified ribotoxin (e.g., α-sarcin, clavin, gigantin, mitogillin, or restrictocin) molecule is no more than 10% less cytotoxic than the corresponding wild type ribotoxin. In some embodiments, the modified ribotoxin (e.g., α-sarcin, clavin, gigantin, mitogillin, or restrictocin) molecule is no more than 15% less cytotoxic than the corresponding wild type ribotoxin. In some embodiments, the modified ribotoxin (e.g., α-sarcin, clavin, gigantin, mitogillin, or restrictocin) molecule is no more than 20% less cytotoxic than the corresponding wild type ribotoxin.

In some embodiments, the modified ribotoxin (e.g., α-sarcin, clavin, gigantin, mitogillin, or restrictocin) molecule retains the core ribotoxin structure of the corresponding wild type ribotoxin. As used herein, the term "core ribotoxin structure" refers to the arrangement of the alpha helix and beta sheet of wild type ribotoxin. For example, in some embodiments, the modified ribotoxin (e.g., α-sarcin, clavin, gigantin, mitogillin, or restrictocin) molecule has the same alpha helix arrangement as the corresponding wild type ribotoxin, e.g., the general structure of the alpha helix remains the same. In some embodiments, the amino acids of the alpha helix remain the same as the wild type ribotoxin. The alpha helix amino acids may refer to Glu27-Ala37 (Perez-Canadilas et al., J Mol Biol 2009, 299:1061-73) or Glu26-Ala36 for mitogillin or restrictocin. In some embodiments, one or more amino acids in the alpha helix may be modified but the alpha helix structure is still maintained. In some embodiments, the modified ribotoxin (e.g., α-sarcin, clavin, gigantin, mitogillin, or restrictocin) molecule has the same beta sheet structure as the corresponding wild type ribotoxin, e.g., the general structure of the beta sheet remains the same. In some embodiments, the amino acids of the beta sheet remain the same as wild type ribotoxin. In some embodiments, one or more amino acids in the alpha helix may be modified but the alpha helix structure is still maintained. The amino acids of the beta sheet may refer to His50-Phe52 and/or Leu94-Phe97 and/or Ala120-Tyr124 and/or Gly 133-Thr138 and/or Glu144-Leu146 (Perez-Canadilas et al., J Mol Biol 2009, 299:1061-73) or His49-Phe51 and/or Leu93-Phe96 and/or Ala119-Tyr123 and/or Gly 132-Gln138 and/or Asp143-Leu146 in mitogillin or restrictocin. In some embodiments, one or more of the amino acids of the active site, e.g., His 50 and/or Glu 96 and/or Arg 121 and/or His137 (or His 49, Glu 95, Arg 120, and/or His 136 in mitogillin or restrictocin) are not changed in the modified ribotoxin molecule. In some embodiments, one or more of the amino acids of the active site are modified.

The modified ribotoxin (e.g., α-sarcin, clavin, gigantin, mitogillin, or restrictocin) molecule may retain the ribotoxicity of the corresponding wild type ribotoxin. Ribotoxicity may refer to ribotoxic (e.g., nucleolytic) activity toward a specific substrate, e.g., oligonucleotide substrate (e.g., the ribosome) or ability to interfere with protein synthesis in a cell-based assay. Ribotoxicity is not limited to the aforementioned definitions.

In some embodiments, the modified ribotoxin (e.g., α-sarcin, clavin, gigantin, mitogillin, or restrictocin) molecule may be as ribotoxic as the corresponding wild type ribotoxin. In some embodiments, the modified ribotoxin (e.g., α-sarcin, clavin, gigantin, mitogillin, or restrictocin) molecule is at least as ribotoxic as the corresponding wild type ribotoxin. It was surprisingly discovered that in certain embodiments, the modified sarcin molecule is more ribotoxic than wild type α-sarcin. In some embodiments, the modified ribotoxin (e.g., α-sarcin, clavin, gigantin, mitogillin, or restrictocin) molecule is less ribotoxic than the corresponding wild type ribotoxin. In some embodiments, the modified ribotoxin (e.g., α-sarcin, clavin, gigantin, mitogillin, or restrictocin) molecule is no more than 10% less ribotoxic than the corresponding wild type ribotoxin. In some embodiments, the modified ribotoxin (e.g., α-sarcin, clavin, gigantin, mitogillin, or restrictocin) molecule is no more than 15% less ribotoxic than the corresponding wild type ribotoxin. In some embodiments, the modified ribotoxin (e.g., α-sarcin, clavin, gigantin, mitogillin, or restrictocin) molecule is no more than 20% less ribotoxic than the corresponding wild type ribotoxin.

Assays for ribotoxicity and cytotoxicity of sarcin are well known in the art and described in Carreras-Sangra et al., 2012, PEDS 25, 425-35. Conventional ribotoxicity and cytotoxicity assays include the in vitro transcription translation (IVTT) assay described in the Examples of this application.

Stability and Solubility

Stability of a protein may determine the ability of the protein to withstand storage or transport conditions. Stability may also affect the protein's half-life after administration (e.g., in serum). The melting temperature of the protein, or the temperature at which the protein loses it tertiary structure, are non-limiting examples of measurements of the physical stability of a protein.

In some embodiments, the modified ribotoxin (e.g., α-sarcin, clavin, gigantin, mitogillin, or restrictocin) molecule retains the melting temperature of the corresponding wild type ribotoxin. (The term "retains the melting temperature" may refer to plus or minus 2%, plus or minus 5%, plus or minus 10%). For example, a modified ribotoxin (e.g., α-sarcin, clavin, gigantin, mitogillin, or restrictocin) molecule retains the melting temperature of the corresponding wild type ribotoxin if its melting temperature is within plus or minus 5% of the melting temperature of the corresponding wild type ribotoxin. In some embodiments, the modified ribotoxin (e.g., α-sarcin, clavin, gigantin, mitogillin, or restrictocin) molecule has a higher melting temperature than the corresponding wild type ribotoxin.

In some embodiments, the modified ribotoxin (e.g., α-sarcin, clavin, gigantin, mitogillin, or restrictocin) molecule has a lower melting temperature than the corresponding wild type ribotoxin. In some embodiments, the modified ribotoxin (e.g., α-sarcin, clavin, gigantin, mitogillin, or restrictocin) molecule has a melting temperature that is no more than 2 degrees less than the melting temperature of the corresponding wild type ribotoxin. In some embodiments, the modified ribotoxin (e.g., α-sarcin, clavin, gigantin, mitogillin, or restrictocin) molecule has a melting temperature that is no more than 5 degrees less than the melting temperature of the corresponding wild type ribotoxin. In some embodiments, the modified ribotoxin (e.g., α-sarcin, clavin, gigantin, mitogillin, or restrictocin) molecule has a melting temperature that is no more than 10 degrees less than the melting temperature of the corresponding wild type ribotoxin.

In some embodiments, the modified ribotoxin (e.g., α-sarcin, clavin, gigantin, mitogillin, or restrictocin) molecule has a melting temperature that is at least 40° C. In some embodiments, the modified ribotoxin (e.g., α-sarcin, clavin, gigantin, mitogillin, or restrictocin) molecule has a melting temperature that is at least 50° C. In some embodiments, the modified ribotoxin (e.g., α-sarcin, clavin, gigantin, mitogillin, or restrictocin) molecule has a melting temperature that is at least 60° C. In some embodiments, the modified ribotoxin (e.g., α-sarcin, clavin, gigantin, mitogillin, or restrictocin) molecule has a melting temperature that is at least 65° C. In some embodiments, the modified ribotoxin (e.g., α-sarcin, clavin, gigantin, mitogillin, or restrictocin) molecule has a melting temperature that is at least 70° C. In some embodiments, the modified ribotoxin (e.g., α-sarcin, clavin, gigantin, mitogillin, or restrictocin) molecule has a melting temperature that is at least 80° C. Protocols for determining melting temperature of such proteins are well known to one of ordinary skill in the art (e.g., see Gong et al., 2009, JBC 284:21, pp 14203-14210, and WO 2009/099961 A2).

In some embodiments, the modified ribotoxin (e.g., α-sarcin, clavin, gigantin, mitogillin, or restrictocin) molecule retains the solubility of the corresponding wild type ribotoxin. (The term "retains the solubility" may refer to plus or minus 2%, plus or minus 5%, plus or minus 10%). For example, a modified ribotoxin (e.g., α-sarcin, clavin, gigantin, mitogillin, or restrictocin) molecule retains the solubility of the corresponding wild type ribotoxin if its solubility is within plus or minus 5% of the solubility of wild type ribotoxin. In some embodiments, the modified ribotoxin (e.g., α-sarcin, clavin, gigantin, mitogillin, or restrictocin) molecule has a higher solubility than the corresponding wild type ribotoxin.

In some embodiments, the modified ribotoxin (e.g., α-sarcin, clavin, gigantin, mitogillin, or restrictocin) molecule has a lower solubility than the corresponding wild type ribotoxin. In some embodiments, the modified ribotoxin (e.g., α-sarcin, clavin, gigantin, mitogillin, or restrictocin) molecule has a solubility that is no more than 10% less than the solubility of the corresponding wild type ribotoxin. In some embodiments, the modified ribotoxin (e.g., α-sarcin, clavin, gigantin, mitogillin, or restrictocin) molecule has a solubility that is no more than 15% less than the solubility of the corresponding wild type ribotoxin. In some embodiments, the modified ribotoxin (e.g., α-sarcin, clavin, gigantin, mitogillin, or restrictocin) molecule has a solubility that is no more than 20% less than the solubility of the corresponding wild type ribotoxin.

In some embodiments, the modified ribotoxin (e.g., α-sarcin, clavin, gigantin, mitogillin, or restrictocin) molecule or fusion protein comprises a tag. A tag may include but is not limited to a His tag, a flag tag, or the like.

Without intending to be bound by any theory or mechanism, it is believed that α-sarcin, clavin, gigantin, mitogillin, and restrictocin are not degraded by serum proteases. They are also believed to be relatively resistant to lysosomal and cytosolic proteases. In some embodiments, the modification(s) to the wild type ribotoxin (e.g., α-sarcin, clavin, gigantin, mitogillin, or restrictocin) molecule to create the modified ribotoxin molecule do not affect the protease resistant properties of wild type ribotoxin. For example, in some embodiments, the modification(s) do not add a protease cleavage site.

In some embodiments, the modified ribotoxin (e.g., α-sarcin, clavin, gigantin, mitogillin, or restrictocin) molecule maintains the protease resistant property of the corresponding wild type ribotoxin (e.g., when subjected to serum proteases and/or lysosomal proteases and/or cytosolic proteases). In some embodiments, the modified ribotoxin (e.g., α-sarcin, clavin, gigantin, mitogillin, or restrictocin) molecule is no more than 10% less protease resistant (e.g., when subjected to serum proteases and/or lysosomal proteases and/or cytosolic proteases) as compared to the corresponding wild type ribotoxin. In some embodiments, the modified ribotoxin (e.g., α-sarcin, clavin, gigantin, mitogillin, or restrictocin) molecule is no more than 20% less protease resistant (e.g., when subjected to serum proteases and/or lysosomal proteases and/or cytosolic proteases) as compared to the corresponding wild type ribotoxin. In some embodiments, the modified ribotoxin (e.g., α-sarcin, clavin, gigantin, mitogillin, or restrictocin) molecule is no more than 30% less protease resistant (e.g., when subjected to serum proteases and/or lysosomal proteases and/or cytosolic proteases) as compared to the corresponding wild type ribotoxin. In some embodiments, the modified ribotoxin (e.g., α-sarcin, clavin, gigantin, mitogillin, or restrictocin) molecule is no more than 40% less protease resistant (e.g., when subjected to serum proteases and/or lysosomal proteases and/or cytosolic proteases) as compared to the corresponding wild type ribotoxin. In some embodiments, the modified ribotoxin (e.g., α-sarcin, clavin, gigantin, mitogillin, or restrictocin) molecule is no more than 50% less protease resistant (e.g., when subjected to serum proteases and/or lysosomal proteases and/or cytosolic proteases) as compared to the corresponding wild type ribotoxin.

Ribotoxin Fusion Proteins

The present invention also features ribotoxin fusion proteins, e.g., ribotoxin fusion proteins comprising a modified ribotoxin (e.g., α-sarcin, clavin, gigantin, mitogillin, or restrictocin) molecule as described above. In some embodiments, the ribotoxin fusion protein comprises a modified ribotoxin (e.g., α-sarcin, clavin, gigantin, mitogillin, or restrictocin) molecule having reduced immunogenicity in humans as compared to the corresponding wild type ribotoxin and a targeting molecule effective for binding a target.

The targeting molecule may be linked to the modified ribotoxin (e.g., α-sarcin, clavin, gigantin, mitogillin, or restrictocin) molecule. In some embodiments, the targeting molecule may be incorporated in the modified ribotoxin (e.g., α-sarcin, clavin, gigantin, mitogillin, or restrictocin) molecule.

In some embodiments, the targeting molecule is linked to the N-terminus of the modified ribotoxin (e.g., α-sarcin, clavin, gigantin, mitogillin, or restrictocin) molecule. In some embodiments, the targeting molecule is linked to the C-terminus of the modified ribotoxin (e.g., α-sarcin, clavin, gigantin, mitogillin, or restrictocin) molecule. In some embodiments, the modified ribotoxin (e.g., α-sarcin, clavin, gigantin, mitogillin, or restrictocin) molecule is linked to the N-terminus of the targeting molecule. In some embodiments, the modified ribotoxin (e.g., α-sarcin, clavin, gigantin, mitogillin, or restrictocin) molecule is linked to the C-terminus of the targeting molecule. In some embodiments, the N-terminus of the targeting molecule is linked to the C-terminus of the modified ribotoxin (e.g., α-sarcin, clavin, gigantin, mitogillin, or restrictocin) molecule. In some embodiments, the N-terminus of the targeting molecule is linked to the N-terminus of the modified ribotoxin (e.g., α-sarcin, clavin, gigantin, mitogillin, or restrictocin) molecule. In some embodiments, the C-terminus of the targeting molecule is linked to the C-terminus of the modified ribotoxin (e.g., α-sarcin, clavin, gigantin, mitogillin, or restrictocin) molecule. In some embodiments, the C-terminus of the targeting molecule is linked to the N-terminus of the modified ribotoxin (e.g., α-sarcin, clavin, gigantin, mitogillin, or restrictocin) molecule.

Linkers

Linkers may optionally be used to link the modified ribotoxin (e.g., α-sarcin, clavin, gigantin, mitogillin, or restrictocin) molecule and the targeting molecule together in a fusion protein. In some embodiments, the targeting molecule is linked to the C-terminus of the modified ribotoxin (e.g., α-sarcin, clavin, gigantin, mitogillin, or restrictocin) molecule via a linker. In some embodiments, the targeting molecule is linked to the N-terminus of the modified ribotoxin (e.g., α-sarcin, clavin, gigantin, mitogillin, or restrictocin) molecule via a linker. In some embodiments, the fusion protein is an oligomer of modified ribotoxin (e.g., α-sarcin, clavin, gigantin, mitogillin, or restrictocin) molecules and targeting molecules. For example, in some embodiments, the fusion protein comprises two targeting molecules and one modified ribotoxin (e.g., α-sarcin, clavin, gigantin, mitogillin, or restrictocin) molecule. In some embodiments, the fusion protein comprises two modified ribotoxin (e.g., α-sarcin, clavin, gigantin, mitogillin, or restrictocin) molecules and one targeting molecule. One or more linkers may optionally be used to link fusion proteins together to form an oligomer or to link components within the fusion protein together.

Linkers may affect the overall structure of the fusion protein and the accessibility of functional regions of the components of the fusion protein. For example, proline residues are known to bend or kink the structure of a protein, and thus a linker comprising one more proline residues may bend or kink the structure of the fusion protein.

A linker, for example, may include but is not limited to a peptide of various amino acid lengths and/or sequences. In some embodiments, the linker is between 0 to 10 amino acids in length. In some embodiments, the linker is between 0 to 15 amino acids in length. In some embodiments, the linker is between 0 to 20 amino acids in length. In some embodiments, the linker is between 1 to 10 amino acids in length. In some embodiments, the linker is between 1 to 15 amino acids in length. In some embodiments, the linker is between 1 to 20 amino acids in length. In some embodiments, the linker is between 2 to 20 amino acids in length. In some embodiments, the linker is between 3 to 20 amino acids in length. In some embodiments, the linker is between 4 to 20 amino acids in length. In some embodiments, the linker is between 5 to 10 amino acids in length. In some embodiments the linker is between 10 to 15 amino acids in length. In some embodiments, the linker is between 15 to 20 amino acids in length. In some embodiments, the linker is more than 20 amino acids in length. The optimal lengths may vary to match the spacing and orientation of the specific target(s).

The linker may be encoded in the gene that encodes the fusion protein. In some embodiments, the linker may be covalently bonded (e.g., cross-linked) to a portion of the fusion protein. The linkers may be covalent or very tight non-covalent linkages; chemical conjugation or direct gene fusions of various amino acid sequences, e.g., those (a) rich in Glycine, Serine, Proline, Alanine, or (b) variants of naturally occurring linking amino acid sequences that connect immunoglobulin domains.

In some embodiments, the linker comprises a non-peptide component (e.g., a sugar residue, a heavy metal ion, a chemical agent such as a therapeutic chemical agent, polyethylene glycols (PEGs), e.g., discrete PEGs, etc.).

In some embodiments, the dPEG is linked to the modified ribotoxin (e.g., α-sarcin, clavin, gigantin, mitogillin, or restrictocin) molecule at either one of a serine, tyrosine, cysteine, or lysine of the modified ribotoxin (e.g., α-sarcin, clavin, gigantin, mitogillin, or restrictocin) molecule. In some embodiments, the dPEG is linked to a glycosylation site of the modified ribotoxin (e.g., α-sarcin, clavin, gigantin, mitogillin, or restrictocin) molecule. In some embodiments, the dPEG is linked to the targeting molecule at either one of a serine, tyrosine, cysteine, or lysine of the targeting molecule. In some embodiments, the dPEG is linked to a glycosylation site of the targeting molecule. In some embodiments, the dPEG is between about 200 to 10,000 daltons.

In some embodiments, the linker is a hinge component. For example, the targeting molecule may comprise a first half hinge component capable of binding a second half hinge component on the modified ribotoxin (e.g., α-sarcin, clavin, gigantin, mitogillin, or restrictocin) molecule. In some embodiments, the hinge components may comprise one or more multimerizing domains. The multimerizing domains may be configured such that they can be cleaved subsequently from the hinge components via proteolysis. Any protease might be used that exhibits sufficient specificity for its particular recognition sequence designed into the linker, but does not cleave any other sequence in the fusion protein. The cleavage may occur at the extreme end of the recognition motif, so that the final fusion protein molecule does not retain any additional amino acid residues that are part of the protease recognition site. The protease may be an enzyme that has little or no effect on a patient if trace amounts were carried over following purification (e.g., Factor X, thrombin).

An example of a cleavable linker (or adapter) can be found in Heisler et al., 2003, Int. J. Cancer 103 277-282 and Keller et al., 2001, J Control Release 74, 259-261. For example, the linker (adapter) comprises a cytosolic cleavable peptide (CCP), membrane transfer peptide (MTP) and endosomal cleavable peptide (ECP). Upon endocytosis of the fusion protein, enzymatic cleavage releases the ligand exposing the MTP, allowing translocation into the cytosol where the MTP is released from the toxin (e.g., sarcin, clavin, gigantin, mitogillin, or restrictocin) by an enzymatic cleavage of the CCP. The ribotoxin fusion proteins described herein may use a similar cleavable linker or various components of such a linker as described in the above references.

As previously discussed, the fusion protein may be an oligomer, e.g., the fusion protein may comprise a targeting molecule dimer (or multiple targeting molecules) linked to a modified ribotoxin (e.g., α-sarcin, clavin, gigantin, mitogillin, or restrictocin) molecule. In some embodiments, the targeting molecule is a dimer. In some embodiments, the targeting molecule is a trimer. In some embodiments, the targeting molecule is a tetramer. In some embodiments, the targeting molecule is a pentamer. In some embodiments, the targeting molecule comprises more than five subunits. In some embodiments, the fusion protein may be an oligomer, e.g., the fusion protein may comprise a modified ribotoxin (e.g., α-sarcin, clavin, gigantin, mitogillin, or restrictocin) molecule dimer (or multiple modified ribotoxin molecules) linked to a targeting molecule. In some embodiments, the modified ribotoxin (e.g., α-sarcin, clavin, gigantin, mitogillin, or restrictocin) molecule is a dimer. In some embodiments, the modified ribotoxin (e.g., α-sarcin, clavin, gigantin, mitogillin, or restrictocin) molecule is a trimer. In some embodiments, the modified ribotoxin (e.g., α-sarcin, clavin, gigantin, mitogillin, or restrictocin) molecule is a tetramer. In some embodiments, the modified ribotoxin (e.g., α-sarcin, clavin, gigantin, mitogillin, or restrictocin) molecule is a pentamer. In some embodiments, the modified ribotoxin (e.g., α-sarcin, clavin, gigantin, mitogillin, or restrictocin) molecule comprises more than five subunits.

The two or multiple targeting molecules or the two or multiple modified ribotoxin (e.g., α-sarcin, clavin, gigantin, mitogillin, or restrictocin) molecules may be coupled by a linker, wherein the linker can be attached to the individual targeting molecules or modified ribotoxin (e.g., α-sarcin, clavin, gigantin, mitogillin, or restrictocin) molecules at any appropriate location. Examples of where a linker may attach onto the targeting molecules include: the C-terminus, the N-terminus, a cysteine preceding or following the C-terminus or N-terminus of the CH2 domain. In some embodiments, a linking of two or more targeting molecules or modified ribotoxin (e.g., α-sarcin, clavin, gigantin, mitogillin, or restrictocin) molecules (e.g., to form a dimer, a trimer, etc.) is driven by the formation of a disulfide bond between cysteines.

In some embodiments, a linker may be selected from the group consisting of 2-iminothiolane, N-succinimidyl-3-(2-pyridyldithio) propionate (SPDP), 4-succinimidyloxycarbonyl-α-(2-pyridyldithio)toluene (SMPT), m-maleimidobenzoyl-N-hydroxysuccinimide ester (MBS), N-succinimidyl (4-iodoacetyl)aminobenzoate (SIAB), succinimidyl 4-(p-maleimidophenyl)but-yrate (SMPB), 1-ethyl-3-(3-dimethylaminopropyl)carbodiimide (EDC), bis-diazobenzidine and glutaraldehyde. In some embodiments, a linker may be attached to an amino group, a carboxylic group, a sulfhydryl group or a hydroxyl group of an amino acid group. The amino group that a linker may attach to includes, for example, alanine, lysine, or proline. The carboxylic group that a linker may be attached to may be, for example, aspartic acid, glutamic acid. The sulfhydryl group that a linker may be attached to may be, for example, cysteine. The hydroxyl group that a linker may be attached to may be, for example, serine, threonine, or tyrosine. Any coupling chemistry known to those skilled in the art capable of chemically attaching targeting molecule to another targeting molecule (or a targeting molecule to a modified ribotoxin molecule) can be used.

Targeting Molecule and Targets

The fusion protein comprises targeting molecules effective for binding a target. In some embodiments, the targeting molecule comprises a peptide. In some embodiments, the targeting molecule comprises an antibody, an antibody fragment, a single chain variable fragment (scFv), a nanobody, an abdurin, a CH2 domain molecule, a CH2 domain fragment, a CH3 domain molecule, a CH3 domain fragment, a protein scaffold, a hormone, a receptor-binding peptide, the like, or a combination thereof. In some embodiments, the targeting molecule comprises a binding moiety, the binding moiety comprises a VH domain, a VL domain, a tenth type three domain of fibronectin, a designed ankyrin repeat protein, a centyrin scaffold, a peptide ligand, a protein ligand, a receptor, hormone, an enzyme, a cytokine, a small molecule, a fragment thereof, the like, or a combination thereof. The targeting molecule is not limited to the aforementioned examples.

In some embodiments, the targeting molecule comprises an antigen binding region. In some embodiments, the targeting molecule is a CH2 domain molecule having a molecular weight less than about 20 kDa. In some embodiments, the targeting molecule comprises at least one functional FcRn binding site. In some embodiments, the targeting molecule comprises multiple FcRn binding sites (e.g., for enhanced serum half life).

In some embodiments, the ribotoxin (e.g., α-sarcin, clavin, gigantin, mitogillin, or restrictocin) fusion protein is a monospecific molecule, e.g., the ribotoxin fusion protein is specific for one target. In some embodiments, the ribotoxin fusion protein is a bispecific molecule, e.g., the ribotoxin fusion protein is specific for two targets. In some embodiments, the ribotoxin fusion protein is a trispecific molecule, e.g., the ribotoxin fusion protein is specific for three targets.

In some embodiments, the ribotoxin fusion protein is specific for more than three targets.

In some embodiments, the targeting molecule comprises at least a first paratope specific for a first epitope. In some embodiments, the targeting molecule comprises at least two first paratopes each specific for a first epitope. In some embodiments, the targeting molecule comprises a first paratope specific for a first epitope and a second paratope specific for a second epitope.

As previously discussed, the ribotoxin (e.g., α-sarcin, clavin, gigantin, mitogillin, or restrictocin) fusion protein may further comprise at least one additional targeting molecule. For example, in some embodiments, ribotoxin fusion protein further comprises a second targeting molecule, e.g., linked to either the targeting molecule or the modified ribotoxin (e.g., α-sarcin, clavin, gigantin, mitogillin, or restrictocin) molecule. In some embodiments, the ribotoxin fusion protein further comprises a third targeting molecule. In some embodiments, the ribotoxin fusion protein further comprises a fourth targeting molecule.

In some embodiments, the second targeting molecule is linked to the N-terminus of the modified ribotoxin (e.g., α-sarcin, clavin, gigantin, mitogillin, or restrictocin) molecule and the targeting molecule is linked to the C-terminus of the modified ribotoxin (e.g., α-sarcin, clavin, gigantin, mitogillin, or restrictocin) molecule.

In some embodiments, the second targeting molecule is linked to the C-terminus of the modified ribotoxin (e.g., α-sarcin, clavin, gigantin, mitogillin, or restrictocin) molecule and the targeting molecule is linked to the N-terminus of the modified ribotoxin (e.g., α-sarcin, clavin, gigantin, mitogillin, or restrictocin) molecule.

In some embodiments, the second targeting molecule comprises a first paratope specific for the first epitope. In some embodiments, the second targeting molecule comprises a second paratope specific for a second epitope. In some embodiments, the targeting molecule comprises a third paratope specific for the first epitope or a fourth paratope specific for a third epitope.

As previously discussed, the ribotoxin fusion protein may further comprise at least one additional modified ribotoxin (e.g., α-sarcin, clavin, gigantin, mitogillin, or restrictocin) molecule. For example, in some embodiments, ribotoxin fusion protein further comprises a second modified ribotoxin (e.g., α-sarcin, clavin, gigantin, mitogillin, or restrictocin) molecule. In some embodiments, the second modified ribotoxin (e.g., α-sarcin, clavin, gigantin, mitogillin, or restrictocin) molecule is linked to the modified ribotoxin molecule. In some embodiments, the second modified ribotoxin (e.g., α-sarcin, clavin, gigantin, mitogillin, or restrictocin) molecule is linked to the targeting molecule.

The target may be any appropriate target. A target may include a cell, a tumor cell, an immune cell, a protein, a peptide, a molecule, a bacterium, a virus, a protist, a fungus, the like or a combination thereof. For example, in some embodiments, a target is a receptor, e.g., a cell surface receptor. Non-limiting examples of specific targets include Her2 receptor, PMSA, nucleolin, death receptors (e.g., Fas receptor, tumor necrosis factor receptors, etc.), CD22, CD19, CD79b, DR5, ephA2, Muc1, EGFR, VEGFRs, CTLA-4, bacterial and fungal cell surface receptors, CD80, and the like.

In some embodiments, the ribotoxin (e.g., α-sarcin, clavin, gigantin, mitogillin, or restrictocin) fusion protein further comprises an imaging reagent, an isotope, a drug, an immunoconjugate, the like, or a combination thereof. The imaging reagent, isotope, drug, or immunoconjugate may be linked to the modified ribotoxin (e.g., α-sarcin, clavin, gigantin, mitogillin, or restrictocin) molecule and/or the targeting molecule.

Cell Permeability and Retention

It may be beneficial for the modified ribotoxin (e.g., α-sarcin, clavin, gigantin, mitogillin, or restrictocin) molecule (e.g., of a ribotoxin fusion protein) to lack membrane permeability (or have reduced membrane permeability as compared to wild type ribotoxin). This may allow the modified ribotoxin (e.g., α-sarcin, clavin, gigantin, mitogillin, or restrictocin) molecule to be administered more safely to patients. For example, if the modified ribotoxin (e.g., α-sarcin, clavin, gigantin, mitogillin, or restrictocin) molecule (e.g., of a ribotoxin fusion protein) were to be cleaved from the targeting molecule, the modified ribotoxin (e.g., α-sarcin, clavin, gigantin, mitogillin, or restrictocin) molecule would not be taken up (or would be less likely to be taken up) by a cell that is not the intended target cell (according to the specificity of the targeting molecule of the ribotoxin fusion protein). In some embodiments, the modified ribotoxin (e.g., α-sarcin, clavin, gigantin, mitogillin, or restrictocin) molecule comprises a mutation in one or more amino acids important in membrane interaction. For example, in some embodiments, the modified ribotoxin (e.g., α-sarcin, clavin, gigantin, mitogillin, or restrictocin) molecule comprises a mutation in amino acid R120 or R121. In some embodiments, the modified ribotoxin (e.g., α-sarcin, clavin, gigantin, mitogillin, or restrictocin) molecule comprises the mutation R120Q or R121Q. In some embodiments, the modified ribotoxin molecule comprises the mutation R120S or R121S.

The membrane permeability mutation may not necessarily be coupled with a mutation in a T cell epitope site. However, in some embodiments, the membrane permeability mutation is coupled with one or multiple mutations in a T cell epitope site (mutations described above)

In some embodiments, the modified ribotoxin (e.g., α-sarcin, clavin, gigantin, mitogillin, or restrictocin) molecule comprises a mutation that reduced its membrane permeability but does not reduce its cytotoxicity. In some embodiments, the modified ribotoxin (e.g., α-sarcin, clavin, gigantin, mitogillin, or restrictocin) molecule comprises a mutation that reduced its membrane permeability but does not reduce its ribotoxicity (e.g., targeting and/or binding to the SRL site of the ribosome is not affected).

In some embodiments, a molecule is bound to the N terminus of the modified ribotoxin (e.g., α-sarcin, clavin, gigantin, mitogillin, or restrictocin) molecule (e.g., of a ribotoxin fusion protein), wherein the molecule can be cleaved upon uptake of the modified sarcin molecule in a target cell.

The modified ribotoxin (e.g., α-sarcin, clavin, gigantin, mitogillin, or restrictocin) molecule having reduced membrane permeability is not limited to the R120Q, R120S, R121Q, or R121S mutations. For example, the first 22 amino acids of α-sarcin, gigantin, or clavin or the first 21 amino acids of restrictocin or mitogillin may be important for membrane interaction (and trafficking to the rRNA sarcin-rich loop target site). In some embodiments, one or more of the first 21 or 22 amino acids of the ribotoxin (e.g., α-sarcin, clavin, gigantin, mitogillin, or restrictocin) are modified to alter membrane interaction. For example, in some embodiments, the modified ribotoxin (e.g., α-sarcin, clavin, gigantin, mitogillin, or restrictocin) molecule comprises a deletion in the first 5 amino acids, a deletion in the first 10 amino acids, a deletion in the first 15 amino acids, a deletion in the first 20 amino acids, a deletion in the first 22 amino acids.

In some embodiments, one or more of the amino acids in SEQ ID NO: 38 may be modified, e.g., deleted, substituted. Alternatively, amino acids may be added to the N-terminus (e.g., a tag, etc.) to help eliminate (or reduce) membrane permeability.

The ribotoxin fusion protein may have enhanced properties (e.g., enhanced cell retention) as compared to the wild type ribotoxin (e.g., α-sarcin, clavin, gigantin, mitogillin, or restrictocin) ribotoxin (e.g., α-sarcin, clavin, gigantin, mitogillin, or restrictocin) alone, the modified ribotoxin (e.g., α-sarcin, clavin, gigantin, mitogillin, or restrictocin) molecule alone, and/or the targeting molecule alone. For example, in some embodiments, the targeting molecule is modified to enhance its cell permeability. In some embodiments, the ribotoxin is modified to reduce its cell permeability (as described above). In some embodiments, the targeting molecule is modified to enhance cell permeability and the ribotoxin is modified to reduce its cell permeability.

In some embodiments, the fusion protein has increased cell permeability as compared to the targeting molecule alone. In some embodiments, the fusion protein has increased cell permeability as compared to the modified ribotoxin (e.g., α-sarcin, clavin, gigantin, mitogillin, or restrictocin) molecule alone. In some embodiments, the fusion protein is modified to increase cell permeability as compared to wild type ribotoxin. In some embodiments, the fusion protein is modified to increase cell permeability as compared to the targeting molecule alone. In some embodiments, the fusion protein is modified to increase cell permeability as compared to the modified ribotoxin (e.g., α-sarcin, clavin, gigantin, mitogillin, or restrictocin) molecule alone. In some embodiments, the fusion protein has increased cell retention as compared to wild type ribotoxin (e.g., α-sarcin, clavin, gigantin, mitogillin, or restrictocin).

In some embodiments, the fusion protein has increased cell retention as compared to the targeting molecule alone. In some embodiments, the fusion protein has increased cell retention as compared to the modified ribotoxin (e.g., α-sarcin, clavin, gigantin, mitogillin, or restrictocin) molecule alone. In some embodiments, the fusion protein is modified to increase cell retention as compared to wild type ribotoxin (e.g., α-sarcin, clavin, gigantin, mitogillin, or restrictocin). In some embodiments, the fusion protein is modified to increase cell retention as compared to the targeting molecule alone. In some embodiments, the fusion protein is modified to increase cell retention as compared to the modified ribotoxin (e.g., α-sarcin, clavin, gigantin, mitogillin, or restrictocin) molecule alone.

The ribotoxin fusion protein may comprise a means (e.g., a linker) of allowing it to escape from the endosomes. In some embodiments, the linker is designed to be cleaved in the cytosol. In some embodiments, the linker cannot be cleaved in the blood, e.g., serum.

Expression

The modified ribotoxin (e.g., α-sarcin, clavin, gigantin, mitogillin, or restrictocin) molecule and/or the ribotoxin fusion protein may be expressed in any appropriate expression system. For example, in some embodiments, the modified ribotoxin (e.g., α-sarcin, clavin, gigantin, mitogillin, or restrictocin) molecule and/or the ribotoxin fusion protein is expressed in an *E. coli* expression system. In some embodiments, the modified ribotoxin (e.g., α-sarcin, clavin, gigantin, mitogillin, or restrictocin) molecule and/or the ribotoxin fusion protein is expressed in a *Pichia pastoris* expression system.

Pharmaceutical Compositions

In some embodiments, the modified ribotoxin (e.g., α-sarcin, clavin, gigantin, mitogillin, or restrictocin) molecule comprises or is contained in a pharmaceutical composition. In some embodiments, the fusion protein comprises or is contained in a pharmaceutical composition. Examples of pharmaceutical compositions for antibodies and peptides are well known to one of ordinary skill in the art and are described below.

In some embodiments, the modified ribotoxin (e.g., α-sarcin, clavin, gigantin, mitogillin, or restrictocin) molecule or the fusion protein is bound to a molecule (or molecules) that confers increased stability (e.g., serum half-life). Dextrans, various polyethylene glycols (PEG), and albumin-binding peptides are extremely common scaffolds for this purpose (see, for example, Dennis et al., 2002, Journal of Biological Chemistry 33:238390). The molecules may be conjugated to the modified ribotoxin (e.g., α-sarcin, clavin, gigantin, mitogillin, or restrictocin) molecule or the fusion protein by a variety of mechanisms, for example via chemical treatments and/or modification of the protein structure, sequence, etc (see, for example, Ashkenazi et al., 1997, Current Opinions in Immunology 9:195-200; U.S. Pat. No. 5,612,034; U.S. Pat. No. 6,103,233). The molecule (e.g., dextran, PEG, etc.) may be bound to the modified ribotoxin (e.g., α-sarcin, clavin, gigantin, mitogillin, or restrictocin) molecule or the fusion protein through a reactive sulfhydryl by incorporating a cysteine at the end of the protein opposite the binding loops. Such techniques are well known in the art. In another example, a modified ribotoxin (e.g., α-sarcin, clavin, gigantin, mitogillin, or restrictocin) molecule or a fusion protein may bind specifically to albumin to utilize the albumin in serum to increase circulating half-life.

Choosing pharmaceutical compositions that confer increased protein stability or binding of the modified ribotoxin (e.g., α-sarcin, clavin, gigantin, mitogillin, or restrictocin) molecule or the fusion protein to scaffolds that confer increased protein stability are not the only ways in which the stability of the protein can be improved. In some embodiments, the modified ribotoxin (e.g., α-sarcin, clavin, gigantin, mitogillin, or restrictocin) molecule or the fusion protein of the present invention may be modified to alter stability. The term "modified" or "modification" in this context can include one or more mutations, additions, deletions, substitutions, disulfide bond additions, physical alteration (e.g., cross-linking modification, covalent bonding of a component, post-translational modification, e.g., acetylation, glycosylation, pegylation, the like, or a combination thereof), the like, or a combination thereof. Gong et al. (2009, Journal of Biological Chemistry 284:14203-14210) shows examples of modified proteins having increased stability.

Due to the unstable nature of proteins, pharmaceutical compositions are often transported and stored via cold chains, which are temperature-controlled uninterrupted supply chains. For example, some pharmaceutical compositions may be stored and transported at a temperature between about 2 to 8 degrees Celsius. Cold chains dramatically increase the costs of such pharmaceutical compositions. Without intending to be bound by any theory or mechanism, it is believed that increasing the stability of the modified ribotoxin (e.g., α-sarcin, clavin, gigantin, mitogillin, or restrictocin) molecules or the fusion proteins of the present invention (e.g., via pharmaceutical compositions, etc.) may help reduce or eliminate the need to store and transport the modified ribotoxin (e.g., α-sarcin, clavin, gigantin, mitogillin, or restrictocin) molecules or the fusion proteins via cold chains.

The pharmaceutical carrier (vehicles) may be a conventional but is not limited to a conventional carrier (vehicle). For example, E. W. Martin, Remington's Pharmaceutical Sciences, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21st Edition (2006) describe compositions and formulations suitable for pharmaceutical delivery of one or more therapeutic compounds or molecules, such as one or more antibodies, and additional pharmaceutical agents. U.S. Pat. No. 7,648,702 features an aqueous pharmaceutical composition suitable for long-term storage of polypeptides containing an Fc domain of an immunoglobulin.

Pharmaceutical compositions may comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), amino acids (e.g., arginine, cysteine, histidine, glycine, serine, lysine, alanine, glutamic acid, proline), sodium chloride, potassium chloride, sodium citrate, sucrose, glucose, mannitol, lactose, glycerol, xylitol, sorbitol, maltose, inositol, trehalose, bovine serum albumin (BSA), albumin (e.g., human serum albumin, recombinant albumin), dextran, PVA, hydroxypropyl methylcellulose (HPMC), polyethyleneimine, gelatin, polyvinylpyrrolidone (PVP), hydroxyethylcellulose (HEC), polyethylene glycol (PEG), ethylene glycol, dimethylsulfoxide (DMSO), dimethylformamide (DMF), hydrochloride, sacrosine, gamma-aminobutyric acid, Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof. The present invention is in no way limited to the pharmaceutical composition components disclosed herein, for example pharmaceutical compositions may comprise propellants (e.g., hydrofluoroalkane (HFA)) for aerosol delivery. U.S. Pat. No. 5,192,743 describes a formulation that when reconstituted forms a gel which can improve stability of a protein of interest (e.g., for storage).

Pharmaceutical compositions may be appropriately constructed for some or all routes of administration, for example topical administration (including inhalation and nasal administration), oral or enteral administration, intravenous or parenteral administration, transdermal administration, epidural administration, and/or the like. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, a parenteral formulation may comprise injectable fluids that include pharmaceutically and physiologically acceptable fluids such as water, physiological saline, balanced salt solutions, aqueous dextrose, glycerol or the like as a vehicle. As a non-limiting example, the formulation for injectable trastuzumab includes L-histidine HCl, L-histidine, trehalose dihydrate and polysorbate 20 as a dry powder in a glass vial that is reconstituted with sterile water prior to injection. Other formulations of antibodies and proteins for parenteral or subcutaneous use are well known in the art. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. The aforementioned pharmaceutical compositions and protein modifications to increase protein stability can be applied as described in U.S. Patent Application 2009/032692, which is hereby incorporated by reference in its entirety.

Methods of Producing Modified Ribotoxin Molecules and Fusion Proteins

Methods for producing modified ribotoxin (e.g., α-sarcin, clavin, gigantin, mitogillin, or restrictocin) molecules and fusion proteins described herein are well known to one of ordinary skill in the art. For example, the modified ribotoxin (e.g., α-sarcin, clavin, gigantin, mitogillin, or restrictocin) molecules may be expressed in a bacterial system (e.g., including but not limited to *Escherichia coli*; Henze et al., *Eur J Biochem* 192: 127-131, 1990), a yeast system, a phage display system, an insect system, a mammalian system, a ribosomal display, a cis display system (Odegrip et al., 2004, PNAS 101, 2806-2810), the like, or a combination thereof. Construction of fusion proteins with sarcin in a *P. pastoris* expression system has been described in Carreras-Sangra et al., 2012, PEDS 25, 425-35. The present invention is not limited to the methods (e.g., protein expression and display systems) described herein. Briefly, as an example, the method may comprise obtaining a vector having a sequence for a modified ribotoxin (e.g., α-sarcin, clavin, gigantin, mitogillin, or restrictocin) molecule; producing a protein product of the sequence for the modified ribotoxin (e.g., α-sarcin, clavin, gigantin, mitogillin, or restrictocin) molecule in an expression system; and at least partially purifying the protein product.

The present invention also features a modified ribotoxin (e.g., α-sarcin, clavin, gigantin, mitogillin, or restrictocin) molecule having reduced immunogenicity as compared to the corresponding wild type ribotoxin (e.g., α-sarcin, clavin, gigantin, mitogillin, or restrictocin) produced from methods described herein (e.g., see Examples below). As discussed above, the modified ribotoxin (e.g., α-sarcin, clavin, gigantin, mitogillin, or restrictocin) optionally has enhanced solubility and stability and/or reduced membrane permeability or enhanced cell retention as compared to the corresponding wild type ribotoxin (e.g., α-sarcin, clavin, gigantin, mitogillin, or restrictocin) and can be produced from the methods described herein.

Treating or Managing Diseases with Ribotoxin Fusion Proteins

The modified ribotoxin (e.g., α-sarcin, clavin, gigantin, mitogillin, or restrictocin) molecules of the present disclosure may be important tools for treating or managing diseases or conditions. The present disclosure also provides methods of treating or managing a disease or a condition (e.g., in a mammal, e.g., a human). The methods may comprise obtaining a modified ribotoxin (e.g., α-sarcin, clavin, gigantin, mitogillin, or restrictocin) molecule (or fusion protein comprising the same) and introducing the modified ribotoxin molecule or fusion protein into a patient, wherein the modified ribotoxin molecule or fusion protein binds to a target and the binding functions to cause neutralization or destruction of the target.

Optionally, the modified ribotoxin (e.g., α-sarcin, clavin, gigantin, mitogillin, or restrictocin) molecule (or fusion protein comprising the same) binds to a first or second target that causes either activation or inhibition of a signaling event through that target. The modified ribotoxin molecule or fusion protein comprising the same may comprise an agent (e.g., chemical, peptide, toxin) that functions to neutralize or destroy the first target. In some embodiments, the agent is inert or has reduced activity when it is constructed as the modified ribotoxin molecule or fusion protein comprising the same and the agent may be activated or released upon uptake or recycling.

Binding of the modified ribotoxin (e.g., α-sarcin, clavin, gigantin, mitogillin, or restrictocin) molecule (or fusion protein comprising the same) fusion protein may function to cause the neutralization or destruction of the target. The target may be, for example, a cell, a tumor cell, an immune cell, a protein, a peptide, a molecule, a bacterium, a virus, a protist, a fungus, the like, or a combination thereof. The target is not limited to the aforementioned examples. As an example, destruction of a target cell (in this example a tumor) may be achieved by therapy using the following fusion protein: a modified ribotoxin (e.g., α-sarcin, clavin, gigantin, mitogillin, or restrictocin) molecule and a targeting molecule comprising a CH2 domain molecule directed to a particular tumor surface antigen (such as an EGFR, IGFR, nucleolin, ROR1, CD20, CD19, CD22, CD79a, stem cell markers).

In some embodiments, the fusion protein can bind to an immune effector cell surface antigen (for example, a T cell specific antigen like CD3, or an NK cell specific surface antigen, like FcγRIIIa).

Various methods may be used for detecting the binding of the fusion protein (e.g., targeting molecule) to the target in the sample. Such methods are well known to one of ordinary skill in the art.

DNA Sequences and Constructs

While not explicitly described, the present invention also features isolated DNA sequences and recombinant constructs for production of the modified ribotoxin (e.g., α-sarcin, clavin, gigantin, mitogillin, or restrictocin) molecules and fusion proteins described herein. DNA sequences can be codon-optimized for the various expression hosts.

Example 1

Mapping of T Cell Epitopes in α-Sarcin

The following example is a method describing the mapping of potential T cell epitopes in α-sarcin.

Overlapping peptides derived from the 150 amino acid α-sarcin toxin sequence (and peptides for a null mutation to allow expression and testing of the lead deimmunized α-sarcin toxin variants) were tested using EpiScreen™ T cell epitope mapping technology (Antitope Ltd, Cambridge, UK). EpiScreen™ is a highly accurate and sensitive human ex vivo T cell assay technology used to determine helper CD4+ T cell responses to whole proteins, peptides, formulations and NCEs (New Chemical Entities).

The EpiScreen™ T cell epitope mapping technology protocol uses 15mer peptides overlapping by 12 amino acids. The use of 15-mer peptides will help identify the location of T cell epitopes. For the present study, 46 15-mer peptides were used. In addition, two sets of 5 peptides spanning null mutants E96Q and H137Q were tested.

The 15-mer α-sarcin peptides were tested for proliferation against 50 healthy PBMC donors who were selected to best represent the spread of HLA-DR alleles in the population. FIG. 1. CD8+ T cells in the PBMC samples were depleted to exclude the detection of MHC class I restricted T cell responses. PBMC from each donor were thawed, counted and viability was assessed. Cells were revived in room temperature AIM VR culture medium (Invitrogen, Paisley, UK) before adjusting the cell density to 2-3×106 PBMC/ml (proliferation cell stock). Peptides were synthesized on a 1-3 mg scale with free N-terminal amine and C-terminal carboxylic acid. Peptides were dissolved in DMSO to a concentration of 10 mM and peptide culture stocks prepared by diluting into AIM VR culture medium to a final concentration of 5 μM in the well. For each peptide and each donor, sextuplicate cultures were established in a flat bottomed 96 well plate. Both positive and negative control cultures were also tested in sextuplicate. For each donor, three controls (KLH protein and peptides derived from IFV and EBV) were also included. For a positive control, PHA (Sigma, Dorset, UK) was used at a final concentration of 2.5 μg/ml.

Cultures were incubated for a total of 6 days before adding 0.75 μCi 3[H]-thymidine (Perkin ElmerR, Beaconsfield, UK) to each well. Cultures were incubated for a further 18 hours before harvesting onto filter mats using a TomTec Mach III cell harvester. Cpm for each well were determined by Meltilex™ (Perkin ElmerR, Beaconsfield, UK) scintillation counting on a Microplate Beta Counter (Perkin ElmerR, Beaconsfield, UK in paralux, low background counting mode.

Data were presented as non-adjusted (all replicates) and adjusted (removing outliers) and analyzed using previously validated assay parameters. Peptides were considered positive if the number of responding donors (stimulation index (SI) of ≥2.0) was greater than the average response for the complete dataset plus 2× standard deviation (6.6% in both data sets), where SI=mean cpm of test wells/mean cpm medium control wells. Data presented in this way is indicated as SI ≥2.00, p<0.05. Significance (p<0.05) of the response by comparing cpm of test wells against medium control wells using unpaired two sample Students t-test.

Figure 2:
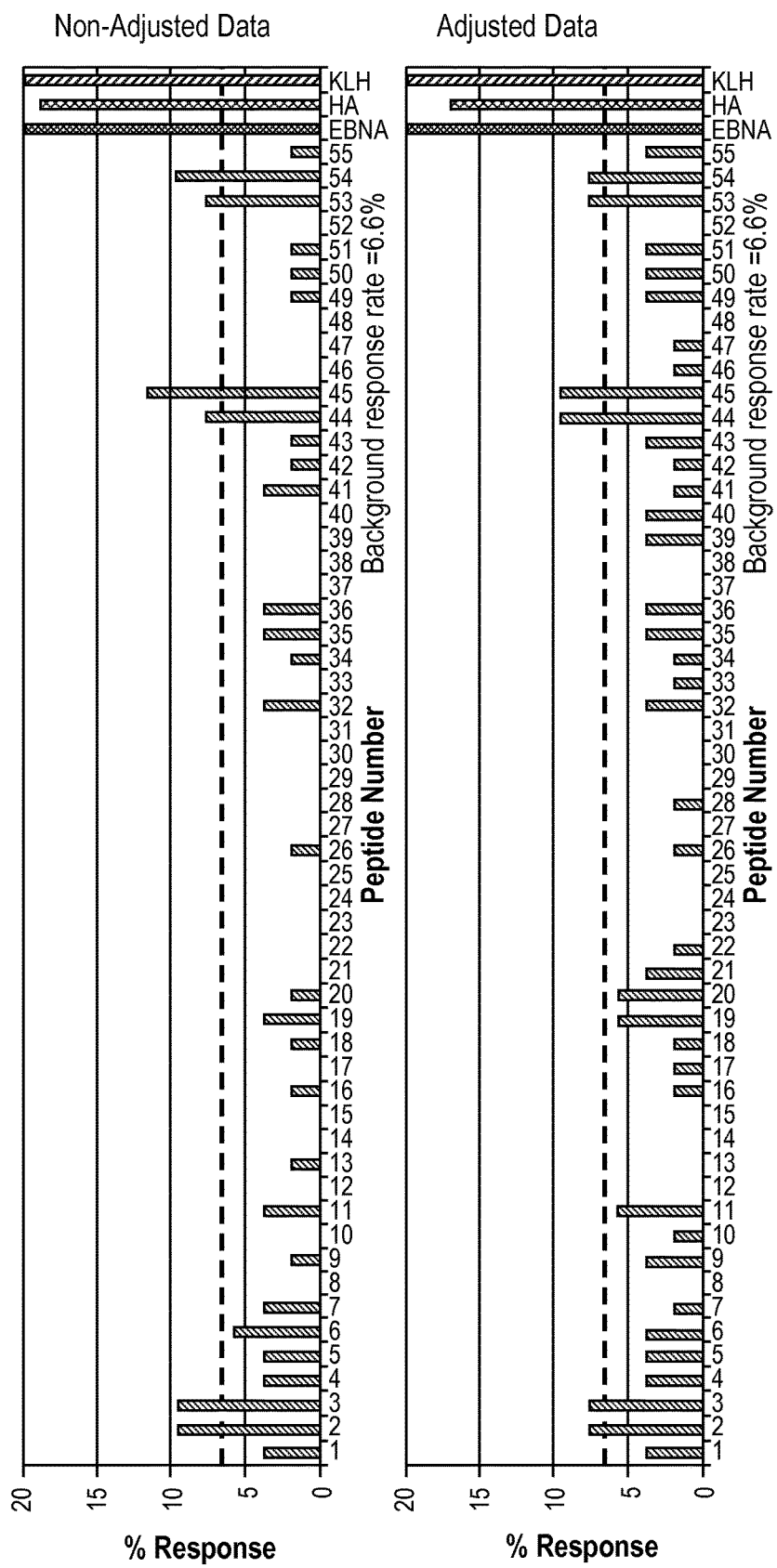
FIG. 2 shows the results of the EpiScreen™ assay, testing 46 15-mer peptides overlapping by 12 amino acids spanning the sarcin sequence and two sets of 5 peptides spanning null mutants E96Q and H137Q. Each peptide was tested in sextuplicate cultures and the data were presented as non-adjusted (all replicates) or adjusted (minus outliers). Peptides were considered positive where the number of responding donors (SI>2) was greater than the average response for the complete dataset plus 2×SD (6.6% in both data sets).

The results of the EpiScreen™ (Antitope Ltd, Cambridge, UK) T cell epitope mapping of α-sarcin are shown in FIG. 2. Two T cell epitopes were identified, one located within the N-terminal 22 amino acid region involved in membrane interaction and binding of sarcin to the ribosome ("Sarcin Epitope 1") and the other spanning H137, which is part of the catalytic triad ("Sarcin Epitope 2"). For Sarcin Epitope 1, an alignment of peptides 2, 3, and 4, as shown below, revealed a predicted HLA-DQ core 9mer binding register corresponding to amino acids 10-18 of α-sarcin (SEQ ID NO:5).

```
Peptide 2:
                                      (SEQ ID NO: 37)
WTCLNDQKNPKTNKY

Peptide 3:
                                      (SEQ ID NO: 38)
LNDQKNPKTNKYETK Peptide 4:
                                      (SEQ ID NO: 39)
QKNPKTNKYETKRLL
```

Peptides 2 and 3 stimulated positive T cell responses in both the non-adjusted and adjusted data sets. Peptide 4 did not elicit a significant T cell response. This was likely due to the lack of a P-1 residue in that peptide (residue 9 of wild type α-sarcin), which supports peptide binding to HLA-DQ.

For Sarcin Epitope 2, an alignment of peptides 44, 45, 53, and 54 (peptides 53 and 54 were derived from the H137 null mutant), as shown below, revealed a second T cell epitope, a predicted HLA-DR core 9-mer binding register corresponding to amino acids 134-142 of wild type α-sarcin (SEQ ID NO:4).

Peptide 44:
VFCG*IIAHTKENQ*GE
(SEQ ID NO: 40)

Peptide 45:
G*IIAHTKENQ*GELKL
(SEQ ID NO: 41)

Peptide 53:
VFCG*IIAQTKENQ*GE
(SEQ ID NO: 42)

Peptide 54:
G*IIAQTKENQ*GELKL
(SEQ ID NO: 43)

Peptides 44, 45, 53, and 54 stimulated positive T cell responses in both the non-adjusted and adjusted data sets. This epitope spans the catalytic residue H137, and peptides containing the null mutation H137Q are also immunogenic.

Example 2

Design of Single Epitope Variants of Alpha Sarcin

The following example describes the design of single epitope variants of α-sarcin.

Individual single epitope variants of α-sarcin were designed in such a way that the immunogenic regions, identified by T cell epitope mapping, were modified to reduce or eliminate the immunogenicity of the wild type α-sarcin protein while retaining its cytotoxic function. Design of such variants was assisted by computer modeling of α-sarcin protein structure. Constraints on modification of α-sarcin at certain locations were considered and appropriate amino acid changes (taking into consideration secondary and tertiary protein structures as well as potential interactions of amino acid side chains with the core of the protein) were designed for removal of T cell epitopes from α-sarcin toxin. Selection of specific amino acid changes were influenced by the available biophysical and biochemical data, particularly where amino acids are located that may contribute to known or predicted functions of α-sarcin toxin and also to the correct folding of α-sarcin.

A number of single amino acid mutations both within and immediately adjacent to (P-1, the amino acid directly N-terminal to the epitope) the two T cell epitopes identified in Example 1 (SEQ ID NO:5 and SEQ ID NO:4) were generated and the toxic activity was assessed in an in vitro transcription translation (IVTT) assay.

Figure 3A:
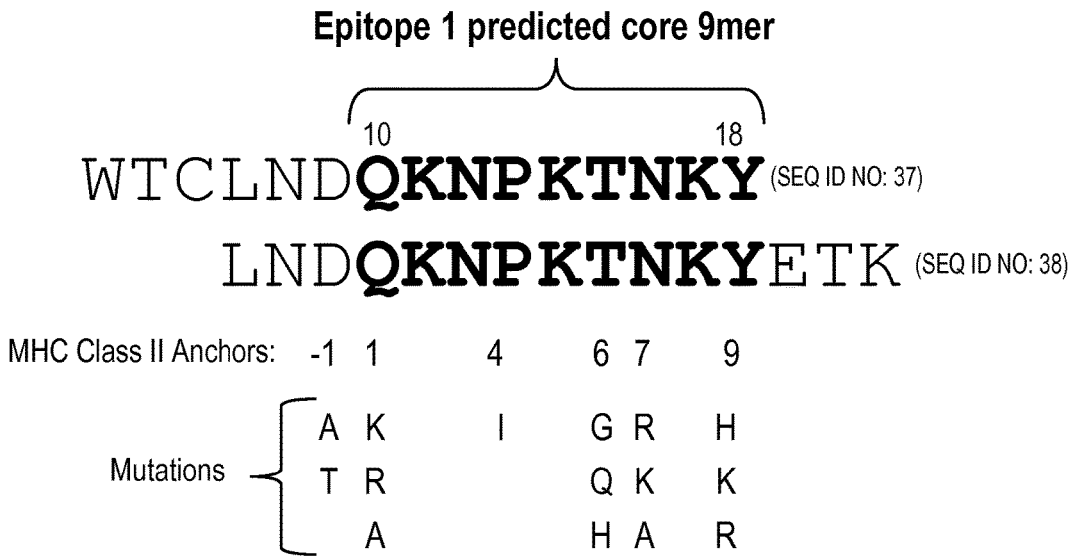
FIGS. 3A-B show epitopes identified by EpiScreen™ T Cell epitope mapping of α-sarcin toxin and single amino acid variants. A) Epitope 1 (residues 10-18) and (FIG. 3A discloses SEQ ID NOS 51 and 53, respectively, in order of appearance, and their corresponding mutant sequences as SEQ ID NOS 52 and 54, respectively) B) Epitope 2 (residues 134-142) (FIG. 3B discloses SEQ ID NOS 55 and 57, respectively, in order of appearance, and their corresponding mutant sequences as SEQ ID NOS 56 and 58, respectively).
Figure 3B:
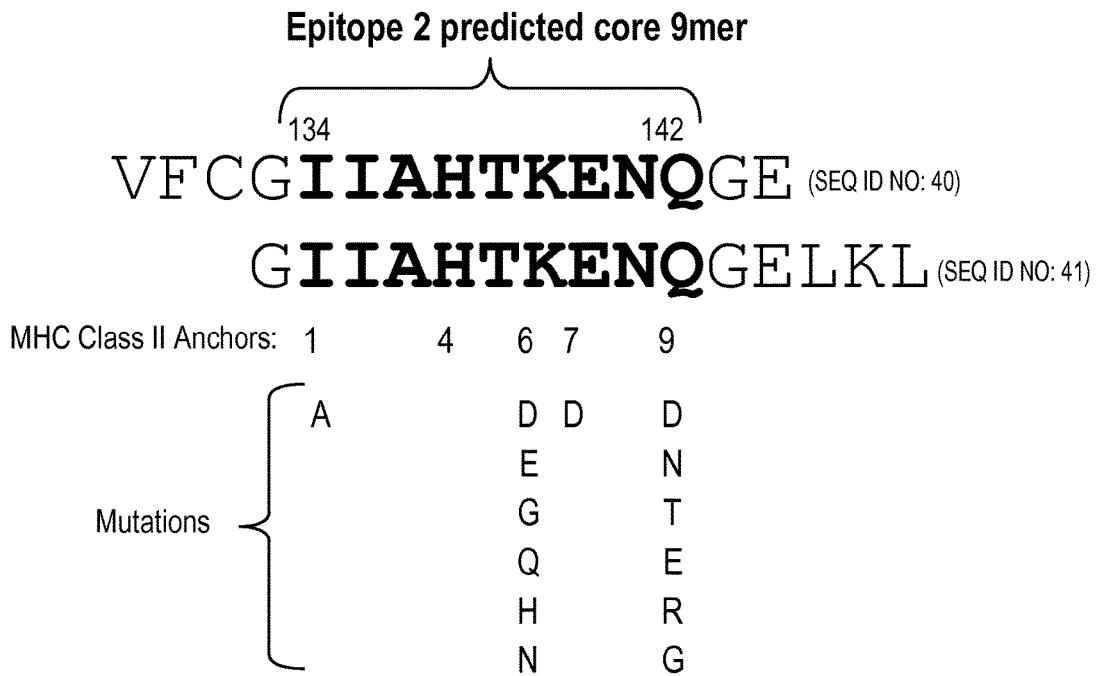

More specifically, 29 single epitope variants having a single mutation as shown in FIG. 3 were generated using the α-sarcin wild type expression plasmid pRCT02-001 as a template and applying PCR-based site directed mutagenesis. The single epitope variants were cloned into the T7 expression plasmid pET22b (Novagen, Cat. No. 69744) downstream of the NdeI site. As the null mutation (H137Q) from expression plasmid (pRCT02-002) was previously shown to be immunogenic, an alternative non-immunogenic null mutation (E96Q) was also included using PCR-based site directed mutagenesis (pRCT02-036). All constructs were confirmed by sequencing.

To assess the toxic activity of the single epitope variants, a cell-free IVTT assay was performed with a TnT® T7 Coupled Reticulocyte Lysate System (Promega, Cat. No. L4610). Briefly, pET22b plasmids containing either wild type α-sarcin (pRCT02-001), α-sarcin H137Q (pRCT02-002), α-sarcin E96Q (pRCT02-036) or the 29 single epitope variants having a single mutation as shown in FIG. 3 were tested at concentrations ranging from 200 ng to 3.125 ng per 12.5 μl reaction. The test DNA was combined with the IVTT reaction mix and incubated at 22° C. for 45 min. 250 ng of T7 Luciferase plasmid provided with the TnT® T7 Coupled Reticulocyte Lysate System (Promega, Cat. No. L4610) were added and the reactions incubated at 24° C. for a further 90 min. Luciferase activity was measured using Steady Glo® reagent (Promega, Cat. No. E2510) according to the manufacturers instructions. Luminescence was measured in a FluoStar Optima plate reader (BMG Labtech). PRCT02-001 (positive control) and pRCT02-002 (negative control) plasmids were included in each experiment. The results are summarized in Table 9.

TABLE 9

| Plasmid | Vector Backbone | Mutation | Epitope | Relative IC50 |
|---------|-----------------|----------|---------|---------------|
| pRCT02-007 | pET22b | D9A | Epitope 1 | 1.25 |
| pRCT02-008 | pET22b | D9T | Epitope 1 | 0.92 |
| pRCT02-009 | pET22b | Q10K | Epitope 1 | 0.87 |
| pRCT02-010 | pET22b | Q10R | Epitope 1 | 1.23 |
| pRCT02-011 | pET22b | Q10A | Epitope 1 | 0.53 |
| pRCT02-012 | pET22b | P13I | Epitope 1 | 0.88 |
| pRCT02-013 | pET22b | T15G | Epitope 1 | 0.62 |
| pRCT02-014 | pET22b | T15Q | Epitope 1 | 1.11 |
| pRCT02-015 | pET22b | T15H | Epitope 1 | 0.95 |
| pRCT02-016 | pET22b | N16R | Epitope 1 | 0.86 |
| pRCT02-017 | pET22b | N16K | Epitope 1 | 0.89 |
| pRCT02-018 | pET22b | N16A | Epitope 1 | 0.54 |
| pRCT02-019 | pET22b | Y18H | Epitope 1 | 0.86 |
| pRCT02-020 | pET22b | Y18K | Epitope 1 | 0.67 |
| pRCT02-021 | pET22b | Y18R | Epitope 1 | 0.82 |
| pRCT02-022 | pET22b | I134A | Epitope 2 | >10 |
| pRCT02-023 | pET22b | K139D | Epitope 2 | 1.27 |
| pRCT02-024 | pET22b | K139E | Epitope 2 | 0.88 |
| pRCT02-025 | pET22b | K139G | Epitope 2 | 1.63 |
| pRCT02-026 | pET22b | K139Q | Epitope 2 | 0.73 |
| pRCT02-027 | pET22b | K139H | Epitope 2 | 0.71 |
| pRCT02-028 | pET22b | K139N | Epitope 2 | 2.85 |
| pRCT02-029 | pET22b | E140D | Epitope 2 | 0.65 |
| pRCT02-030 | pET22b | Q142D | Epitope 2 | 1.54 |
| pRCT02-031 | pET22b | Q142N | Epitope 2 | 0.96 |
| pRCT02-032 | pET22b | Q142T | Epitope 2 | 0.66 |
| pRCT02-033 | pET22b | Q142E | Epitope 2 | 1.04 |
| pRCT02-034 | pET22b | Q142R | Epitope 2 | 0.91 |
| pRCT02-035 | pET22b | Q142G | Epitope 2 | 0.53 |

The data indicate that 28 out of the 29 single epitope mutants of α-sarcin (15/15 in epitope 1 and 13/14 in epitope 2) retained the ability to significantly inhibit the translation of the luciferase gene at a level similar to wild type α-sarcin (pRCT02-001) with the exception being I134A in epitope 2. The majority of variants inhibited luciferase gene translation at levels similar to wild type α-sarcin (subject to assay variation). Several variants unexpectedly inhibited luciferase gene translation at levels superior to wild type α-sarcin. The data for 3 single epitope variants (K139G, K139N and Q142D) suggested reduced inhibition of translation (relative IC50s>1.5). No inhibition was observed with RCT02-036, which encodes the null mutant sarcin E96Q.

Example 3

Multiple Epitope Variants of Alpha Sarcin

The following example describes the design and construction of multiple epitope variants of α-sarcin, having one mutation in Sarcin Epitope 1 and one mutation in Sarcin Epitope 2.

The double epitope variants were generated using the wild type α-sarcin expression plasmid pRCT02-001 as a template and applying PCR-based site directed mutagenesis resulting in the plasmids detailed in Table 10. The double epitope variants were cloned into the T7 expression plasmid pET22b (Novagen, Cat. No. 69744) downstream of the NdeI site. All constructs were confirmed by DNA sequencing.

TABLE 10

| Plasmid | Vector Backbone | Mutations | Epitope | Relative IC50 |
|---|---|---|---|---|
| pRCT02-049 | pET22b | Q10K K139D | Epitope 1 and 2 | 1.16 |
| pRCT02-050 | pET22b | Q10K K139E | Epitope 1 and 2 | 0.98 |
| pRCT02-051 | pET22b | Q10K Q142N | Epitope 1 and 2 | 1.09 |
| pRCT02-052 | pET22b | N16R K139D | Epitope 1 and 2 | 1.01 |
| pRCT02-053 | pET22b | N16R K139E | Epitope 1 and 2 | 1.08 |
| pRCT02-054 | pET22b | N16R Q142N | Epitope 1 and 2 | 1.11 |
| pRCT02-055 | pET22b | N16K K139D | Epitope 1 and 2 | 1.62 |
| pRCT02-056 | pET22b | N16K K139E | Epitope 1 and 2 | 1.79 |
| pRCT02-057 | pET22b | N16K Q142N | Epitope 1 and 2 | 2.63 |
| pRCT02-058 | pET22b | Y18K K139D | Epitope 1 and 2 | 1.36 |
| pRCT02-059 | pET22b | Y18K K139E | Epitope 1 and 2 | 1.49 |
| pRCT02-060 | pET22b | Y18K Q142N | Epitope 1 and 2 | 3.52 |
| pRCT02-061 | pET22b | Y18R K139D | Epitope 1 and 2 | 1.05 |
| pRCT02-062 | pET22b | Y18R K139E | Epitope 1 and 2 | 1.37 |
| pRCT02-063 | pET22b | Y18R Q142N | Epitope 1 and 2 | 1.24 |
| pRCT02-064 | pET22b | Q10K Q142T | Epitope 1 and 2 | 0.89 |
| pRCT02-065 | pET22b | N16R Q142T | Epitope 1 and 2 | 1.28 |
| pRCT02-066 | pET22b | N16K Q142T | Epitope 1 and 2 | 1.27 |
| pRCT02-067 | pET22b | Y18K Q142T | Epitope 1 and 2 | 1.98 |
| pRCT02-068 | pET22b | Y18R Q142T | Epitope 1 and 2 | 1.25 |

To assess the toxic activity of the double epitope variants, a cell-free IVTT assay was performed with a TnT® T7 Coupled Reticulocyte Lysate System (Promega, Cat. No. L4610) according to the manufacturers instructions with some modifications. Briefly, pET22b plasmids containing either wild type α sarcin (pRCT02-001), α sarcin-H137Q (pRCT02-002) or double epitope variants were tested at concentrations ranging from 200 ng to 3.125 ng per 12.5 µl reaction. The test DNA was combined with the IVTT reaction mix and incubated at 22° C. for 45 min. 250 ng of T7 Luciferase plasmid DNA provided with the TnT® T7 Coupled Reticulocyte Lysate System (Promega, Cat. No. L4610) were added and the reactions incubated at 24° C. for a further 90 min. Luciferase activity was measured using Steady Glo® reagent (Promega, Cat. No. E2510) according to the manufacturers instructions. Luminescence was measured in a FluoStar Optima plate reader (BMG Labtech). pRCT02-001 (positive control) and pRCT02-002 (negative control) plasmids were included in each experiment. Relative IC50 values were calculated by dividing the IC50 of aS-WT (pRCT02-001) by that of the double epitope variant assayed on the same plate. The results are summarized in Table 9 above. The data indicated that 18 out of the 20 double epitope variants retained the ability to inhibit the translation of the luciferase gene at a level within 2-fold of wild type α-sarcin (pRCT02-001).

Eight double epitope variants were selected as shown in Table 11 for protein production and further analysis. These were partly based on activity data (as summarized in Table 10) and on other criteria, for example exclusion of Q142N based on its association with a number of less active variants. Genes encoding the eight selected double epitope variants were cloned into the T7 expression plasmid pET22b (Novagen) downstream of a modified OMPA (outer membrane protein A) leader peptide, which has been shown to have improved processing and export compared to the original sequence (Lacadena J., et al. 1994) to create the expression vectors detailed in Table 11. In addition, a 6×His tag (SEQ ID NO:50) was genetically fused to the C-terminus of the proteins to enable detection using anti-His antibodies, as well as for use in protein purification.

TABLE 11

| IVTT Plasmid Name | Expression Plasmid Name | Mutations |
|---|---|---|
| pRCT02-049 | pRCT02-069 | Q10K K139D |
| pRCT02-050 | pRCT02-070 | Q10K K139E |
| pRCT02-052 | pRCT02-071 | N16R K139D |
| pRCT02-053 | pRCT02-072 | N16R K139E |
| pRCT02-058 | pRCT02-073 | Y18K K139D |
| pRCT02-059 | pRCT02-074 | Y18K K139E |
| pRCT02-062 | pRCT02-075 | Y18R K139E |
| pRCT02-064 | pRCT02-076 | Q10K Q142T |

Figure 4:
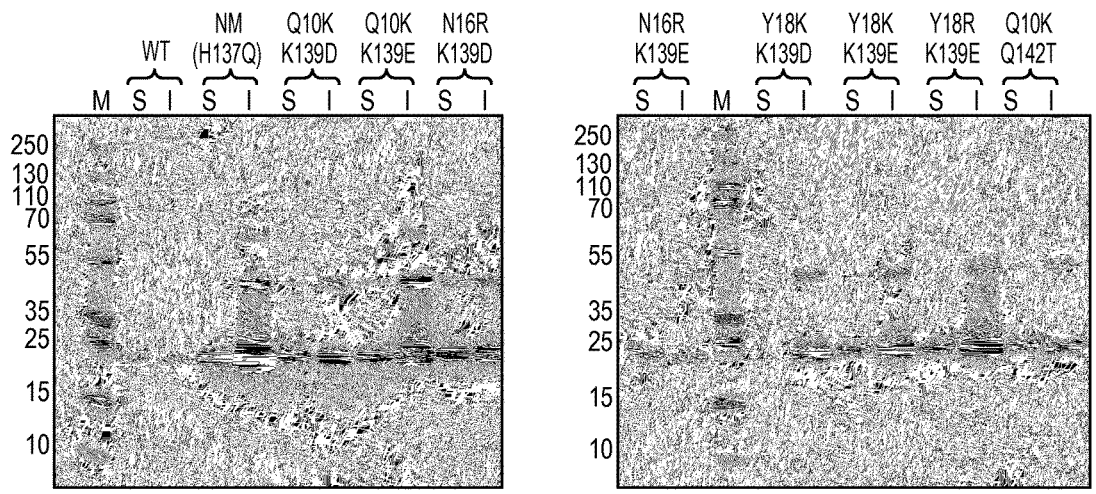
FIG. 4 shows analysis of expression of α-sarcin double epitope variants by anti-His western blot of soluble (S) and insoluble (I) fractions following B-Per extraction. Size marker is prestained protein standard Fermentas PageRuler Plus (Cat. No. SM1811).

To express the double epitope variants, an E. coli BL21 strain SHuffle™ T7 Express (NEB, Cat. No. C3029H) derivative overexpressing the chaperonins GroEL/S was used. Bacteria were transformed with expression plasmids encoding double epitope variants together with wild type α-sarcin and the null mutant (α-sarcin H137Q) and plated out. Single colonies were picked and grown in 2YT broth overnight at 37° C. The following day, the overnight culture was diluted 1:20 in 2YT broth and bacterial growth at 37° C. was monitored by OD600 measurement. Protein expression was induced at OD600 nm=1.0 by adding IPTG to give a final concentration of 1 mM and the culture was then grown at 20° C. overnight before cells were harvested by centrifugation. Cell pellets were resuspended in 10 ml B-PER reagent per 50 ml culture (Pierce, Cat. No. 78248) containing Dnase I (Roche, Cat. No. 04716728001) with protease inhibitors (Roche, Cat. No. 04693159001). The insoluble protein was removed by centrifugation according to the manufacturers protocol and soluble protein quantitated using a Bio-Rad protein assay (Cat. No. 500-0006). The protein gels were western blotted and expressed protein detected using an anti-His antibody (Sigma, Cat. No. A7058). The western blot showed that a significant proportion of the protein expressed of the double epitope variants was soluble. FIG. 4. The exception was the variant Y18K Y139D (pRCT02-058) which showed a significant insoluble fraction with only a minor fraction soluble. FIG. 4.

Figure 5:
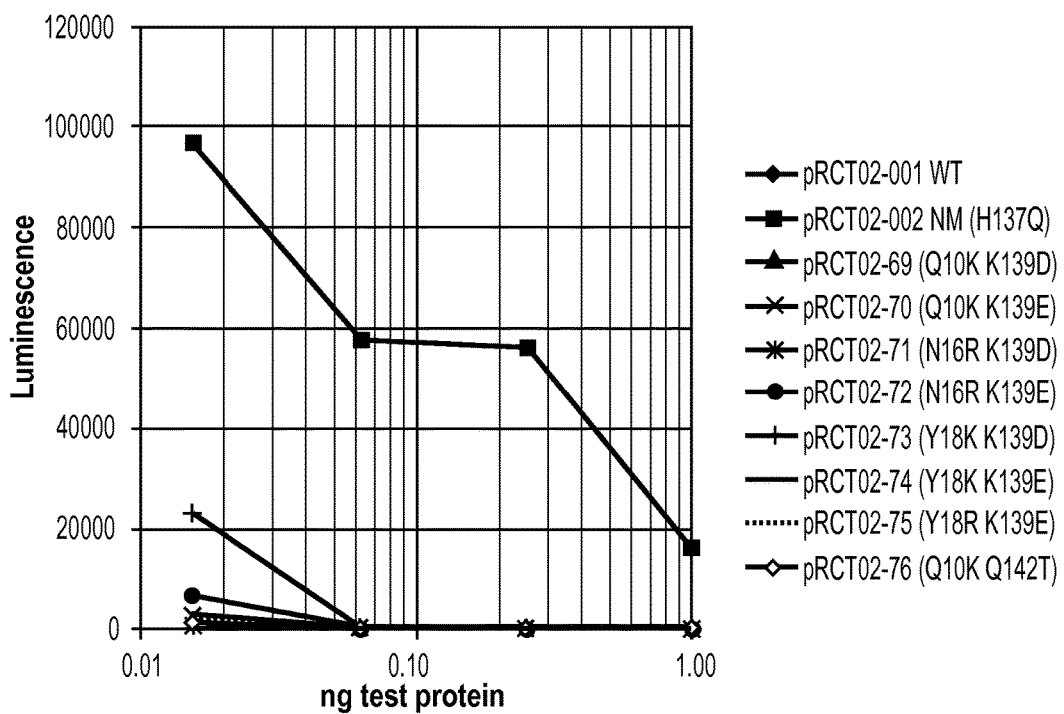
FIG. 5 shows the results of an IVTT assay using soluble extracts containing wild type α-sarcin, α-sarcin null mutant H137Q, and various α-sarcin double mutants.

To assess activity, the soluble material was tested in the IVTT assay, as discussed above. 4-fold serial dilutions starting at 1 ng of soluble protein extract in the first well were performed followed by preincubated with the IVTT reagent at 30° C. for 15 min before 250 ng of T7 Luciferase plasmid was added to each reaction. The reactions were incubated at 30° C. for 90 min and luciferase activity was measured using Steady Glo® reagent (Promega, Cat. No. E2510) as described above. Many of the double mutants showed enhanced expression levels compared to wild type α sarcin with significantly greater amounts of soluble material being produced. The soluble material in the double epitope variant crude extracts was significantly more active in the IVTT assay compared to α sarcin H137Q suggesting that the protein is correctly folded. FIG. 5. Some background activity was associated with the soluble extract from α sarcin H137Q; however this may be attributed to the fact that the α-sarcin H137Q protein was not purified and therefore contained other bacterial host proteins.

In summary, genes encoding 20 double epitope variants of α-sarcin were generated, cloned and tested in the IVTT assay. Of these, 18 variants retained activity in the IVTT assay within two-fold of wild type α sarcin. The expression and activity of 8 selected double epitope variants were further analyzed following cloning into an expression vector. Expression of soluble protein was improved for all variants, except Y18K Y139D (pRCT02-058), compared to wild type α sarcin and soluble protein from each of these variants was extracted and shown to be active in the IVTT assay.

Example 4

Triple and Quadruple Variants of Alpha Sarcin

The following example describes the design and construction of 1) triple variants of α-sarcin, having either two mutations in Sarcin Epitope 1 and one mutation in Sarcin Epitope 2 or one mutation in Sarcin Epitope 1 and two mutations in Sarcin Epitope 2; and 2) quadruple variants of α-sarcin, having two mutations in Sarcin Epitope 1 and two mutations in Sarcin Epitope 2.

Seven triple and two quadruple variants were generated using the α-sarcin-WT expression plasmid pRCT02-001 as a template and applying PCR-based site directed mutagenesis resulting in plasmids detailed in Table 12. The epitope variants were cloned into the T7 expression plasmid pET22b (Novagen, Cat. No. 69744) downstream of the NdeI site. All constructs were confirmed by DNA sequencing.

TABLE 12

| Plasmid | Vector Backbone | Mutations | Epitope | Relative IC50 |
| --- | --- | --- | --- | --- |
| pRCT02-081 | pET22b | Q10K<br>K139D Q142T | Epitope 1<br>Epitope 2 | 0.32 |
| pRCT02-082 | pET22b | Q10K<br>K139E Q142T | Epitope 1<br>Epitope 2 | 0.22 |
| pRCT02-083 | pET22b | N16R<br>K139D Q142T | Epitope 1<br>Epitope 2 | 0.27 |
| pRCT02-084 | pET22b | N16R<br>K139E Q142T | Epitope 1<br>Epitope 2 | 0.22 |
| pRCT02-085 | pET22b | Q10K N16R<br>K139D | Epitope 1<br>Epitope 2 | |
| pRCT02-086 | pET22b | Q10K N16R<br>K139E | Epitope 1<br>Epitope 2 | |
| pRCT02-087 | pET22b | Q10K N16R<br>Q142T | Epitope 1<br>Epitope 2 | |
| pRCT02-088 | pET22b | Q10K N16R<br>K139D Q142T | Epitope 1<br>Epitope 2 | |
| pRCT02-089 | pET22b | Q10K N16R<br>K139E Q142T | Epitope 1<br>Epitope 2 | |

Figure 6:
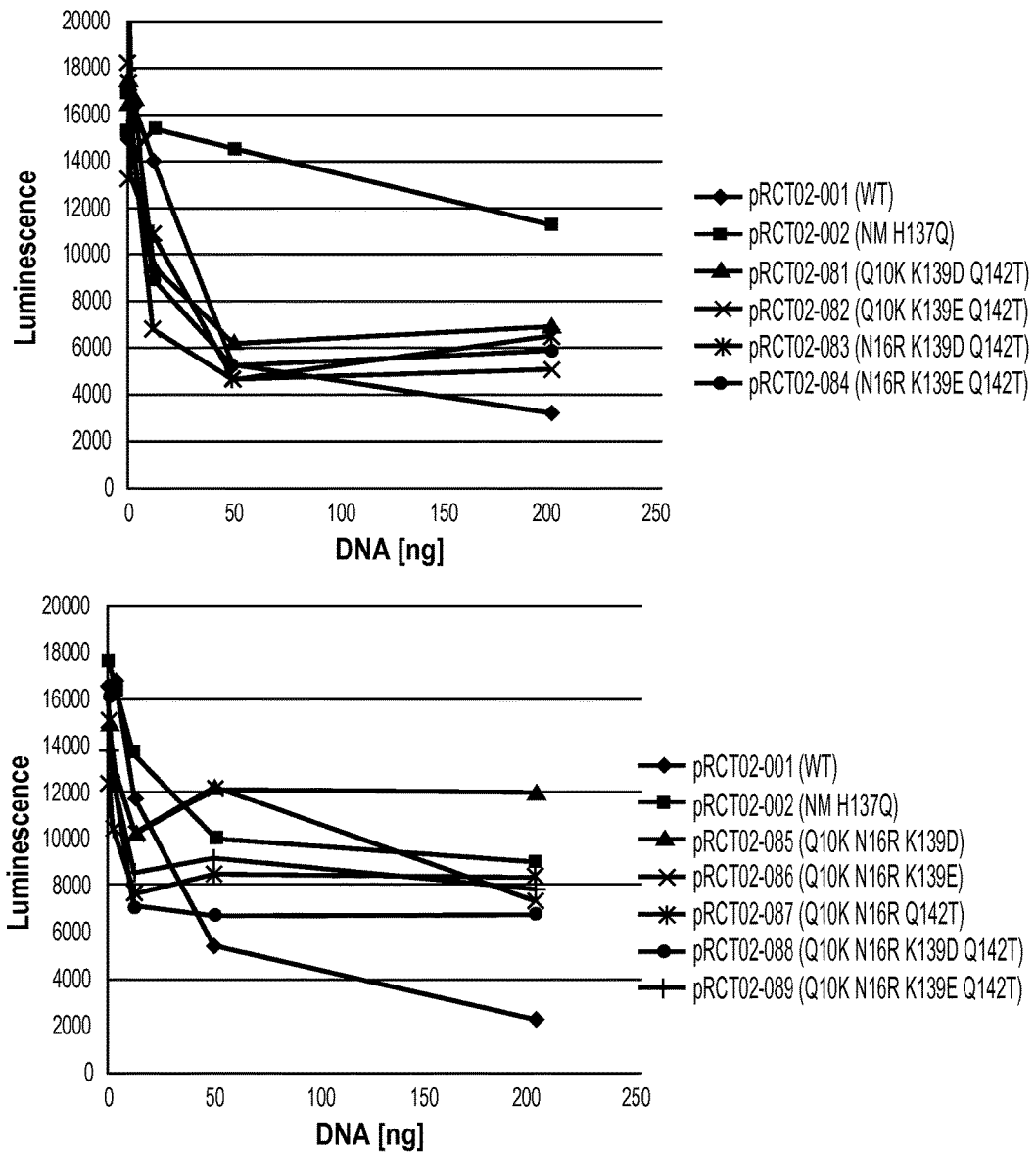
FIG. 6 shows the results of an IVTT assay using plasmids encoding wild type α-sarcin, α-sarcin null mutant (H137Q), and triple/quadruple variants of α-sarcin.

The toxic activity of the triple and quadruple variants was assessed as described in Example 3. The results are shown in FIG. 6 and summarized in Table 12 above. The data indicated that 4 out of the 9 triple and quadruple variants of α-sarcin retained the ability to inhibit the translation of the luciferase gene (pRCT02-001).

Four triple variants as shown in Table 13 were selected based on activity data (as summarized in Table 12) for protein production and further analysis. Genes encoding the four selected triple variants were cloned into the T7 expression plasmid pET22b (Novagen) downstream of a modified OMPA (outer membrane protein A) leader peptide, which has been shown to have improved processing and export compared to the original sequence (Lacadena J., et al. 1994) to create the expression vectors detailed in Table 13. In addition, a 6×His tag (SEQ ID NO:50) was genetically fused to the C-terminus of the proteins to enable detection using anti-His antibodies, as well as to assist in protein purification.

TABLE 13

| IVTT Plasmid Name | Expression Plasmid Name | Mutations |
| --- | --- | --- |
| pRCT02-081 | pRCT02-090 | Q10K K139D Q142T |
| pRCT02-082 | pRCT02-091 | Q10K K139E Q142T |
| pRCT02-083 | pRCT02-092 | N16R K139D Q142T |
| pRCT02-084 | pRCT02-093 | N16R K139E Q142T |

Figure 7A:
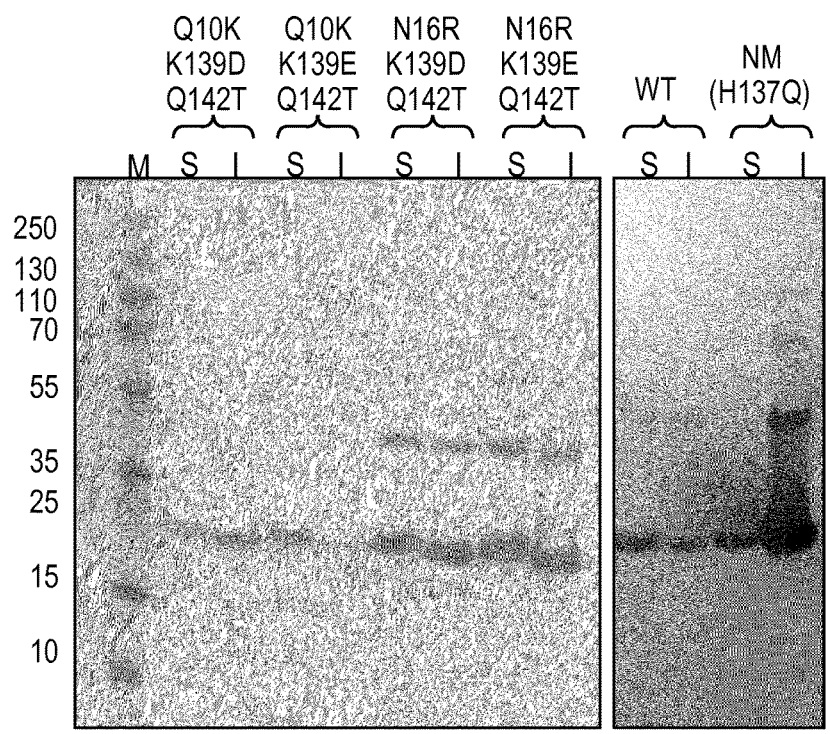
FIGS. 7A-B show analysis of protein expression of α-sarcin triple variants.

The triple variants of α-sarcin were expressed as in Example 3. The protein gels were western blotted and expressed protein detected using an anti-His antibody (Sigma, Cat. No. A7058) as shown in FIG. 7A. FIG. 7A shows that a significant proportion of the protein expressed for the triple variants was soluble. The amount of soluble material produced by all triple variants was comparable to α-sarcin-WT. Protein expression from pRCT02-092 and pRCT02-093 appeared to be greater than from pRCT02-090 and pRCT02-091.

Figure 7B:
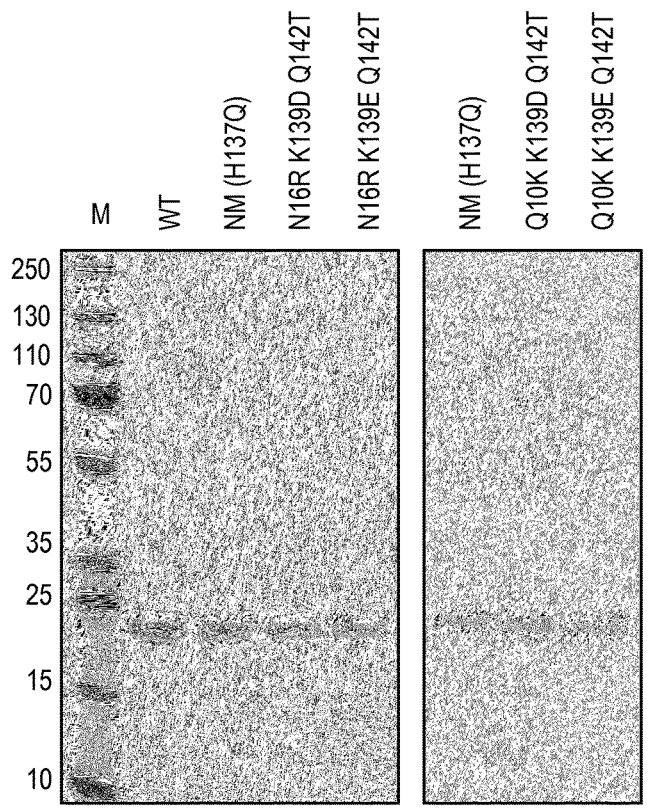
Figure 8:
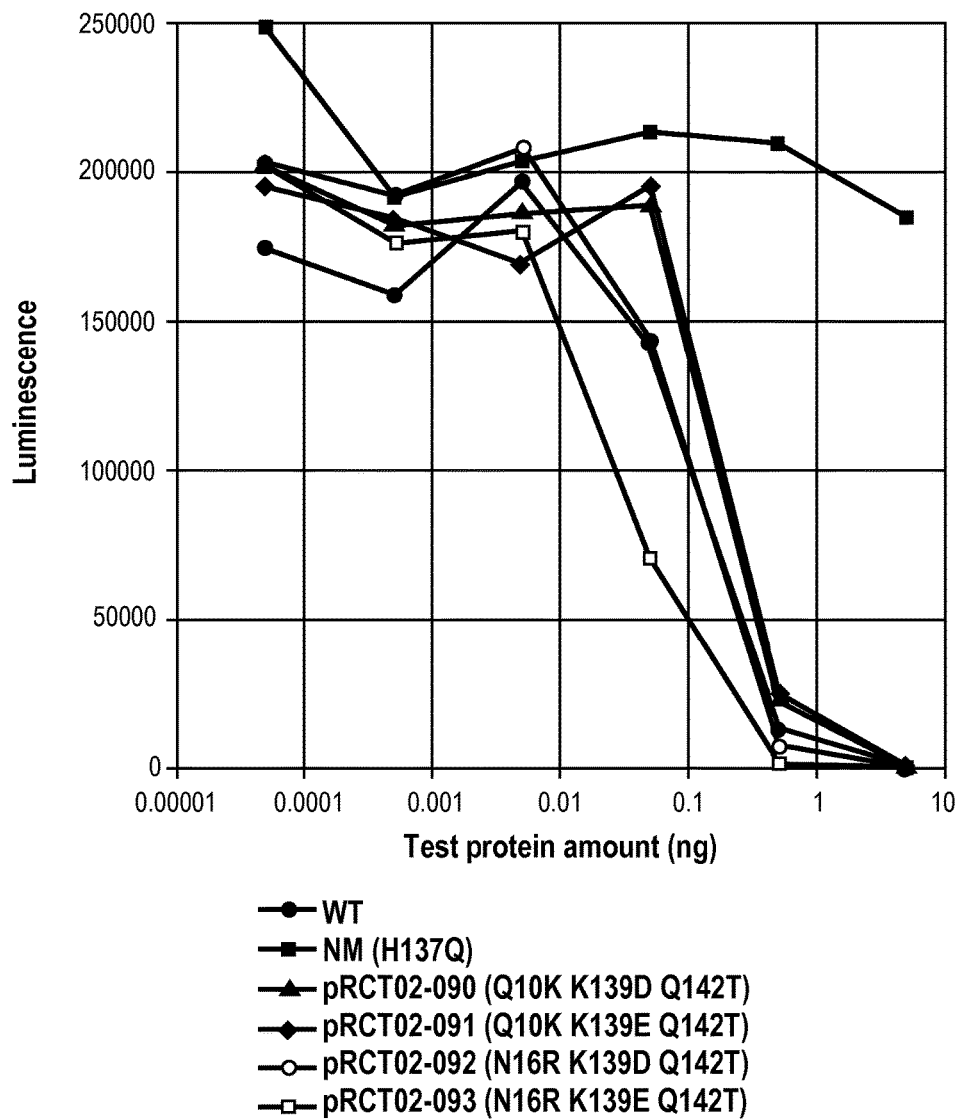
FIG. 8 shows the results of an IVTT assay using purified protein for wild type α-sarcin, α-sarcin null mutant (H137Q), and triple variants of α-sarcin.

To batch purify triple variants of α-sarcin, an E. coli BL21 strain SHuffle™ T7 Express derivative (NEB, Cat. No. C3029H) overexpressing the chaperonins GroEL/S was used. Bacteria were transformed with expression plasmids encoding triple variants together with α-sarcin-WT and the null mutant (αS-H137Q), and these were plated out. Single colonies were picked and grown in 2YT broth overnight at 37° C. The following day, the overnight cultures were diluted 1:20 in 500 ml 2YT broth and bacterial growth at 37° C. was monitored by OD600 measurement. Protein expression was induced at OD600 nm=1.0 by adding IPTG to give a final concentration of 1 mM, and the cultures were then grown at 20° C. overnight before cells were harvested by centrifugation and frozen overnight at −80° C. Cell pellets were resuspended in B-PER (Pierce, Cat. No. 78248) containing Dnase I (Roche, Cat. No. 04716728001) with protease inhibitors (Roche, Cat. No. 04693159001). The insoluble protein was removed by centrifugation according to the manufacturers protocol. Soluble protein was diluted 2-fold in 40 mM Tris pH 7.5, 300 mM NaCl, 80 mM imidazole and cleared by centrifugation before addition of 1 ml of Ni-NTA-agarose (Qiagen, Cat. No. 1018244) pre-equilibrated with 20 mM Tris pH 7.5, 300 mM NaCl and 40 mM imidazole (binding buffer) and incubation with rotation overnight at 4° C. Unbound protein was removed by centrifugation followed by a 10 CV wash with binding buffer. A step elution was then performed starting with a 10 CV wash with 20 mM Tris pH 7.5, 300 mM NaCl, 100 mM imidazole (wash buffer) followed by elution with 20 mM Tris pH 7.5, 300 mM NaCl, 400 mM imidazole (elution buffer). 1 ml fractions from the elution were collected and run on protein gels. Fractions containing the protein of interest were pooled, buffer exchanged into PBS pH 7.4 and soluble protein quantitated using a Bio-Rad protein assay (Cat. No. 500-0006). All proteins were then analysed by reducing SDS-PAGE. 1 μg of each sample was loaded on a NuPage 4-12% Bis-Tris gel (Invitrogen Cat No. NP0322BOX) and run at 200 V for 35 min. FIG. 7B To assess activity of the purified triple variants, an IVTT assay was performed as described above with some modifications. In brief, 5 ng of purified protein, and 10-fold dilutions thereof, were preincubated with ribosomes at 30° C. for 15 min before 250 ng of T7 Luciferase plasmid was added to each reaction. The reactions were incubated at 30° C. for 90 min and Luciferase activity was measured using Steady Glo® reagent as described above. As shown in FIG. 8, all variants retained activity comparable to that of the wild type α-sarcin.

The cytotoxic activity of purified proteins was measured in a cellular cytotoxicity assay using the T lymphoblastoid cell line Jurkat as the target Briefly, Jurkat cells in the log phase of growth were diluted to $1.25 \times 10^5$ cells/ml and 50 µl dispensed into each well of a 96-well white-walled tissue culture plate (Corning Cat. No. 3610). A dilution plate was prepared containing a seven-point 5-fold dilution series of each test sample and 50 µl of each dilution series was transferred directly onto the Jurkat cells. The Jurkat cell plate was then returned to the incubator for a further 72 hours. After incubation, the plate was equilibrated at room temperature for 10 min. The plate was developed by the addition of 100 µl of Cell TiterGlo® reagent (Promega, Cat. No. G7571) to each well and 1 second luminescence readings were taken using a FluoStar Optima plate reader (BMG Labtech).

Figure 9:
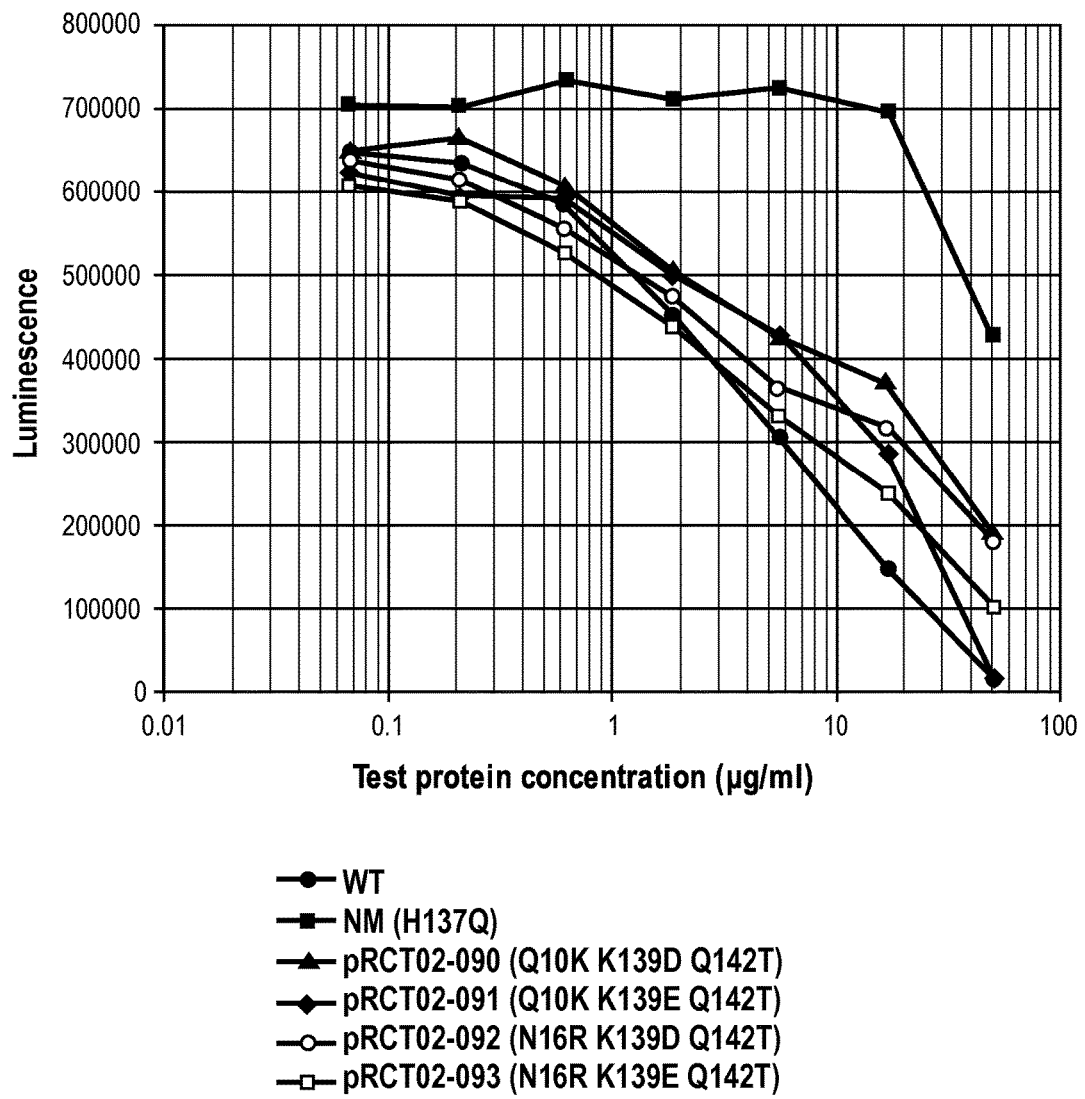
FIG. 9 shows the results of a cellular (Jurkat) cytotoxicity assay using wild type α-sarcin, α-sarcin null mutant (H137Q), and triple variants of α-sarcin.

Using purified triple variants, efficient killing of Jurkat cells was observed with all variants (FIG. 9) indicating that the proteins both translocate across the cell membrane and inhibit protein synthesis similarly to α-sarcin-WT.

In summary, 7 triple variants and 2 quadruple variants were generated and tested in the IVTT assay. These data showed that 4 of the triple variants retained the ability to inhibit the translation of the luciferase reporter gene. These variants each contained one mutation in epitope 1 and two mutations in epitope 2. Variants containing two mutations in epitope 1 and one mutation in epitope 2 as well as quadruple variants, which contained two mutations in each epitope, were all shown to have impaired activity in the IVTT assay. The four triple variants that retained activity were further analysed to assess expression and activity. Significant levels of protein from these triple variants were soluble and purified protein was shown to be active in the IVTT assay as well as a cellular cytotoxicity assay.

Example 5

Immunogenicity Testing of Epitope Variants of A-Sarcin

The following example describes immunogenicity testing of optimized epitope variants using EpiScreen™ whole protein time course T cell assays.

For an assessment of the immunogenicity, the lead and backup optimized α-sarcin toxin epitope variants identified (see above) will be expressed (as null mutants), purified and compared against purified wild-type (null mutant) α-sarcin toxin in EpiScreen™ whole protein time course T cell assays in order to confirm reduced risk of immunogenicity.

Bulk cultures of CD8+ T cell-depleted PBMC from selected healthy donors will be established in the presence of the wild-type and optimized variant α-sarcin toxins. Aliquots of T blasts will be removed from the bulk cultures on days 5 to 8 with an assessment of T cell activation being made by proliferation (3H-thymidine uptake) and IL-2 cytokine secretion (ELISpot assays).

Buffy coats from 20 HLA-typed healthy donors will be used to isolate PBMC that contain physiological levels of APC and CD4+ T cells. CD8+ T cells will be depleted to exclude the detection of MHC class I restricted T cell responses; Each donor will be tested against reproducibility control antigens including keyhole limpet haemocyanin (a potent neoantigen) or tetanus toxoid (recall antigen); α-sarcin toxin-specific T cell activation will then be determined by proliferation (3H-thymidine uptake) and IL-2 secretion (ELISpot); Data will be analyzed using previously validated assay parameters whereby responses of a stimulation index (SI) of >2.0 are scored as positive, supported by additional information including statistical and frequency analysis; Data for the optimized α-sarcin variants will be compared to wild-type α-sarcin toxin. This will provide for an assessment of the relative risk of immunogenicity for the optimized α-sarcin variants compared to wild-type; Immunogenicity data for the optimized α-sarcin variants will also be compared to benchmark EpiScreen™ data for a range of clinical-stage antibodies and proteins with known immunogenicity. This will provide for an assessment of the risk of clinical immunogenicity for the lead and back-up optimized α-sarcin variants. An assessment will be made of any association between donor MHC class II allotype and T cell responses to the lead and back-up optimized α-sarcin variants.

The disclosures of the following U.S. patents are incorporated in their entirety by reference herein: U.S. Pat. Nos. 7,750,136; 8,252,897; U.S. Patent Application No. 2007/0178082; U.S. Patent Application No. 2007/0135620.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the invention.

Additional Disclosures:

The Below Disclosures are not Claims.

Additional Embodiments—Modified Real Sarcin 1 Epitope

1. A modified α-sarcin T cell epitope, wherein the modified T cell epitope comprises one or more amino acid substitutions of a wild type T cell epitope having the amino acid sequence of XKNPKTNKY (SEQ ID NO:44), wherein X is Q or DQ and wherein the modified T cell epitope has reduced binding to human MHC class II molecules as compared to the wild type T cell epitope.

2. The modified α-sarcin T cell epitope of claim 1, wherein the modified T cell epitope is modified at one or more of the P1, P4, P6, P7, or P9 MHC class II anchor residues of a wild type T cell epitope having the amino acid sequence of QKNPKTNKY (SEQ ID NO:5) or at one or more of the P-1, P1, P4, P6, P7, or P9 MHC class II anchor residues of a wild type T cell epitope having the amino acid sequence of DQKNPKTNKY (SEQ ID NO:6).

3. The modified α-sarcin T cell epitope of claim 2, wherein the modified T cell epitope has the amino acid sequence of $X_1X_2NX_3KX_4X_5KX_6$, wherein $X_1$ is Q, K, R, or A; $X_2$ is K or L; $X_3$ is P or I; $X_4$ is T, G, Q, or H; $X_5$ is N, R, K or A; and $X_6$ is Y, H, K, R, or W (SEQ ID NO:8);

or wherein the modified T cell epitope has the amino acid sequence of $X_1X_2X_3NX_4KX_5X_6KX_7$, wherein $X_1$ is D, A, or T; $X_2$ is Q, K, R, or A; $X_3$ is K or L; $X_4$ is P or I; $X_5$ is T, G, Q, or H; $X_6$ is N, R, K or A; and $X_7$ is Y, H, K, R, or W (SEQ ID NO:9).

4. The modified α-sarcin T cell epitope of claim 2, wherein the modified T cell epitope is modified at the P1 (Q) and P7 (N) or P9 (Y) anchor residues of SEQ ID NO:5.

5. The modified α-sarcin T cell epitope of claim 2, wherein the modified T cell epitope is modified at the P7 (N) and P1 (Q) or P9 (Y) anchor residues of SEQ ID NO:5.

6. The modified α-sarcin T cell epitope of claim 2, wherein the modified T cell epitope is modified at the P9 (Y) and P7 (N) or P1 (Q) anchor residues of SEQ ID NO:5.

Additional Embodiments—Modified Real Sarcin 2 Epitope

1. A modified α-sarcin T cell epitope, wherein the modified T cell epitope comprises one or more amino acid substitutions of a wild type T cell epitope having the amino acid sequence of IIAHTKENQ (SEQ ID NO:4), and wherein the modified T cell epitope elicits a reduced T cell response as compared to the wild type T cell epitope.

2. The modified α-sarcin T cell epitope, wherein the modified T cell epitope is modified at one or more of the P1, P6, P7, or P9 MHC class II anchor residues of a wild type T cell epitope having the amino acid sequence of IIAHTKENQ (SEQ ID NO:4)

3. The modified α-sarcin T cell epitope of claim 2, wherein the modified T cell epitope has the amino acid sequence of $X_1X_2AHX_3X_4X_5NX_6$, wherein $X_1$ is I or A; $X_2$ is I or V; $X_3$ is T or Q; $X_4$ is K, D, E, G, Q, H, or N; $X_5$ is E or D; and $X_6$ is Q, D, N, T, E, R, or G (SEQ ID NO:11).

4. The modified α-sarcin T cell epitope of claim 2, wherein the modified T cell epitope is modified at the P6 (K) and P9 (Q) anchor residues of SEQ ID NO:4.

Additional Embodiments—Modified Sarcin Molecule

1. A modified sarcin molecule or fragment thereof comprising an amino acid sequence that is at least 75% identical to SEQ ID NO: 1 and comprising at least one modified T cell epitope core comprising at least one amino acid modification in a sequence selected from XKNPKTNKY (SEQ ID NO:44), wherein X is Q or DQ, and IIAHTKENQ (SEQ ID NO:4), wherein said modified sarcin molecule or fragment thereof inhibits protein synthesis and elicits a reduced T cell response as compared to wild type α-sarcin (SEQ ID NO:1).

2. The modified sarcin molecule of embodiment 1, wherein the modified sarcin molecule comprises at least one first mutation at one or more of D9, Q10, P13, T15, N16, or Y18 of wild type α-sarcin (SEQ ID NO:1).

3. The modified sarcin molecule of embodiment 1, wherein the modified sarcin molecule comprises at least one first mutation at one or more of I134, K139, E140, or Q142 of wild type α-sarcin (SEQ ID NO:1).

4. The modified sarcin molecule of embodiment 1, wherein the modified sarcin molecule comprises at least one first mutation at one or more of D9, Q10, P13, T15, N16, or Y18 of wild type α-sarcin (SEQ ID NO:1) and at least one second mutation at one or more of I134, K139, E140, or Q142 of wild type α-sarcin (SEQ ID NO:1).

5. A composition comprising the modified sarcin molecule of embodiment 1 and a pharmaceutically acceptable excipient or carrier.

6. The modified sarcin molecule of embodiment 1, further comprising at least one cell binding ligand.

7. The modified sarcin molecule of embodiment 6, wherein the cell-binding ligand is an antibody or antigen-binding fragment thereof, a cytokine, a polypeptide, a hormone, a growth factor, or insulin.

8. The modified sarcin molecule of embodiment 7, wherein the cytokine is IL-2 or IL-5.

9. The modified sarcin molecule of embodiment 7, wherein the antibody is monoclonal, polyclonal, humanized, genetically engineered or grafted.

10. The modified sarcin molecule of embodiment 7 wherein the antigen-binding fragment is a Fab, a Fab2, a F(ab')2, a ScFv, a (ScFv)2, a single chain binding polypeptide, a VH, or a VL.

11. A composition comprising the modified sarcin molecule of embodiment 6 and a pharmaceutically acceptable excipient or carrier.

12. A modified sarcin protein that elicits a reduced T cell response as compared to wild type alpha sarcin (SEQ ID NO: 1), wherein the amino acid sequence of the modified sarcin protein comprises:

AVTWTCLNX$_1$X$_2$ KNX$_3$KX$_4$X$_5$KX$_6$ET KRLLYNQNKA ESNSHHAPLS

DGKTGSSYPH WFTNGYDGDG KLPKGRTPIK FGKSDCDRPP

KHSKDGNGKT DHYLLEFPTF PDGHDYKFDS KKPKENPGPA

RVIYTYPNKV FCGX$_7$IAHTX$_8$X$_9$ NX$_{10}$GELKLCSH, wherein $X_1$ through $X_{10}$ can be any amino acid (SEQ ID NO:12, provided that the amino acid sequence of the modified sarcin protein is not identical to the wild type sarcin protein (SEQ ID NO:1).

13. The modified sarcin protein of embodiment 12, wherein $X_1$ is D, A, or T; $X_2$ is Q, K, R, or A; $X_3$ is P or I; $X_4$ is T, G, Q, or H; $X_5$ is N, R, K or A; $X_6$ is Y, H, K, or R; $X_7$ is I or A; $X_8$ is K, D, E, G, Q, H, or N; $X_9$ is E or D; and $X_{10}$ is Q, D, N, T, E, R, or G (SEQ ID NO: 13).

14. A modified sarcin protein or fragment thereof, comprising at least one modified T-cell epitope, wherein the at least one modified T-cell epitope comprises at least one amino acid modification as compared to the polypeptide of SEQ ID NO:1, and wherein the modified sarcin protein or fragment thereof elicits a reduced T cell response as compared to wild type alpha sarcin (SEQ ID NO: 1).

Additional Embodiments—Nucleic Acid Encoding Modified Sarcin

1. A nucleic acid encoding a modified sarcin protein, wherein the modified sarcin protein has a reduced propensity to elicit an immune response, as compared to the wild type sarcin protein (SEQ ID NO: 1), wherein the amino acid sequence of the modified sarcin protein comprises:

AVTWTCLNX$_1$X$_2$ KNX$_3$KX$_4$X$_5$KX$_6$ET KRLLYNQNKA ESNSHHAPLS

DGKTGSSYPH WFTNGYDGDG KLPKGRTPIK FGKSDCDRPP

KHSKDGNGKT DHYLLEFPTF PDGHDYKFDS KKPKENPGPA

RVIYTYPNKV FCGX$_7$IAHTX$_8$X$_9$ NX$_{10}$GELKLCSH, wherein $X_1$ through $X_{10}$ can be any amino acid (SEQ ID NO:12), provided that the amino acid sequence of the modified sarcin protein is not identical to the wild type sarcin protein (SEQ ID NO:1).

1.1. The nucleic acid encoding a modified sarcin protein according to embodiment 1, wherein the modified sarcin protein inhibits protein synthesis on ribosomes.

2. The nucleic acid encoding a modified sarcin protein according to embodiment 1, wherein $X_1$ is D, A, or T; $X_2$ is Q, K, R, or A; $X_3$ is P or I; $X_4$ is T, G, Q, or H; $X_5$ is N, R, K or A; $X_6$ is Y, H, K, or R; $X_7$ is I or A; $X_8$ is K, D, E, G, Q, H, or N; $X_9$ is E or D; and $X_{10}$ is Q, D, N, T, E, R, or G (SEQ ID NO:13).

3. The nucleic acid encoding a modified sarcin protein according to embodiment 1, wherein said immune response is T cell activity.

4. A nucleic acid encoding a cytotoxin comprising: (a) a nucleic acid encoding a targeting moiety attached to; (b) a nucleic acid encoding the modified sarcin protein of embodiment 1.

5. A nucleic acid encoding a cytotoxin comprising: (a) a nucleic acid encoding a ligand that binds to a target attached to; (b) a nucleic acid encoding the modified sarcin protein of embodiment 1.

6. The nucleic acid encoding a cytotoxin of embodiment 5, wherein the ligand is an antibody or antibody fragment that binds to the target.

7. The nucleic acid encoding a cytotoxin of embodiment 6, wherein the antibody or antibody fragment binds to Ep-CAM on the surface of the cancer cell.

8. The nucleic acid encoding a cytotoxin of embodiment 7, wherein the antibody or antibody fragment that binds to Ep-CAM is a humanized antibody or antibody fragment that binds to the extracellular domain of human Ep-CAM and comprises complementarity determining region sequences derived from a MOC-31 antibody.

9. The nucleic acid encoding a cytotoxin of embodiment 7, wherein the variable region of the cancer-binding ligand attached to the modified sarcin protein is 4D5MOCB.

10. The nucleic acid encoding a cytotoxin of embodiment 6, wherein the antibody or antibody fragment binds to a tumor-associated antigen on the surface of the cancer cell.

Additional Embodiments—Fusion Proteins

1. A ribotoxin fusion protein comprising:
   (a) a modified sarcin molecule having reduced immunogenicity in humans as compared to wild type α-sarcin; and
   (b) a targeting molecule linked to the modified sarcin molecule, the targeting molecule is effective for binding a target.

2. The ribotoxin fusion protein of embodiment 1, wherein the targeting molecule is linked to the N-terminus of the modified sarcin molecule.

3. The ribotoxin fusion protein of embodiment 1, wherein the targeting molecule is linked to the C-terminus of the modified sarcin molecule.

4. The ribotoxin fusion protein of embodiment 1, wherein the targeting molecule is incorporated within the modified sarcin molecule.

5. The ribotoxin fusion protein of embodiment 1, wherein the targeting molecule and the modified sarcin molecule are linked via a linker.

5.1. The ribotoxin fusion protein of embodiment 5, wherein the linker comprises an amino acid or a peptide.

6. The ribotoxin fusion protein of embodiment 5, wherein the linker is between 1 and 20 amino acids in length.

7. The ribotoxin fusion protein of embodiment 5, wherein the linker is between 3 and 20 amino acids in length.

8. The ribotoxin fusion protein of embodiment 5, wherein the linker is between 4 and 30 amino acids in length.

9. The ribotoxin fusion protein of embodiment 5, wherein the linker comprises a discrete polyethylene glycol (dPEG).

9.1. The ribotoxin fusion protein of embodiment 9, wherein the dPEG is linked to the modified sarcin molecule at either one of a serine, tyrosine, cysteine, or lysine of the modified sarcin molecule or a glycosylation site of the modified sarcin molecule.

9.2. The ribotoxin fusion protein of embodiment 9, wherein the dPEG is linked to the targeting molecule at either one of a serine, tyrosine, cysteine, or lysine of the targeting molecule or a glycosylation site of the targeting molecule.

9.3. The ribotoxin fusion protein of embodiment 9, wherein the dPEG is between about 200 to 10,000 daltons.

9.4. The ribotoxin fusion protein of embodiment 1, wherein a branched dPEG molecule is linked to the targeting molecule.

9.5. The ribotoxin fusion protein of embodiment 9.3, wherein between 1 and 12 sarcin molecules are attached to one or more branches of the branched dPEG molecule.

10. The ribotoxin fusion protein of embodiment 1, wherein the targeting molecule comprises a peptide.

11. The ribotoxin fusion protein of embodiment 1, wherein the targeting molecule comprises an antibody, an antibody fragment, a single chain variable fragment (scFv), a nanobody, an abdurin, a CH2 domain molecule, a CH2 domain fragment, a CH3 domain molecule, a CH3 domain fragment, a protein scaffold, a hormone, a receptor-binding peptide, or a combination thereof.

11.01. The ribotoxin fusion protein of embodiment 11, wherein the targeting molecule targets Her2 receptor, PMSA, nucleolin, or a death receptor.

11.02. The ribotoxin fusion protein of embodiment 11.01, wherein the death receptor is a Fas receptor or tumor necrosis factor receptor 11.1. The ribotoxin fusion protein of embodiment 1, wherein the targeting molecule comprises a binding moiety, the binding moiety comprises a VH domain, a VL domain, a camelid VHH domain, a tenth type three domain of fibronectin, a designed ankyrin repeat protein, a centyrin scaffold, a peptide ligand, a protein ligand, a receptor, hormone, an enzyme, a cytokine, a small molecule, a fragment thereof, or a combination thereof.

12. The ribotoxin fusion protein of embodiment 1, wherein the targeting molecule comprises an antigen binding region.

13. The ribotoxin fusion protein of embodiment 1, wherein the targeting molecule is a CH2 domain molecule having a molecular weight less than about 20 kDa.

14. The ribotoxin fusion protein of embodiment 1, wherein the targeting molecule comprises at least one functional FcRn binding site.

15. The ribotoxin fusion protein of embodiment 1, wherein the fusion protein is a monospecific molecule.

16. The ribotoxin fusion protein of embodiment 1, wherein the fusion protein is a bispecific molecule.

17. The ribotoxin fusion protein of embodiment 1, wherein the fusion protein is a trispecific molecule.

18. The ribotoxin fusion protein of embodiment 1, wherein the targeting molecule comprises at least a first paratope specific for a first epitope.

19. The ribotoxin fusion protein of embodiment 1, wherein the targeting molecule comprises at least two first paratopes each specific for a first epitope.

20. The ribotoxin fusion protein of embodiment 1, wherein the targeting molecule comprises a first paratope specific for a first epitope and a second paratope specific for a second epitope.

21. The ribotoxin fusion protein of embodiment 1, further comprising a second targeting molecule linked to either the targeting molecule or the modified sarcin molecule.

21A. The ribotoxin fusion protein of embodiment 1, further comprising at least one additional targeting molecule.

22. The ribotoxin fusion protein of embodiment 21, wherein the second targeting molecule is linked to the N-terminus of the modified sarcin molecule and the targeting molecule is linked to the C-terminus of the modified sarcin molecule.

23. The ribotoxin fusion protein of embodiment 21, wherein the second targeting molecule is linked to the C-terminus of the modified sarcin molecule and the targeting molecule is linked to the N-terminus of the modified sarcin molecule.

24. The ribotoxin fusion protein of embodiment 21, wherein the second targeting molecule comprises a first paratope specific for the first epitope.

25. The ribotoxin fusion protein of embodiment 21, wherein the second targeting molecule comprises a second paratope specific for a second epitope.

26. The ribotoxin fusion protein of embodiment 1, wherein the targeting molecule comprises a third paratope specific for the first epitope or a fourth paratope specific for a third epitope.

27. The ribotoxin fusion protein of embodiment 1 further comprising a second modified sarcin molecule.

27A. The ribotoxin fusion protein of embodiment 1 further comprising at least one additional modified sarcin molecule.

28. The ribotoxin fusion protein of embodiment 27, wherein the second modified sarcin molecule is linked to the modified sarcin molecule.

29. The ribotoxin fusion protein of embodiment 27, wherein the second modified sarcin molecule is linked to the targeting molecule.

29.1 The ribotoxin fusion protein of embodiment 1, wherein the ribotoxin fusion protein comprises a cleavable linker linking the modified sarcin molecule to the targeting molecule.

29.2. The ribotoxin fusion protein of embodiment 29.1, wherein the cleavable linker can be cleaved in the cytosol.

29.3. The ribotoxin fusion protein of embodiment 29.1, wherein the cleavable linker can be cleaved in the endosome.

29.4. The ribotoxin fusion protein of embodiment 29.1, wherein the cleavable linker is not cleaved in serum.

30. The ribotoxin fusion protein of embodiment 27, wherein the second modified sarcin molecule is linked to the modified sarcin molecule or the targeting molecule via a linker.

31. The ribotoxin fusion protein of embodiment 30, wherein the linker comprises a discrete polyethylene glycol (dPEG).

32. The ribotoxin fusion protein of embodiment 31, wherein the dPEG is linked to the modified sarcin molecule at either one of a serine, tyrosine, cysteine, or lysine of the modified sarcin molecule or a glycosylation site of the modified sarcin molecule.

33. The ribotoxin fusion protein of embodiment 31, wherein the dPEG is linked to the targeting molecule at either one of a serine, tyrosine, cysteine, or lysine of the targeting molecule or a glycosylation site of the targeting molecule.

34. The ribotoxin fusion protein of embodiment 31, wherein the dPEG is between about 200 to 10,000 daltons.

35. The ribotoxin fusion protein of embodiment 1, further comprising a pharmaceutical carrier.

36. The ribotoxin fusion protein of embodiment 1, further comprising an imaging reagent, an isotope, a drug, an immunoconjugate, or a combination thereof.

37. The ribotoxin fusion protein of embodiment 36, wherein the imaging reagent, isotope, drug, or immunoconjugate is linked to the modified sarcin molecule.

38. The ribotoxin fusion protein of embodiment 36, wherein the imaging reagent, isotope, drug, or an immunoconjugate is linked to the targeting molecule.

39. The ribotoxin fusion protein of embodiment 1, wherein the target comprises a receptor.

40. The ribotoxin fusion protein of embodiment 1, wherein the target comprises a cell, a tumor cell, an immune cell, a protein, a peptide, a molecule, a bacterium, a virus, a protist, a fungus, or a combination thereof.

41. The ribotoxin fusion protein of embodiment 1, further comprising a second targeting molecule.

42. The ribotoxin fusion protein of embodiment 41, further comprising a third targeting molecule.

43. The ribotoxin fusion protein of embodiment 1, further comprising a fourth targeting molecule.

44A. The ribotoxin fusion protein of embodiment 1, wherein the fusion protein has increased cell permeability as compared to wild type α-sarcin.

44B. The ribotoxin fusion protein of embodiment 1, wherein the fusion protein has increased cell permeability as compared to the targeting molecule alone.

44C. The ribotoxin fusion protein of embodiment 1, wherein the fusion protein has increased cell permeability as compared to the modified sarcin molecule alone.

44D. The ribotoxin fusion protein of embodiment 1, wherein the fusion protein is modified to increase cell permeability as compared to wild type α-sarcin.

44E. The ribotoxin fusion protein of embodiment 1, wherein the fusion protein is modified to increase cell permeability as compared to the targeting molecule alone.

44F. The ribotoxin fusion protein of embodiment 1, wherein the fusion protein is modified to increase cell permeability as compared to the modified sarcin molecule alone.

45A. The ribotoxin fusion protein of embodiment 1, wherein the fusion protein has increased cell retention as compared to wild type α-sarcin.

45B. The ribotoxin fusion protein of embodiment 1, wherein the fusion protein has increased cell retention as compared to the targeting molecule alone.

45C. The ribotoxin fusion protein of embodiment 1, wherein the fusion protein has increased cell retention as compared to the modified sarcin molecule alone.

45D. The ribotoxin fusion protein of embodiment 1, wherein the fusion protein is modified to increase cell retention as compared to wild type α-sarcin.

45E. The ribotoxin fusion protein of embodiment 1, wherein the fusion protein is modified to increase cell retention as compared to the targeting molecule alone.

45F. The ribotoxin fusion protein of embodiment 1, wherein the fusion protein is modified to increase cell retention as compared to the modified sarcin molecule alone.

46. The modified sarcin molecule of embodiment 1 expressed in an expression system.

47. The modified sarcin molecule of embodiment 46, wherein the expression system is an *E. coli* expression system or a *Pichia pastoris* expression system.

What is claimed:

1. An isolated nucleic acid encoding a modified sarcin polypeptide or a fusion protein comprising the modified sarcin polypeptide conjugated or fused to a heterologous targeting molecule, wherein the modified sarcin polypeptide comprises at least one mutation as compared to a wild type a-sarcin polypeptide having the amino acid sequence of SEQ ID NO: 1, wherein the at least one mutation is at one or more of amino acids D9, Q10, P13, T15, N16, or Y18 of the wild type a-sarcin polypeptide and is within a first T cell epitope of the wild type a-sarcin polypeptide and/or is at one or more of amino acids 1134, K139, E140, or Q142 of the wild type a-sarcin polypeptide and is within a second T cell epitope of the wild type a-sarcin polypeptide, wherein the first T cell epitope consists of the amino acid sequence of SEQ ID NO:6, and the second T cell epitope consists of the amino acid sequence of SEQ ID NO:4, and wherein the modified sarcin polypeptide inhibits protein synthesis and elicits a reduced T cell response as compared to the wild type a-sarcin polypeptide, wherein the inhibition of protein synthesis is measured using an in vitro transcription and translation assay (IVTT).

2. An expression vector comprising the nucleic acid of claim 1.

3. A host cell transformed with an expression vector of claim 2.

4. The isolated nucleic acid of claim 1, encoding the modified sarcin polypeptide or the fusion protein comprising the modified sarcin polypeptide conjugated or fused to the heterologous targeting molecule, wherein the at least one mutation is within the first T cell epitope and is at one or more of amino acids D9, Q10, P13, T15, N16, or Y18 of the wild type a-sarcin.

5. The isolated nucleic acid of claim 1, encoding the modified sarcin polypeptide or the fusion protein comprising the modified sarcin polypeptide conjugated or fused to the heterologous targeting molecule, wherein the at least one mutation is within the second T cell epitope, and wherein the at least one mutation within the second T cell epitope is at one or more of amino acids 1134, K139, E140, or Q142 of the wild type a-sarcin.

6. The isolated nucleic acid of claim 1, encoding the modified sarcin polypeptide or the fusion protein comprising the modified sarcin polypeptide conjugated or fused to the heterologous targeting molecule, wherein at least one first mutation is within the first T cell epitope and at least one second mutation is within the second T cell epitope, wherein the at least one first mutation within the first T cell epitope is at one or more of amino acids D9, Q10, P13, T15, N16, or Y18 of the wild type a-sarcin and wherein the at least one second mutation within the second T cell epitope is at one or more of amino acids 1134, K139, E140, or Q142 of the wild type a- sarcin polypeptide.

7. An isolated nucleic acid encoding a modified sarcin polypeptide or a fusion protein comprising the modified sarcin polypeptide conjugated or fused to a heterologous targeting molecule, wherein the modified sarcin polypeptide comprises at least one mutation as compared to a wild type a-sarcin polypeptide having the amino acid sequence of SEQ ID NO:1, wherein the at least one mutation is within a first T cell epitope and/or a second T cell epitope of the wild type a- sarcin polypeptide, wherein the at least one mutation within the first T cell epitope is one or more of D9A, D9T, Q10K, Q10R, Q10A, P13l, T15G, T15Q, T15H, N16R, N16K, N16A, Y18H, Y18K, or Y18R and wherein the at least one mutation within the second T cell epitope is one or more of 1134A, K139D, K139E, K139G, K139Q, K139H, K139N, E140D, Q142D, Q142N, Q142T, Q142E, Q142R, or Q142G, and wherein the first T cell epitope consists of the amino acid sequence of SEQ ID NO:6 and the second T cell epitope consists of the amino acid sequence of SEQ ID NO.4.

8. The isolated nucleic acid of claim 7, encoding the modified sarcin polypeptide or the fusion protein comprising the modified sarcin polypeptide conjugated or fused to the heterologous targeting molecule, wherein the at least one mutation is within the first T cell epitope and is one or more of D9A, D9T, Q10K, Q10R, Q10A, P13l, T15G, T15Q, T15H, N16R, N16K, N16A, Y18H, Y18K, or Y18R.

9. The isolated nucleic acid of claim 7, encoding the modified sarcin polypeptide or the fusion protein comprising the modified sarcin polypeptide conjugated or fused to the heterologous targeting molecule, wherein the at least one mutation is within the second T cell epitope and is one or more of 1134A, K139D, K139E, K139G, K139Q, K139H, K139N, E140D, Q142D, Q142N, Q142T, Q142E, Q142R, or Q142G.

10. The isolated nucleic acid of claim 7, encoding the modified sarcin polypeptide or the fusion protein comprising the modified sarcin polypeptide conjugated or fused to the heterologous targeting molecule, wherein at least one first mutation is within the first T cell epitope and at least one second mutation is within the second T cell epitope, wherein the at least one first mutation within the first T cell epitope is one or more of D9A, D9T, Q10K, Q10R, Q10A, P13l, T15G, T15Q, T15H, N16R, N16K, N16A, Y18H, Y18K, or Y18R and the at least one second mutation within the second T cell epitope is one or more of I134A, K139D, K139E, K139G, K139Q, K139H, K139N, E140D, Q142D, Q142N, Q142T, Q142E, Q142R, or Q142G.

11. The isolated nucleic acid of claim 8, encoding the modified sarcin polypeptide or the fusion protein comprising the modified sarcin polypeptide conjugated or fused to the heterologous targeting molecule, wherein the at least one mutation within the first T cell epitope is D9T or P13l.

12. The isolated nucleic acid of claim 9, encoding the modified sarcin polypeptide or the fusion protein comprising the modified sarcin polypeptide conjugated or fused to the heterologous targeting molecule, wherein the at least one mutation within the second T cell epitope is Q142T.

13. The isolated nucleic acid of claim 10, encoding the modified sarcin polypeptide or the fusion protein comprising the modified sarcin polypeptide conjugated or fused to the heterologous targeting molecule, wherein the at least one first mutation within the first T cell epitope is D9T and the at least one second mutation within the second T cell epitope is Q142T.

14. The isolated nucleic acid of claim 10, encoding the modified sarcin polypeptide or the fusion protein comprising the modified sarcin polypeptide conjugated or fused to the heterologous targeting molecule, wherein the at least one first mutation within the first T cell epitope is P13l and the at least one second mutation within the second T cell epitope is Q142T.

15. A method of producing a modified sarcin polypeptide or a fusion protein comprising the modified sarcin polypeptide, the method comprising culturing a host cell according to claim 3 and purifying the modified sarcin polypeptide or fusion protein expressed from the host cell.

* * * * *